United States Patent
Attinger et al.

(10) Patent No.: US 12,281,169 B2
(45) Date of Patent: Apr. 22, 2025

(54) ANTIBODIES THAT BIND TO OX40 AND THEIR USES

(71) Applicant: Ichnos Sciences SA, La Chaux-de-Fonds (CH)

(72) Inventors: Antoine Attinger, La Chaux-de Fonds (CH); Stanislas Blein, La Chaux-de-Fonds (CH); Jonathan Albert Back, La Chaux-de-Fonds (CH); Rami Lissilaa, La Chaux-de-Fonds (CH); Samuel Hou, La Chaux-de-Fonds (CH)

(73) Assignee: Ichnos Sciences SA, La Chaux-de-Fonds (CH)

( * ) Notice: Subject to any disclaimer, the term of this patent is extended or adjusted under 35 U.S.C. 154(b) by 152 days.

(21) Appl. No.: 17/854,904

(22) Filed: Jun. 30, 2022

(65) Prior Publication Data
US 2022/0411526 A1    Dec. 29, 2022

Related U.S. Application Data

(60) Division of application No. 16/298,289, filed on Mar. 11, 2019, now Pat. No. 11,407,839, which is a continuation of application No. 15/348,774, filed on Nov. 10, 2016, now abandoned, which is a continuation of application No. 14/222,421, filed on Mar. 21, 2014, now abandoned, which is a continuation of application No. 13/545,708, filed on Jul. 10, 2012, now Pat. No. 8,748,585.

(60) Provisional application No. 61/506,491, filed on Jul. 11, 2011.

(51) Int. Cl.
C07K 16/28 (2006.01)
A61K 39/00 (2006.01)
A61K 39/395 (2006.01)
A61K 45/06 (2006.01)

(52) U.S. Cl.
CPC ...... *C07K 16/2878* (2013.01); *A61K 39/3955* (2013.01); *A61K 45/06* (2013.01); *A61K 2039/505* (2013.01); *C07K 2317/24* (2013.01); *C07K 2317/33* (2013.01); *C07K 2317/34* (2013.01); *C07K 2317/41* (2013.01); *C07K 2317/52* (2013.01); *C07K 2317/53* (2013.01); *C07K 2317/73* (2013.01); *C07K 2317/732* (2013.01); *C07K 2317/76* (2013.01); *C07K 2317/92* (2013.01); *C07K 2317/94* (2013.01); *G01N 2333/70578* (2013.01)

(58) Field of Classification Search
CPC ............ C07K 16/2878; C07K 2317/24; C07K 2317/41; C07K 2317/52; C07K 2317/76; C07K 2317/92; C07K 2317/94; A61K 39/3955; A61K 2039/505
See application file for complete search history.

(56) References Cited

U.S. PATENT DOCUMENTS

| | | |
|---|---|---|
| 4,816,567 A | 3/1989 | Cabilly et al. |
| 5,225,539 A | 7/1993 | Winter |
| 5,530,101 A | 6/1996 | Queen et al. |
| 5,571,894 A | 11/1996 | Wels et al. |
| 5,585,089 A | 12/1996 | Queen et al. |
| 5,587,458 A | 12/1996 | King et al. |
| 5,624,821 A | 4/1997 | Winter et al. |
| 5,641,870 A | 6/1997 | Rinderknecht et al. |
| 5,648,260 A | 7/1997 | Winter et al. |
| 5,677,425 A | 10/1997 | Bodmer et al. |
| 5,693,762 A | 12/1997 | Queen et al. |
| 5,869,046 A | 2/1999 | Presta et al. |
| 6,121,022 A | 9/2000 | Presta et al. |
| 6,165,745 A | 12/2000 | Ward et al. |
| 6,180,370 B1 | 1/2001 | Queen et al. |
| 6,180,377 B1 | 1/2001 | Morgan et al. |
| 6,194,551 B1 | 2/2001 | Idusogie et al. |
| 6,277,375 B1 | 8/2001 | Ward |
| 6,632,927 B2 | 10/2003 | Adair et al. |
| 6,875,433 B2 | 4/2005 | Hart et al. |
| 7,365,167 B2 | 4/2008 | Watkins et al. |
| 7,605,237 B2 | 10/2009 | Stevens et al. |
| 7,722,876 B2 | 5/2010 | Polonelli et al. |
| 8,110,664 B2 | 2/2012 | Sanders et al. |
| 8,748,585 B2 * | 6/2014 | Attinger .............. A61P 9/10 530/387.3 |
| 2010/0136030 A1 | 6/2010 | Salah-Eddine et al. |
| 2010/0196359 A1 | 8/2010 | Kato et al. |
| 2010/0215651 A1 | 8/2010 | Blein et al. |
| 2010/0254978 A1 | 10/2010 | Lawson et al. |

FOREIGN PATENT DOCUMENTS

| | | |
|---|---|---|
| EP | 183070 A2 | 6/1986 |
| EP | 244234 A2 | 11/1987 |

(Continued)

OTHER PUBLICATIONS

Blazar, B.R., et al., "Ligation of OX40 (CD134) regulates graft-versus-host disease (GVHD) and graft rejection in allogeneic bone marrow transplant recipients," Blood 101(9):3741-3748, American Society of Hematology, United States (2003).

(Continued)

*Primary Examiner* — Amy E Juedes
*Assistant Examiner* — Brian Hartnett
(74) *Attorney, Agent, or Firm* — Goodwin Procter LLP

(57) ABSTRACT

The present invention relates to antagonist antibodies or fragments thereof that bind to human OX40. More specifically, the present invention relates to an antagonist antibody or fragment thereof that binds to human OX40 comprising a heavy chain CDR1 comprising the amino acid sequence of SEQ ID NO: 1, and/or a heavy chain CDR2 comprising the amino acid sequence of SEQ ID NO: 2, and/or a heavy chain CDR3 comprising the amino acid sequence of SEQ ID NO: 3; and/or comprising a light chain CDR1 comprising the amino acid sequence of SEQ ID NO: 4, and/or a light chain CDR2 comprising the amino acid sequence of SEQ ID NO: 5 and/or a light chain CDR3 comprising the amino acid sequence of SEQ ID NO: 6.

28 Claims, 18 Drawing Sheets

Specification includes a Sequence Listing.

(56) References Cited

FOREIGN PATENT DOCUMENTS

| EP | 0338841 A1 | 10/1989 |
|---|---|---|
| EP | 402226 A1 | 12/1990 |
| EP | 2631246 A1 | 8/2013 |
| WO | WO-8704462 A1 | 7/1987 |
| WO | WO-8901036 A1 | 2/1989 |
| WO | WO-9311161 A1 | 6/1993 |
| WO | WO-9316185 A2 | 8/1993 |
| WO | WO-9413804 A1 | 6/1994 |
| WO | WO-9429351 A2 | 12/1994 |
| WO | WO-0042072 A2 | 7/2000 |
| WO | WO-03035835 A2 | 5/2003 |
| WO | WO-2007062245 A2 | 5/2007 |
| WO | WO-2008106116 A2 | 9/2008 |
| WO | WO-2010095031 A2 | 8/2010 |
| WO | WO-2010096418 A2 | 8/2010 |

OTHER PUBLICATIONS

Compaan, D. M., and Hymowitz, S.G., "The Crystal Structure of Costimulatory OX40-OX40L Complex," Structure 14(8):1321-1330, Cell Press, United States (2006).

Huston, J.S., et al., "Protein engineering of antibody binding sites: Recovery of specific activity in an anti-digoxin single-chain Fv analogue produced in *Escherichia coli*," Proc. Natl. Acad. Sci. USA 85:5879-5883, National Academy of Sciences, United States (1988).

Imai-Nishiya, H., et al., "Double knockdown of alpha 1,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnol.7:84, BioMed Central, United Kingdom (2007).

International Search Report for International Application No. PCT/IB2012/053502, European Patent Office, Netherlands, mailed Sep. 10, 2012.

Kasai, Y., et al., "Molecular cloning of murine monoclonal anti-idiotypic Fab," J. Immunological Methods 155(1):77-89, Elsevier Science Publishers B.V., Netherlands (1992).

Kotani, A., et al., "Correlation of peripheral blood OX40+ (CD134+) T-cells with chronic graft-versus-host disease in patients who underwent allogeneic hematopoietic stem cell transplantation," Blood 98:3162-3164, American Society of Hematology, United States (2001).

Longmore, G.D., and Schachter, H., "Product-identification and substrate-specificity studies of the GDP-L-fucose: 2-acetamido-2-deoxy-beta-D-glucoside (FUC-Asn-linked GlcNAc) 6-alpha-L-fucosyltransferase in a Golgi-rich fraction from porcine liver," Carbohydr. Res. 100:365-392, Elsevier, Netherlands (1982).

MacCallum, R.M., et al., "Antibody-antigen Interactions: Contact analysis and binding site topography," J. Mol. Biol. 262:732-745, Academic Press Inc., United States (1996).

O'Flaherty, E., et al., "Regulation of T-cell apoptosis: a mixed lymphocyte reaction model," Immunology 100(3):289-299, Blackwell Science Ltd., United Kingdom (2000).

Panka, D.J., et al., "Variable region framework differences result in decreased or increased affinity of variant anti-digoxin antibodies," Proc. Natl. Acad. Sci. USA 85:3080-3084, National Academy of Sciences, United States (1988).

Paterson, D., et al., "Antigens of activated rat T lymphocytes including a molecule of 50,000 Mr detected only on CD4 positive T blasts," Mol. Immunol. 24(12):1281-1290, Pergamon Press, United Kingdom (1987).

Rudikoff, S., et al., "Single amino acid substitution altering antigen-binding specificity," Proc. Natl. Acad. Sci. USA 79:1979-1983, National Academy of Sciences, United States (1982).

Salek-Ardakani, S., et al., "OX40:OX40L Axis: Emerging Targets for Immunotherapy of Human Disease," Curr. Immunol. Rev. 2:37-53, Bentham Science Publishers B.V., United Arab Emirates (2006).

Simpson, D., "New Developments in the Prophylaxis and Treatment of Graft versus Host Disease," Expert Opin. Pharmacother. 2(7):1109-1117, Informa Healthcare, United Kingdom (2001).

Valzasina, B., et al., "Triggering of OX40 (CD134) on CD4+CD25+ T cell blocks their inhibitory activity : a novel regulatory role for OX40 and its comparison with GITR," Blood 105(7):2845-2851, American Society of Hematology, United States (2005).

Van Der Keyl, H., et al., "Disparity in the kinetics of onset of hypermutation in immunoglobulin heavy and light chains," Immunology and Cell Biology 78(3):224-237, University of Adelaide, Australia (2000 ).

Xhaard, A., et al., "Use of monoclonal antibodies in prophylaxis and treatment of acute and chronic graft-versus-host disease in 2011," Bull. Cancer 98(8):889-899, John Libbey Eurotext, France (Aug. 2011).

Xiaoyan, Z., et al., "Expression of OX40 (CD134) on CD4+ T-cells from patients with myasthenia gravis," *Clinical and Experimental Immunology* 143:110-116, British Society of Immunology, United Kingdom (2005).

Allen, T.M., "Ligand-targeted therapeutics in anticancer therapy," Nat. Rev. Cancer 2:750-763, Nature Portfolio, Germany (2002).

Arnold, K., et al., "The SWISS-MODEL workspace: a web-based environment for protein structure homology modelling," Bioinformatics 22(2):195-201, Oxford University Press, United Kingdom (2006).

Arnon, et al., "Monoclonal Antibodies for Immunotargeting of Drugs in Cancer Therapy," in *Monoclonal Antibodies and Cancer Therapy*, Reisfield, et al., eds., pp. 243-256, Allan R. Liss, Inc., United States (1985).

Barbas, C., et al., "Recognition of DNA by synthetic antibodies," J. Am. Chem. Soc. 116:2161-2162, American Chemical Society, United States (1994).

Beiboer, S.H., et al., "Guided selection of a pan carcinoma specific antibody reveals similar binding characteristics yet structural divergence between the original murine antibody and its human equivalent," J. Mol. Biol. 296:833-849, Elsevier, Netherlands (2000).

Bensmana, M., et al., "The human immunoglobulin pseudo-gamma IGHGP gene shows no major structural defect," Nucleic Acids Res. 16(7):3108, Oxford University Press, United Kingdom (1988).

Bird, R.E., et al., "Single-chain antigen-binding proteins," Science 242:423-426, American Association for the Advancement of Science, United States (1988).

Bodmer, J.L., et al., "The molecular architecture of the TNF superfamily," Trends Biochem. Sci. 27:19-26, Elsevier, Netherlands (2002).

Brennan, M., et al., "Preparation of bispecific antibodies by chemical recombination of monoclonal immunoglobulin G1 fragments," Science 229:81-83, American Association for the Advancement of Science, United States (1985).

Bromelow, K.V., et al., "Whole blood assay for assessment of the mixed lymphocyte reaction," J. Immunol. Methods 247(1-2):1-8, Elsevier, Netherlands (2001).

Carter, P., et al., "High level *Escherichia coli* expression and production of a bivalent humanized antibody fragment," Biotechnology (NY) 10(2):163-167, Nature Portfolio, Germany (1992).

Chothia, C., and Lesk, A.M., "Canonical structures for the hypervariable regions of immunoglobulins," J. Mol. Biol. 196:901-917, Elsevier, Netherlands (1987).

Coloma, M.J., and Morrison, S.L., "Design and production of novel tetravalent bispecific antibodies," Nat. Biotechnol. 15(2):159-163, Nature Portfolio, Germany (1997).

Cox, J.P., et al., "A directory of human germ-line V kappa segments reveals a strong bias in their usage," Eur. J. Immunol. 24:827-836, Wiley-VCH, Germany (1994).

Dariavach, P., et al., "Human immunoglobulin C lambda 6 gene encodes the Kern+Oz-lambda chain and C lambda 4 and C lambda 5 are pseudogenes," Proc. Natl. Acad. Sci. USA 84(24):9074-9078, National Academy of Sciences, United States (1987).

Dupont, B., and Hansen, J.A., "Human mixed-lymphocyte culture reaction: genetics, specificity, and biological implications," Adv. Immunol. 23:107-202, Elsevier, Netherlands (1976).

(56) References Cited

OTHER PUBLICATIONS

Edelman, G.M., et al., "The covalent structure of an entire gammaG immunoglobulin molecule," Proc. Natl. Acad. Sci. USA 63(1):78-85, National Academy of Sciences, United States (1969).

Frangione, B., et al., "Human lambda light-chain constant region gene CMor lambda: the primary structure of lambda VI Bence Jones protein Mor," Proc. Natl. Acad. Sci. USA 82(10):3415-3419, National Academy of Sciences, United States (1985).

Garber, E., and Demarest, S.J., "A broad range of Fab stabilities within a host of therapeutic IgGs," Biochem. Biophys. Res. Commun. 355:751-757, Elsevier, Netherlands (2007).

Hall, T.A., "BioEdit: a user-friendly biological sequence alignment editor and analysis program for Windows 95/98/NT," Nucleic Acids. Symp. Ser. 41:95-98, Oxford Academics, United Kingdom (1999).

Hellstrom, et al ., "Antibodies for Drug Delivery" in *Controlled Drug Delivery*, $2^{nd}$ Edition, Robinson, et al., eds., pp. 623-653, Marcel Dekker, Inc., 1987.

Holliger, P., et al., ""Diabodies": small bivalent and bispecific antibody fragments," Proc. Natl. Acad. Sci. USA 90:6444-6448, National Academy of Sciences, United States (1993).

Johnson, G., et al., "Kabat database and its applications: 30 years after the first variability plot," Nucleic Acids Res. 28:214-218, Oxford University Press, United Kingdom (2000).

Kaas, Q., et al., "IG, TR and IgSF, MHC and MhcSF: what do we learn from the IMGT Colliers de Perles?" Brief. Funct. Genomic. Proteomic. 6(4):253-264, Oxford University Press, United Kingdom (2008).

Kabat, E.A., et al., *Sequences of Proteins of Immunological Interest*, $5^{th}$ Edition, United States Department of Health and Human Services, National Institutes of Health, United States (1991).

Kaufman, R.J., and Sharp, P.A., "Amplification and expression of sequences cotransfected with a modular dihydrofolate reductase complementary DNA gene," J. Mol. Biol. 159:601-621, Elsevier, Netherlands (1982).

Kearney, J.F., et al., "A new mouse myeloma cell line that has lost immunoglobulin expression but permits the construction of antibody-secreting hybrid cell lines," J. Immunol. 123(4):1548-1550, American Association of Immunologists, United States (1979).

Kim, D., et al., "Improved mammalian expression systems by manipulating transcriptional termination regions," Biotechnol. Prog. 19(5):1620-1622, Wiley, United States (2003).

Klimka, A., et al., "Human anti-CD30 recombinant antibodies by guided phage antibody selection using cell panning," Br. J. Cancer 83(2):252-260, Nature Portfolio, Germany (2000).

Koons, M.D., et al., "The replicator of the Epstein-Barr virus latent cycle origin of DNA replication, oriP, is composed of multiple functional elements," J. Virol. 75(22):10582-10592, American Society for Microbiology, United States (2001).

Lefranc, M.P., et al., "IMGT unique numbering for immunoglobulin and T cell receptor constant domains and Ig superfamily C-like domains," Dev. Comp. Immunol. 29(3):185-203, Elsevier, Netherlands (2005).

Lefranc, M.P., et al., "IMGT, the international ImMunoGeneTics database," Nucleic Acids Res. 27(1):209-212, Oxford University Press, United Kingdom (1999).

Lefranc, M.P., et al., "IMGT, the international ImMunoGeneTics database," Nucleic Acids Res. 29(1):207-209, Oxford University Press, United Kingdom (2001).

Lefranc, M.P., et al., "IMGT, the international ImMunoGeneTics database," Nucleic Acids Res. 31(1):307-310, Oxford University Press, United Kingdom (2003).

Martin, A.C.R., et al., "Modeling antibody hypervariable loops: a combined algorithm," Proc. Natl. Acad. Sci. USA 86:9268-9272, National Academy of Sciences, United States (1989).

Martin, A.C.R., et al., "Molecular modeling of antibody combining sites," Methods Enzymol. 203:121-153, Elsevier, Netherlands (1991).

McCafferty, J., et al., "Phage antibodies: filamentous phage displaying antibody variable domains," Nature 348:552-554, Nature Portfolio, Germany (1990).

Mizushima, T., et al., "Structural basis for improved efficacy of therapeutic antibodies on defucosylation of their Fc glycans," Genes Cells 16(11):1071-1080, Wiley-Blackwell, United States (2011).

Morimoto, K., et al., "Single-step purification of F(ab')2 fragments of mouse monoclonal antibodies (immunoglobulins G1) by hydrophobic interaction high performance liquid chromatography using TSKgel Phenyl-5PW," J. Biochem. & Biophys. Methods 24:107-117, Elsevier, Netherlands (1992).

Morrison, S.L., "Transfectomas provide novel chimeric antibodies," Science 229:1202, American Association for the Advancement of Science, United States (1985).

Murphy, W.J., et al., "The huPBL-SCID mouse as a means to examine human immune function in vivo," Semin. Immunol. 8(4):233-241, Academic Press Inc., United States (1996).

Order, S., "Analysis, Results, and Future Prospective of the Therapeutic Use of Radiolabeled Antibody in Cancer Therapy," in *Monoclonal Antibodies for Cancer Detection and Therapy*, Baldwin et al., eds., pp. 303-316, Academic Press, United States (1985).

Kreitman, R.J., "Immunotoxins in cancer therapy," Curr. Opin. Immunol. 11:570-578, Elsevier Ltd., United Kingdom (1999).

Payne, G., "Progress in immunoconjugate cancer therapeutics," Cancer Cell 3:207-212, Cell Press, United States (2003).

Pedersen, J.T., et al., "Antibody Modelling: Beyond Homology," Immunomethods 1:126-136, Elsevier, Netherlands (1992).

Rader, C., et al., "A phage display approach for rapid antibody humanization: designed combinatorial V gene libraries," Proc. Natl. Acad. Sci. USA 95:8910-8915, National Academy of Sciences, United States (1998).

Rees, A.R., et al., "Antibody Combining Sites: Structure and Prediction," in *Protein Structure Prediction*, Sternberg, M.J.E., ed., pp. 141-172, Oxford University Press, United Kingdom (1996).

Retter, I., et al., "VBASE2, an integrative V gene database," Nucleic Acids Res. 33, Oxford University Press, United Kingdom (2005).

Ruiz, M., et al., "IMGT, the international ImMunoGeneTics database," Nucleic Acids Res 28(1):219-221, Oxford University Press, United Kingdom (2000).

Saito, G., et al., "Drug delivery strategy utilizing conjugation via reversible disulfide linkages: role and site of cellular reducing activities," Adv. Drug Deliv. Rev. 55:199-215, Elsevier, Netherlands (2003).

Senter, P.D., and Springer, C.J., "Selective activation of anticancer prodrugs by monoclonal antibody-enzyme conjugates," Adv. Drug Deliv. Rev. 53:247-264, Elsevier, Netherlands (2001).

Taylor, L., and Schwartz, H., "Identification of a soluble OX40 isoform: development of a specific and quantitative immunoassay," J. Immunol. Methods. 255(1-2):67-72, Elsevier, Netherlands (2001).

Thorpe, "Antibody Carriers of Cytotoxic Agents in Cancer Therapy: A Review," in *Monoclonal Antibodies '84: Biological and Clinical Applications*, Pinchera, et al., eds., pp. 475-506 (1985).

Thorpe, P.E., and Ross, W.C., "The preparation and cytotoxic properties of antibody-toxin conjugates," Immunol. Rev. 62:119-158, Begell House, United States (1982).

Tomlinson, I., and Hollinger, P., "Methods for generating multivalent and bispecific antibody fragments," Methods Enzymol. 326:461-479, Elsevier, Netherlands (2000).

Tomlinson, I.M., et al., "The repertoire of human germline vH sequences reveals about fifty groups of VH segments with different hypervariable loops," J. Mol. Biol. 227(3):776-798, Elsevier, Netherlands (1992).

Trail, P.A., et al., "Monoclonal antibody drug immunoconjugates for targeted treatment of cancer," Cancer Immunol. Immunother. 52:328-337, Springer Science+Business Media, Germany (2003).

UniProt, "TNR4_HUMAN," Accession No. P43489, accessed at https://www.uniprot.org/uniprotkb/P43489/entry, accessed on Jul. 28, 2022, 6 pages.

UniProtKB, "Q6FGS4_HUMAN," UniProt Accession No. Q6FGS4, accessed at https://www.uniprot.org/uniprotkb/Q6FGS4/entry, accessed on Jul. 28, 2022, 1 page.

Urlaub, G., and Chasin, L.A., "Isolation of Chinese hamster cell mutants deficient in dihydrofolate reductase activity," Proc. Natl. Acad. Sci. USA 77:4216-4220, National Academy of Sciences, United States (1980).

(56) References Cited

OTHER PUBLICATIONS

Ward, E.S., et al., "Binding activities of a repertoire of single immunoglobulin variable domains secreted from *Escherichia coli*," Nature 341:544-546, Nature Portfolio, Germany (1989).
"Progress in Autoimmune Disease Research," National Institutes of Health, The Autoimmune Diseases Coordinating Committee Report to Congress, Mar. 2005, pp. 1-125 (NIH Publication No. 05-5140).
Holliger P, Hudson PJ. Engineered antibody fragments and the rise of single domains. Nat Biotechnol. Sep. 2005;23(9):1126-36.
Holt LJ et al., Domain antibodies: proteins for therapy. Trends Biotechnol. Nov. 2003;21(11):484-90.
"Alzheimer's" Mayo Clinic. Website downloaded Jul. 27, 2021 (Year: 2021).
"Ischemia" Mayo Clinic. Website downloaded Jul. 27, 2021 (Year: 2021).
"Stroke" Mayo Clinic. Website downloaded Jul. 27, 2021 (Year: 2021).

\* cited by examiner (A)

(B)

(A)

Antibody staining fluorescence ⟶

☐ Isotype control

▓ commercial anti-OX40

┆┆ 1D4

Figure 3 cont.
(B)
i
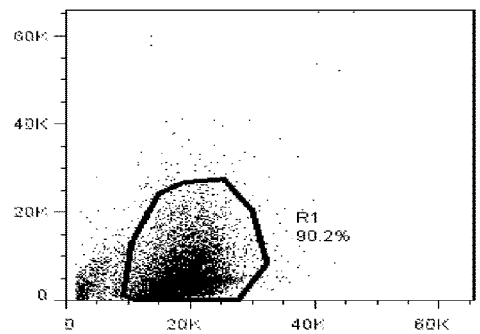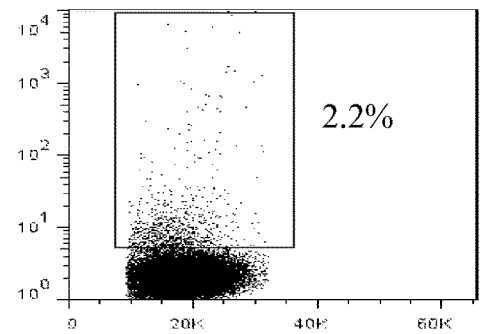
ii
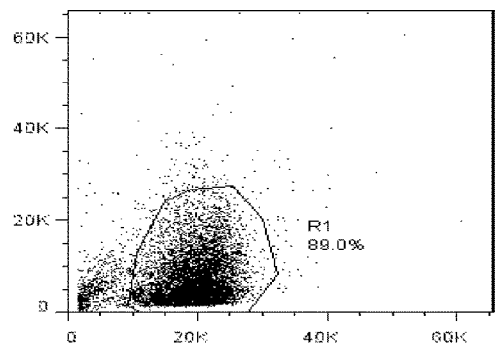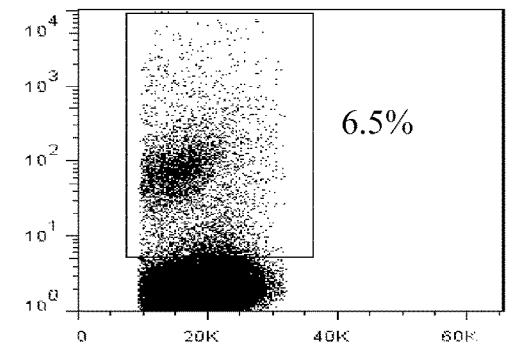
iii
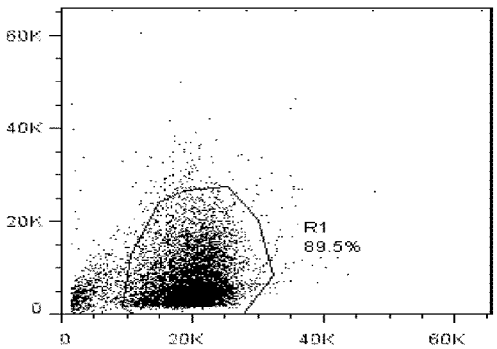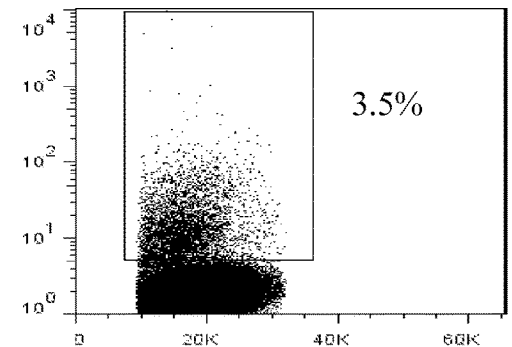

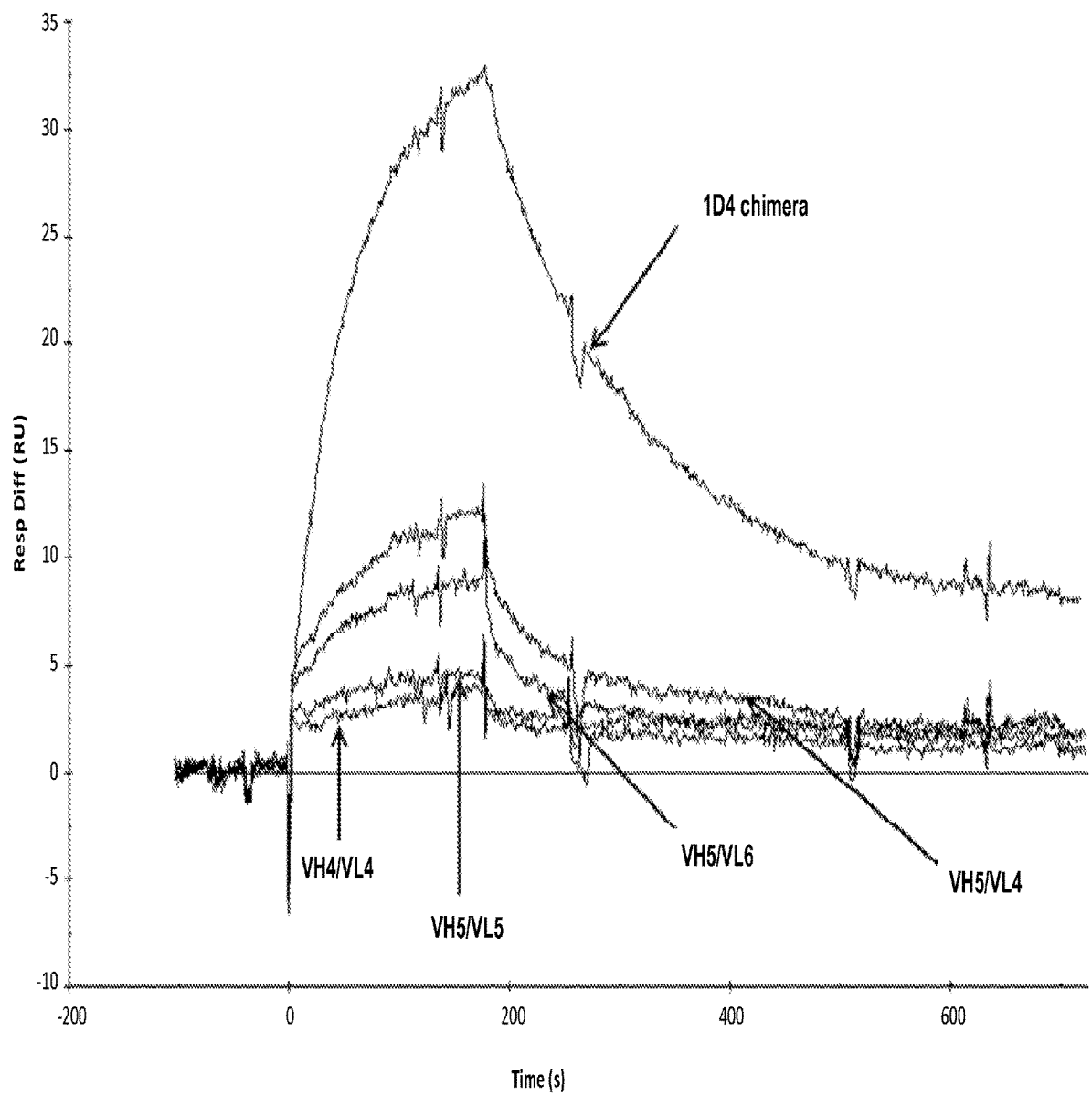

FIG. 5A

```
                                      10        20        30          40        50           60        70
                                 ....|....|....|....|....|....|.......|....|....|.......|....|....|....|
Kabat VH#                        12345678901234567890123456789012345ab67890123456789012abc345678901234567 89012345
1D4 VH                           QVTLKESGPGILQPSQTLSLTCSFSGFSLSTSGMGVGWIRQPSGKGLEWLAHIW~~~WDDDKYYNTALKSGLTISKDTSK
Human IGHV2-70*10                QVTLKESGPALVKPTQTLTLTCTFSGFSLSTSGMRVSWIRQPPGKALEWIARID~~~WDDDKYYSTSLKTRLTISKDTSK
VH1                              QVTLKESGPALVKPTQTLTLTCTFSGFSLSTSGMGVSWIRQPPGKALEWIARIW~~~WDDDKYYSTSLKTRLTISKDTSK
VH2  [T23S]                      QVTLKESGPALVKPTQTLTLTCSFSGFSLSTSGMGVSWIRQPPGKALEWIARIW~~~WDDDKYYSTSLKTRLTISKDTSK
VH3  [R50H]                      QVTLKESGPALVKPTQTLTLTCTFSGFSLSTSGMGVSWIRQPPGKALEWIAHIW~~~WDDDKYYSTSLKTRLTISKDTSK
VH4  [T23S/R50H]                 QVTLKESGPALVKPTQTLTLTCSFSGFSLSTSGMGVSWIRQPPGKALEWIAHIW~~~WDDDKYYSTSLKTRLTISKDTSK
VH5  [T23S/R50H/S60N/S62A]       QVTLKESGPALVKPTQTLTLTCSFSGFSLSTSGMGVSWIRQPPGKALEWIAHIW~~~WDDDKYYNTALKTRLTISKDTSK
VH6  [T23S/S35bG/R50H/S60N/S62A  QVTLKESGPALVKPTQTLTLTCSFSGFSLSTSGMGVGWIRQPPGKALEWIAHIW~~~WDDDKYYNTALKTRLTISKDTSK
VH7  [T23S/S35bG/I48L/R50H/S60N  QVTLKESGPALVKPTQTLTLTCSFSGFSLSTSGMGVGWIRQPPGKALEWLAHIW~~~WDDDKYYNTALKTRLTISKDTSK 80         90       100            110
                                 ....|.......|....|....|....|................|....|...
Kabat VH#                        6789012abc345678901234567890abcdefghijk1234567890123
1D4 VH                           NQVFLKIASVDTTDTATYYCARIDWDGF~~~~~~~~~~~AYWGQGTLVTVSS
Human IGHV2-70*10                NQVVLTMTNMDPVDTATYYCARIYF~~~~~~~~~~~~~DYWGQGTLVTVSS
VH1                              NQVVLTMTNMDPVDTATYYCARIDWDGF~~~~~~~~~~~AYWGQGTLVTVSS
VH2  [T23S]                      NQVVLTMTNMDPVDTATYYCARIDWDGF~~~~~~~~~~~AYWGQGTLVTVSS
VH3  [R50H]                      NQVVLTMTNMDPVDTATYYCARIDWDGF~~~~~~~~~~~AYWGQGTLVTVSS
VH4  [T23S/R50H]                 NQVVLTMTNMDPVDTATYYCARIDWDGF~~~~~~~~~~~AYWGQGTLVTVSS
VH5  [T23S/R50H/S60N/S62A]       NQVVLTMTNMDPVDTATYYCARIDWDGF~~~~~~~~~~~AYWGQGTLVTVSS
VH6  [T23S/S35bG/R50H/S60N/S62A  NQVVLTMTNMDPVDTATYYCARIDWDGF~~~~~~~~~~~AYWGQGTLVTVSS
VH7  [T23S/S35bG/I48L/R50H/S60N  NQVVLTMTNMDPVDTATYYCARIDWDGF~~~~~~~~~~~AYWGQGTLVTVSS
```

FIG. 5B

```
                                                       10        20        30        40        50        60        70
                                                ....|....|....|....|....|..........|....|....|....|....|....|....|....|
Kabat VL#                                       1234567890123456789012345 67abcdef8901234567890123456789012345678901234
1D4 VL                                          QIVLTQSPAILSASPGEKVTMTCRASS~~~~~~~SVSYMHWYQQKPGSSPKPWIYATSNLASGVPARFSGSGSGTSYSLT
Human IGKV 3-11*01                              EIVLTQSPATLSLSPGERATLSCRASQ~~~~~~~SVSSYLAWYQQKPGQAPRLLIYDASNRATGIPARFSGSGSGTDFTLT
VL1                                             EIVLTQSPATLSLSPGERATLSCRASS~~~~~~~SVSYYLAWYQQKPGQAPRLLIYATSNRATGIPARFSGSGSGTDFTLT
VL2 [L33M]                                      EIVLTQSPATLSLSPGERATLSCRASS~~~~~~~SVSYYMAWYQQKPGQAPRLLIYATSNRATGIPARFSGSGSGTDFTLT
VL3 [F71Y]                                      EIVLTQSPATLSLSPGERATLSCRASS~~~~~~~SVSYYLAWYQQKPGQAPRLLIYATSNRATGIPARFSGSGSGTDYTLT
VL4 [L33M/F71Y]                                 EIVLTQSPATLSLSPGERATLSCRASS~~~~~~~SVSYYMAWYQQKPGQAPRLLIYATSNRATGIPARFSGSGSGTDYTLT
VL5 [L33M/L46P/L47W/F71Y]                       EIVLTQSPATLSLSPGERATLSCRASS~~~~~~~SVSYYMAWYQQKPGQAPRPWIYATSNRATGIPARFSGSGSGTDYTLT
VL6 [E1Q/L33M/L46P/L47W/F71Y]                   QIVLTQSPATLSLSPGERATLSCRASS~~~~~~~SVSYYMAWYQQKPGQAPRPWIYATSNRATGIPARFSGSGSGTDYTLT
VL7 [Y31del/L33M/F71Y]                          EIVLTQSPATLSLSPGERATLSCRASS~~~~~~~~SVSYMAWYQQKPGQAPRLLIYATSNRATGIPARFSGSGSGTDYTLT
VL8 [Y31del/L33M/A34H/F71Y]                     EIVLTQSPATLSLSPGERATLSCRASS~~~~~~~~SVSYMHWYQQKPGQAPRLLIYATSNRATGIPARFSGSGSGTDYTLT
VL9 [Y31del/L33M/A34H/L46P/L47W/F71Y]           EIVLTQSPATLSLSPGERATLSCRASS~~~~~~~~SVSYMHWYQQKPGQAPRPWIYATSNRATGIPARFSGSGSGTDYTLT
VL10 [Y31del/L33M/R54L/T56S/F71W]               EIVLTQSPATLSLSPGERATLSCRASS~~~~~~~~SVSYMAWYQQKPGQAPRLLIYATSNLASGIPARFSGSGSGTDYTLT
VL11 [Y31del/L33M/A34H/R54L/T56S/F71Y]          EIVLTQSPATLSLSPGERATLSCRASS~~~~~~~~SVSYMHWYQQKPGQAPRLLIYATSNLASGIPARFSGSGSGTDYTLT 80        90       100
                                                 ....|....|....|....|..........|....|...
Kabat VL#                                        567890123456789012345abcdef67890123456a7
1D4 VL                                           INRVEAEDAATYYCQQWSSNP~~~~~~WTFGGGTKLEI~K
Human IGKV 3-11*01                               ISSLEPEDFAVYYCQQRSNWP~~~~~~WTFGQGTKVEI~K
VL1                                              ISSLEPEDFAVYYCQQWSSNP~~~~~~WTFGQGTKVEI~K
VL2 [L33M]                                       ISSLEPEDFAVYYCQQWSSNP~~~~~~WTFGQGTKVEI~K
VL3 [F71Y]                                       ISSLEPEDFAVYYCQQWSSNP~~~~~~WTFGQGTKVEI~K
VL4 [L33M/F71Y]                                  ISSLEPEDFAVYYCQQWSSNP~~~~~~WTFGQGTKVEI~K
VL5 [L33M/L46P/L47W/F71Y]                        ISSLEPEDFAVYYCQQWSSNP~~~~~~WTFGQGTKVEI~K
VL6 [E1Q/L33M/L46P/L47W/F71Y]                    ISSLEPEDFAVYYCQQWSSNP~~~~~~WTFGQGTKVEI~K
VL7 [Y31del/L33M/F71Y]                           ISSLEPEDFAVYYCQQWSSNP~~~~~~WTFGQGTKVEI~K
VL8 [Y31del/L33M/A34H/F71Y]                      ISSLEPEDFAVYYCQQWSSNP~~~~~~WTFGQGTKVEI~K
VL9 [Y31del/L33M/A34H/L46P/L47W/F71Y]            ISSLEPEDFAVYYCQQWSSNP~~~~~~WTFGQGTKVEI~K
VL10 [Y31del/L33M/R54L/T56S/F71Y]                ISSLEPEDFAVYYCQQWSSNP~~~~~~WTFGQGTKVEI~K
VL11 [Y31del/L33M/A34H/R54L/T56S/F71Y]           ISSLEPEDFAVYYCQQWSSNP~~~~~~WTFGQGTKVEI~K
```

ANTIBODIES THAT BIND TO OX40 AND THEIR USES

RELATED APPLICATION

This application claims benefit of U.S. provisional application No. 61/506,491 filed on Jul. 11, 2011; all of which are hereby incorporated by reference in their entirety

FIELD OF THE INVENTION

The present invention relates to antagonist antibodies or fragments thereof that bind to human OX40. More specifically, the present invention relates to an antagonist antibody or fragment thereof that binds to human OX40 comprising a heavy chain CDR1 comprising the amino acid sequence of SEQ ID NO: 1, and/or a heavy chain CDR2 comprising the amino acid sequence of SEQ ID NO: 2, and/or a heavy chain CDR3 comprising the amino acid sequence of SEQ ID NO: 3; and/or comprising a light chain CDR1 comprising the amino acid sequence of SEQ ID NO: 4, and/or a light chain CDR2 comprising the amino acid sequence of SEQ ID NO: 5 and/or a light chain CDR3 comprising the amino acid sequence of SEQ ID NO: 6.

BACKGROUND OF THE INVENTION

OX40 is a member of the TNFR-superfamily of receptors and was first identified in 1987 as a 50 kDa glycoprotein expressed on activated CD4+ T cells from the rat (Paterson D J et al., (1987) Mol. Immunol. 24: 1281-90). The extracellular ligand binding domain of OX40 is composed of 3 full cysteine-rich domains (CRDs) and a partial, fourth C-terminal CRD (Bodmer J L et al., (2002) Trends Biochem. Sci. 27: 19-26). The ligand for OX40 is OX40L (CD252) and 3 copies of OX40 bind to the trimeric ligand to form the OX40-OX40L complex (Compaan D M & Hymowitz S G (2006) Structure, 14: 1321-1330). OX40 is a membrane-bound receptor; however a soluble isoform has also been detected (Taylor L & Schwarz H (2001) J. Immunol. Methods, 255: 67-72). Unlike CD28, OX40 is not constitutively expressed on naïve T cells but is induced after engagement of the T-Cell Receptor (TCR). OX40 is a secondary costimulatory molecule, expressed after 24 to 72 hours following activation; its ligand, OX40L, is also not expressed on resting antigen presenting cells, but is following their activation. OX40 is expressed mainly by activated CD4+. T cells and to a limited extent, by activated CD8+ T cells (Salek-Ardakani S et al., (2006) Curr. Immunol. Rev. 2: 37-53).

SUMMARY OF THE INVENTION

The present disclosure relates generally to antagonist antibodies or fragments thereof that bind to human OX40, methods for their preparation and use, including methods for treating OX40 mediated disorders. The antagonist antibodies or fragments thereof of the present invention that bind to human OX40 are antagonistic antibodies and do not show agonistic effects and/or activate human OX40 on binding.

In one aspect, the present disclosure provides an antagonist antibody or fragment thereof that binds to human OX40 comprising a heavy chain CDR1 comprising the amino acid sequence of SEQ ID NO: 1, and/or a heavy chain CDR2 comprising the amino acid sequence of SEQ ID NO: 2, and/or a heavy chain CDR3 comprising the amino acid sequence of SEQ ID NO: 3; and/or comprising a light chain CDR1 comprising the amino acid sequence of SEQ ID NO: 4, and/or a light chain CDR2 comprising the amino acid sequence of SEQ ID NO: 5 and/or a light chain CDR3 comprising the amino acid sequence of SEQ ID NO: 6.

In a further aspect the present invention provides an antagonist antibody or fragment thereof that binds to human OX40 comprising a heavy chain variable region sequence comprising the amino acid sequence of SEQ ID NO: 7. In a further aspect the present invention provides an antagonist antibody or fragment thereof that binds to human OX40 comprising a heavy chain variable framework region that is the product of or derived from a human gene selected from the group consisting of: IGHV2-70*10 (SEQ ID NO: 19), IGHV2-70*01 (SEQ ID NO: 20), IGHV2-70*13 (SEQ ID NO: 21), IGHV2-5*09 (SEQ ID NO: 22), and IGHV2-70*11 (SEQ ID NO: 23).

In a further aspect the present invention provides an antagonist antibody or fragment thereof comprising a heavy chain sequence comprising the amino acid sequence of SEQ ID NO: 32 and wherein the heavy chain variable framework region comprises at least one amino acid modification from the corresponding heavy chain variable framework region of the corresponding murine antibody.

In a further aspect the present invention provides an antagonist antibody or fragment thereof that binds to human OX40 comprising a light chain variable region sequence comprising the amino acid sequence of SEQ ID NO: 8. In a further aspect the present invention provides an antagonist antibody or fragment thereof that binds to human OX40 comprising a light chain variable framework region that is the product of or derived from a human gene selected from the group consisting of: IGKV3-11*01 (SEQ ID NO: 24), IGKV1-39*01 (SEQ ID NO: 25), IGKV1D-39*01 (SEQ ID NO: 26), IGKV3-11*02 (SEQ ID NO: 27) and IGKV3-20*01 (SEQ ID NO: 28).

In a further aspect the present invention provides an antagonist antibody or fragment thereof comprising a light chain variable framework region that is the product of or derived from human gene IGKV3-11*01 (SEQ ID NO: 24) and wherein the light chain variable framework region comprises at least one amino acid modification from the corresponding framework region of the light chain variable region of the corresponding murine antibody.

In a further aspect the present invention provides an antagonist antibody or fragment thereof that binds to human OX40 comprising a heavy chain sequence selected from the group consisting of SEQ ID NOS: 32, 33, 34, 35, 36, 37 and 38. In a further aspect the present invention provides an antagonistic antibody or fragment thereof that binds to human OX40 comprising a light chain sequence selected from the group consisting of SEQ ID NOS: 39, 40, 41, 42, 43, 44, 45, 46, 47, 48 and 49.

In a further aspect the present invention provides an antagonist antibody or fragment thereof that binds to human OX40 comprising:
(a) a heavy chain sequence comprising the amino acid sequence of SEQ ID NO: 37 or 38; and
(b) a light chain sequence comprising the amino acid sequence of SEQ ID NO: 47.

In a further aspect the present invention provides an antagonistic antibody or fragment thereof that binds to human OX40 comprising a heavy chain variable region comprising the amino acid sequence selected from the group consisting of SEQ ID NOS: 58, 59, 79 and 80. In a further aspect the present invention provides an antagonistic antibody or fragment thereof that binds to human OX40 comprising a light chain variable region comprising the amino acid sequence selected from the group consisting of SEQ ID NOS: 60, 86, 87 and 89.

In a further aspect the present invention provides an antagonist antibody or fragment thereof that binds to human OX40 comprising:
  (a) a heavy chain variable region comprising the amino acid sequence of SEQ ID NO: 58 or 59; and
  (b) a light chain variable region comprising the amino acid sequence of SEQ ID NO: 60.

In a further aspect the present invention provides an antagonistic antibody or fragment thereof that binds to human OX40, wherein the antibody comprises a human IgG4 Fc region, wherein the antibody has no Fc-mediated cytotoxicity activity. In a further aspect the present invention provides an antagonistic antibody or fragment thereof that binds to human OX40, wherein the antibody comprises a human IGHG1 Fc region, wherein the antibody is competent for cytotoxicity mechanisms such as antibody dependent cellular cytotoxicity (ADCC). In a preferred aspect, the antagonistic antibody or fragment thereof that binds to human OX40 has a non fucosylated IGHG1 Fc region and exhibits enhanced Fc-mediated cytotoxicity mechanisms such as ADCC.

In another aspect, the disclosure of the present invention also describes antagonistic humanized antibodies or fragments thereof that bind with a similar affinity to human OX40 as the corresponding chimeric antibody e.g. retain at least 75% of the OX40 binding affinity ($K_D$) of the corresponding chimeric antibody or have at least equivalent or higher OX40 binding affinity ($K_D$) when compared to the corresponding chimeric antibody. In a further aspect the present invention provides an antagonist antibody or fragment thereof that binds to an epitope within the second domain of human OX40 extracellular region.

The disclosure of the present invention also provides isolated nucleic acids encoding antibodies and fragments thereof that bind to human OX40, vectors and host cells comprising the nucleic acid or the vector. Compositions comprising the antagonist antibody or fragment thereof and a pharmaceutically acceptable carrier and immunoconjugates comprising the antagonist antibody or fragment thereof linked to a therapeutic agent are also provided.

The present disclosure also provides methods for treating OX40 mediated disorders. In one aspect, in an in vitro model of alloreactive T cell activation and proliferation (mixed lymphocyte reaction; MLR), an antagonistic antibody or fragment thereof efficiently inhibits MLR in two different individuals (responders), with an $EC_{50}$ value of approximately 100 ng/mL. Furthermore, in a xenogenic graft versus host reaction, a model for allogenic graft versus host disease (GVHD) observed after bone marrow transplant in human patients, an antagonistic antibody or fragment thereof potently suppressed the GVHD reaction.

The present disclosure also provides kits and articles of manufacture comprising the antibody or fragments thereof, a composition or an immunoconjugate for the treatment of an OX40 mediated disorder.

BRIEF DESCRIPTION OF THE FIGURES

FIGS. 4A, 4B, 4C, 4D, 4E, and 4F: Surface Plasmon resonance measurements of anti-OX40 antibodies. Data are expressed as number of response (abbreviated RU; Y axis) vs. time (X axis).
  FIG. 4A—VH1/VL1 antibody vs 1D4 chimera.
  FIG. 4B—VH1, VH2, and VH3 based humanized antibodies (as indicated) vs 1D4 chimera.
  FIG. 4C—examples of poor binders: VH4/VL4, VH5/VL4, VH5/VL5, and VH5/VL6.
  FIG. 4D—examples of weak binders (VH5/VL9 and VH4/VL9) and good binders (VH6/VL9 and VH7/VL9).
  FIG. 4E—VH7 based humanized antibodies.
  FIG. 4F—VH6/VL9 has best binding properties over 1D4 chimera and humanized variant VH7/VL9.

FIGS. 5A and 5B: Sequence Alignment. Alignment of the heavy chain (FIG. 5A) or light chain (FIG. 5B) variable region of 1D4 with selected germline frameworks (IGHV 2-70*10 (SEQ ID NO: 19) and IGKV3-11*01 (SEQ ID NO: 24)) from IMGT and back-mutated variable region variants (VH1 (SEQ ID NO: 29), VH2 (SEQ ID NO: 77), VH3 (SEQ ID NO: 78), VH4 (SEQ ID NO: 79), VH5 (SEQ ID NO: 80), VH6 (SEQ ID NO: 58), VH7 (SEQ ID NO: 59), (VL1 (SEQ ID NO: 30), VL2 (SEQ ID NO: 81), VL3 (SEQ ID NO: 82), VL4 (SEQ ID NO: 83), VL5 (SEQ ID NO: 84), VL6 (SEQ ID NO: 85), VL7 (SEQ ID NO: 86), VL8 (SEQ ID NO: 87), VL9 (SEQ ID NO: 60) VL10 (SEQ ID NO: 88), VL11 (SEQ ID NO: 89).

DETAILED DESCRIPTION OF THE INVENTION

Figure 1:
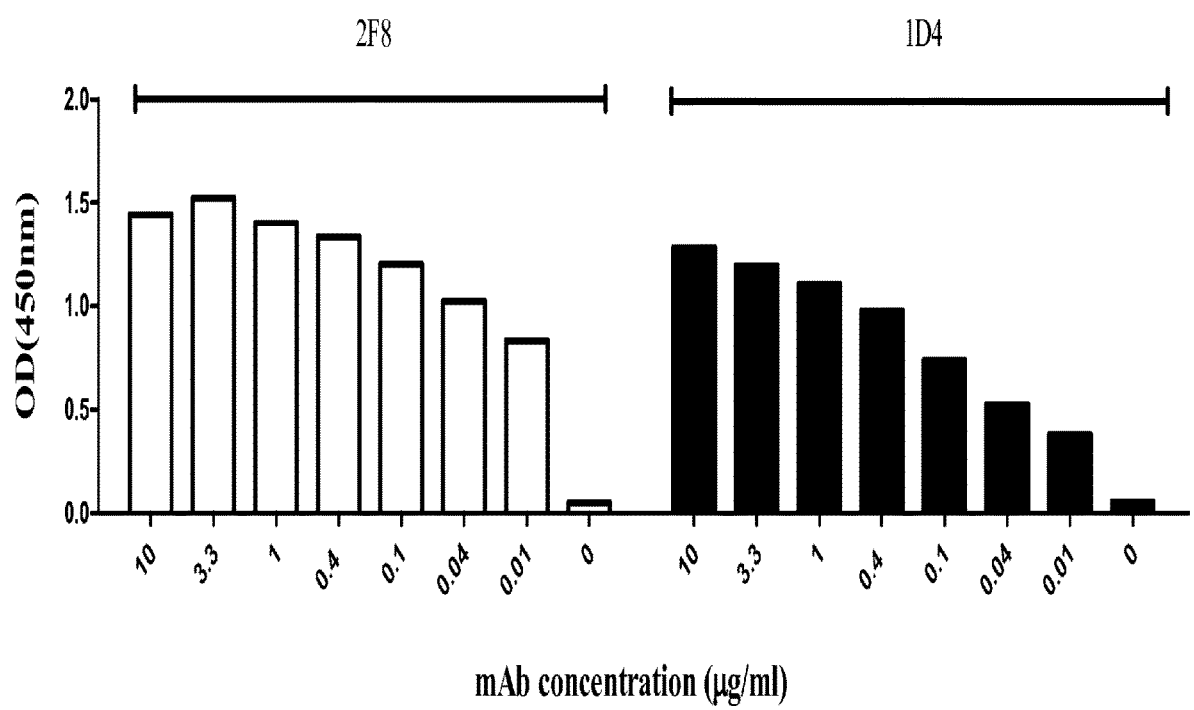
FIG. 1: (A) Direct-binding ELISA on immobilized recombinant human OX40-his. Binding of chimeric 2F8 and 1D4 antibodies on human OX40 was measured by direct ELISA. Various concentrations (ranging from 10 to 0.01 mg/ml) of 1D4 (black histograms) and 2F8 (white histograms) were incubated with 2 mg/ml of recombinant human OX40-his tagged protein coated overnight at 4° C. in a 96-well plate. Binding of each antibody to OX40 was detected by horseradish peroxidise (HRP)-conjugated anti human antibody. (B) Competitive ELISA on immobilized recombinant human OX40-Fc. Inhibitory effects of chimeric 1D4 and 2F8 on OX40/OX40L interaction were evaluated by blocking ELISA. Various concentrations (ranging from 10 to 0.01 mg/ml) of 1D4 (black histograms) and 2F8 (white histograms) were incubated with 2 mg/ml of recombinant human OX40-Fc tagged protein coated overnight at 4° C. in a 96-well plate. After five minutes, a fixed concentration of biotinylated recombinant human OX40L (0.04 mg/ml) was added to each well and incubated for 30 minutes at room temperature. Binding of OX40L to OX40 was detected using Streptavidin-HRP.
Figure 1:
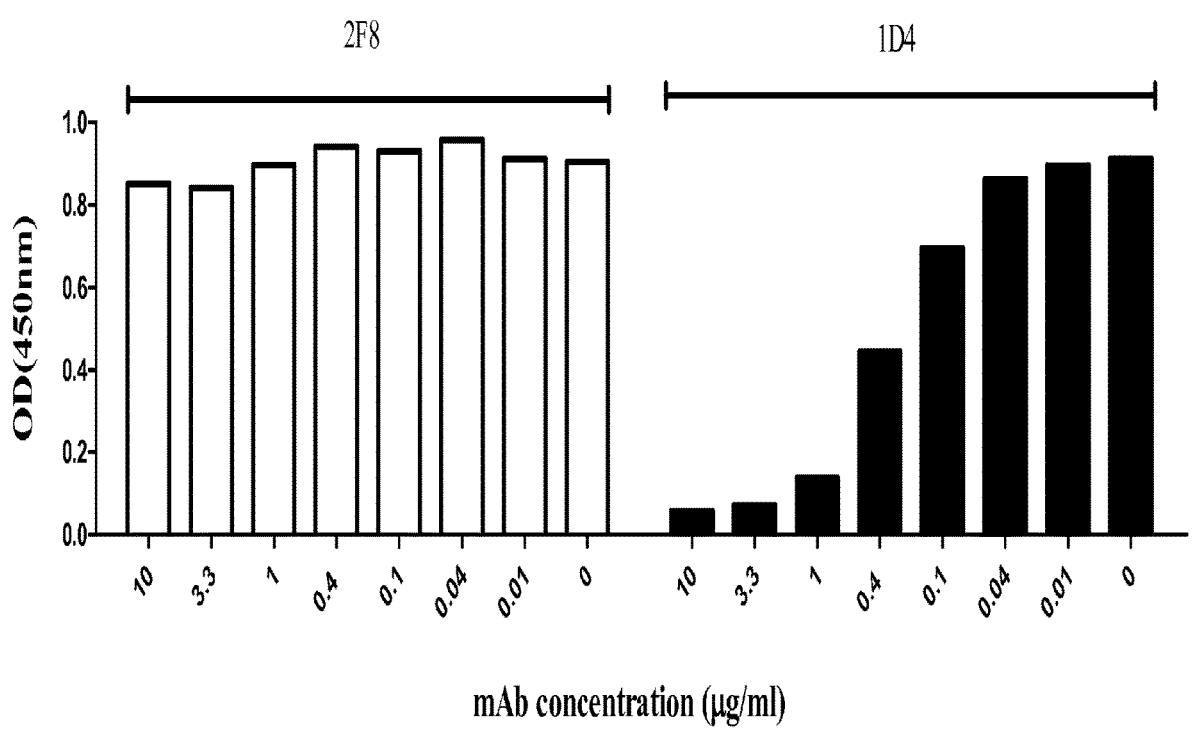
Figure 2:
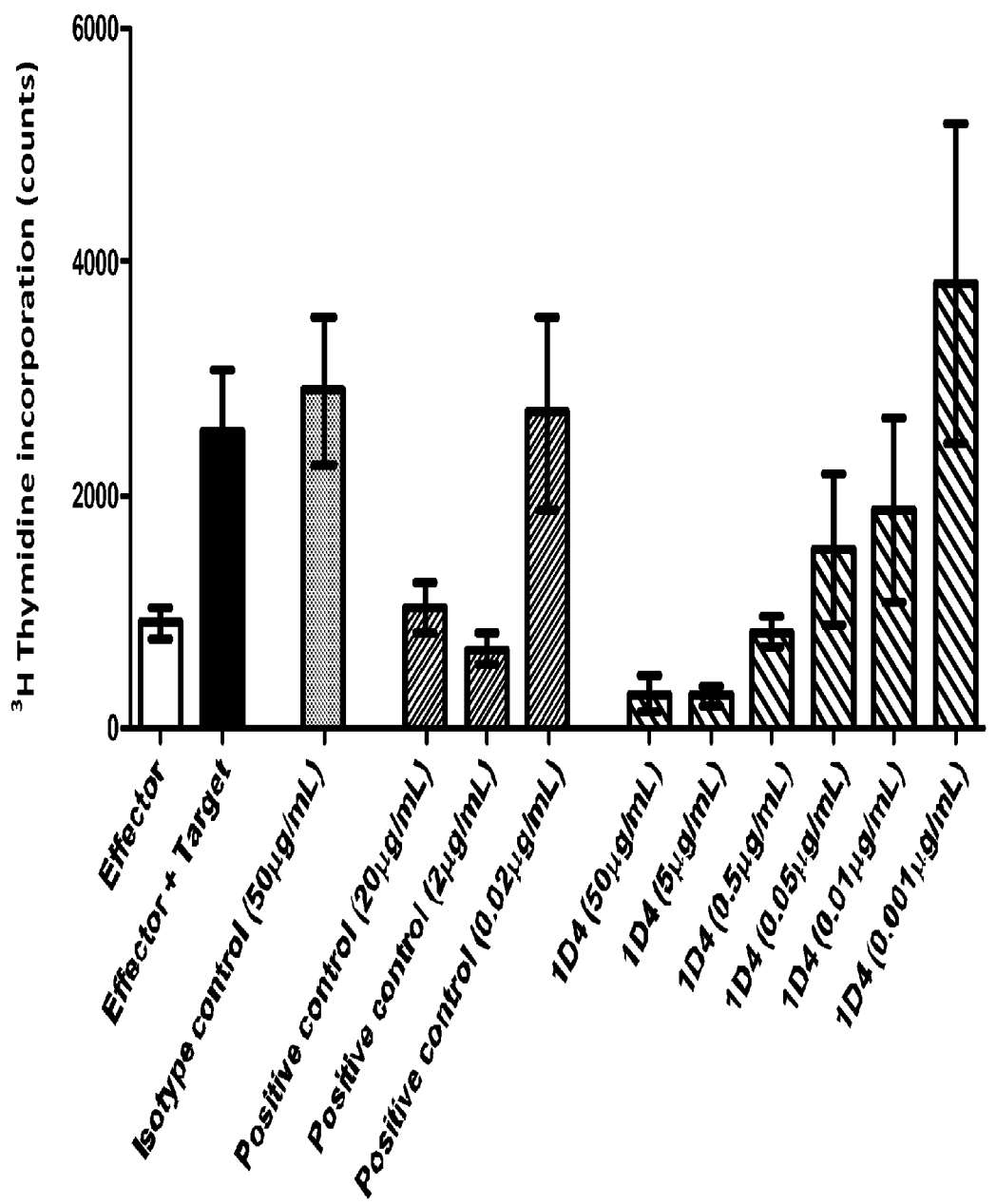
FIG. 2: One way mixed lymphocyte reaction (MLR) measured by $^3H$ thymidine incorporation. Bars show the mean $^3H$-thymidine incorporation (counts) of at least triplicates±standard error of the mean. Isotype control (trastuzumab) and positive control (efalizumab) are shown. Effector stands for only effector cells. Effector+target represent a measurement where antibodies have been omitted.

The present disclosure relates to antagonist antibodies and fragments thereof that bind to human OX40.

The term "human OX40" as used herein includes variants, isoforms, and species homologs of human OX40. Accordingly, antibodies of this disclosure may, in certain cases, cross-react with OX40 from species other than human. In certain embodiments, the antibodies may be completely specific for one or more human OX40 proteins and may not exhibit species or other types of non-human cross-reactivity. The complete amino acid sequence of an exemplary human OX40 has Swiss-Prot accession number P43489 (TNR4_HUMAN; SEQ ID NO: 12). OX40 is also known as CD134, TNFRSF4, ACT35 or TXGP1 L. Human OX40 is designated GeneID: 7293 by Entrez Gene, and HGNC: 11918 by HGNC. OX40 has also been designated CD134 (cluster of differentiation 134). OX40 can be encoded by the gene designated TNFRSF4/OX40.

The use of "human OX40" herein encompasses all known or as yet undiscovered alleles and polymorphic forms of human OX40. The terms "human OX40", "OX40" or "OX40 Receptor" are used herein equivalently and mean "human OX40" if not otherwise specifically indicated.

The term "OX40 ligand" or "OX40L" are used herein equivalently and include OX40 ligand, specifically human OX40 ligand. OX40L is a member of the TNF superfamily and is also known as gp34 or CD252. OX40L has also been designated CD252 (cluster of differentiation 252) and has the sequence database accession number P23510 (Swiss-Prot) or Q6FGS4 (Uniprot). OX40L is expressed on the surface of activated B cells, T cells, dendritic cells and endothelial cells.

The term "antibody or fragment thereof that binds to human OX40" as used herein includes antibodies or a fragment thereof that binds to human OX40 e.g. human OX40 in isolated form, with an affinity ($K_D$) of 500 nM or less, preferably 200 nM or less, more preferably 150 nM or less, more preferably 120 nM or less, even more preferably 110 nM or less. The term "antibody or fragment thereof that binds to human OX40" includes antibodies or antigenic binding fragments thereof.

The terms "antagonistic antibody" or "antagonist antibody" are used herein equivalently and include an antibody that is capable of inhibiting and/or neutralising the biological signalling activity of OX40, for example by blocking binding or substantially reducing binding of OX40 to OX40 ligand and thus inhibiting or reducing the signalisation pathway triggered by OX40 and/or inhibiting or reducing an OX40-mediated cell response like lymphocyte proliferation, cytokine expression, or lymphocyte survival.

The term "antibody" as referred to herein includes whole antibodies and any antigen binding fragments or single chains thereof. An "antibody" refers to a glycoprotein comprising at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR) with are hypervariable in sequence and/or involved in antigen recognition and/or usually form structurally defined loops, interspersed with regions that are more conserved, termed framework regions (FR or FW). Each VH and VL is composed of three CDRs and four FWs, arranged from amino-terminus to carboxy-terminus in the following order: FW1, CDR1, FW2, CDR2, FW3, CDR3, FW4. The amino acid sequences of FW1, FW2, FW3, and FW4 all together constitute the "non-CDR region" or "non-extended CDR region" of VH or VL as referred to herein.

The term "heavy chain variable framework region" as referred herein may comprise one or more (e.g., one, two, three and/or four) heavy chain framework region sequences (e.g., framework 1 (FW1), framework 2 (FW2), framework 3 (FW3) and/or framework 4 (FW4)). Preferably the heavy chain variable region framework comprises FW1, FW2 and/or FW3, more preferably FW1, FW2 and FW3. The term "light chain variable framework region" as referred herein may comprise one or more (e.g., one, two, three and/or four) light chain framework region sequences (e.g., framework 1 (FW1), framework 2 (FW2), framework 3 (FW3) and/or framework 4 (FW4)). Preferably the light chain variable region framework comprises FW1, FW2 and/or FW3, more preferably FW1, FW2 and FW3.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the First component (C1q) of the classical complement system.

Antibodies are grouped into classes, also referred to as isotypes, as determined genetically by the constant region. Human constant light chains are classified as kappa (Cκ) and lambda (Cλ) light chains. Heavy chains are classified as mu (μ), delta (δ), gamma (γ), alpha (α), or epsilon (s), and define the antibody's isotype as IgM, IgD, IgG, IgA, and IgE, respectively. Thus, "isotype" as used herein is meant any of the classes and/or subclasses of immunoglobulins defined by the chemical and antigenic characteristics of their constant regions. The known human immunoglobulin isotypes are IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), and IgE (IGHE). The so-called human immunoglobulin pseudo-gamma IGHGP gene represents an additional human immunoglobulin heavy constant region gene which has been sequenced but does not encode a protein due to an altered switch region (Bensmana M et al., (1988) Nucleic Acids Res. 16(7): 3108). In spite of having an altered switch region, the human immunoglobulin pseudo-gamma IGHGP gene has open reading frames for all heavy constant domains (CH1-CH3) and hinge. All open reading frames for its heavy constant domains encode protein domains which align well with all human immunoglobulin constant domains with the predicted structural features. This additional pseudo-gamma isotype is referred herein as IgGP or IGHGP. Other pseudo immunoglobulin genes have been reported such as the human immunoglobulin heavy constant domain epsilon P1 and P2 pseudo-genes (IGHEP1 and IGHEP2). The IgG class is the most commonly used for therapeutic purposes. In humans this class comprises subclasses IgG1, IgG2, IgG3 and IgG4. In mice this class comprises subclasses IgG1, IgG2a, IgG2b, IgG2c and IgG3.

The term "chimeric antibody" as used herein includes antibodies in which the variable region sequences are derived from one species and the constant region sequences are derived from another species, such as an antibody in which the variable region sequences are derived from a mouse antibody and the constant region sequences are derived from a human antibody.

The term "humanized antibody" or "humanized anti-OX40 antibody" as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term "Fab" or "Fab region" as used herein includes the polypeptides that comprise the VH, CH1, VL, and CL immunoglobulin domains. Fab may refer to this region in isolation, or this region in the context of a full length antibody or antibody fragment.

The term "Fc" or "Fc region", as used herein includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains C gamma 2 and C gamma 3 (Cγ2 and Cγ3) and the hinge between C gamma 1 (Cγ1) and C gamma 2 (Cγ2). Although the boundaries of the Fc region may vary, the human IgG heavy chain Fc region is usually defined to comprise residues C226 or P230 to its carboxyl-terminus, wherein the numbering is according to the EU numbering system. For human IgG1 the Fc region is herein defined to comprise residue P232 to its carboxyl-terminus, wherein the numbering is according to the EU numbering system (Edelman G M et al., (1969) Proc Natl Acad Sci USA, 63(1): 78-85). Fc may refer to this region in isolation or this region in the context of an Fc polypeptide, for example an antibody.

The term "hinge" or "hinge region" or "antibody hinge region" herein includes the flexible polypeptide comprising the amino acids between the first and second constant domains of an antibody. The "hinge region" as referred to herein is a sequence region of 6-62 amino acids in length, only present in IgA, IgD and IgG, which encompasses the cysteine residues that bridge the two heavy chains. Structurally, the IgG CH1 domain ends at EU position 220, and the IgG CH2 domain begins at residue EU position 237. Thus for IgG the antibody hinge is herein defined to include positions 221 (D221 in IgG1) to 231 (A231 in IgG1), wherein the numbering is according to the EU numbering system (Edelman G M et al., supra).

The term "parent antibody" or "parent immunoglobulin" as used herein includes an unmodified antibody that is subsequently modified to generate a variant. Said parent antibody may be a naturally occurring antibody, or a variant or engineered version of a naturally occurring antibody. Parent antibody may refer to the antibody itself, compositions that comprise the parent antibody, or the amino acid sequence that encodes it. By "parent anti-OX40 antibody" as used herein is meant an antibody or immunoglobulin that binds human OX40 and is modified to generate a variant. By "corresponding murine antibody" as used herein is meant a murine antibody or immunoglobulin that bind to human OX40 and that can be modified to generate a variant, specifically the murine antibody 1D4 as disclosed herein.

The term "variant antibody" or "antibody variant" as used herein includes an antibody sequence that differs from that of a parent antibody sequence by virtue of at least one amino acid modification compared to the parent. The variant antibody sequence herein will preferably possess at least about 80%, most preferably at least about 90%, more preferably at least about 95% amino acid sequence identity with a parent antibody sequence. Antibody variant may refer to the antibody itself, compositions comprising the antibody variant, or the amino acid sequence that encodes it.

The term "amino acid modification" herein includes an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution R94K refers to a variant polypeptide, in this case a heavy chain variable framework region variant, in which the arginine at position 94 is replaced with a lysine. For the preceding example, 94K indicates the substitution of position 94 with a lysine. For the purposes herein, multiple substitutions are typically separated by a slash. For example, R94K/L78V refers to a double variant comprising the substitutions R94K and L78V. By "amino acid insertion" or "insertion" as used herein is meant the addition of an amino acid at a particular position in a parent polypeptide sequence. For example, insert –94 designates an insertion at position 94. By "amino acid deletion" or "deletion" as used herein is meant the removal of an amino acid at a particular position in a parent polypeptide sequence. For example, R94-designates the deletion of arginine at position 94.

As used herein, the term "conservative modifications" or "conservative sequence modifications" is intended to refer to amino acid modifications that do not significantly affect or alter the binding characteristics of the antibody containing the amino acid sequence. Such conservative modifications include amino acid substitutions, insertions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions or within the framework regions of an antibody of the invention can be replaced with other amino acid residues from the same side chain family and the altered antibody (variant antibody) can be tested for retained function.

For all human immunoglobulin heavy chain constant domains numbering is according to the "EU numbering system" (Edelman G M et al., (1969) Proc Natl Acad Sci USA, 63(1): 78-85). For the human kappa immunoglobulin light chain constant domain (IGKC), numbering is according to the "EU numbering system" (Edelman G M et al., supra).

For the human lambda immunoglobulin light chain constant domains (IGLC1, IGLC2, IGLC3, IGLC6, and IGLC7), numbering is according to the "Kabat numbering system" (Kabat E A et al., (1991) Sequences of proteins of immunological interest. 5th Edition—US Department of Health and Human Services, NIH publication n° 91-3242) as described by Dariavach P et al., (1987) Proc Natl Acad Sci USA, 84(24): 9074-8 and Frangione B et al., (1985) Proc Natl Acad Sci USA, 82(10): 3415-9.

The term "variable domain" refers to the domains that mediates antigen-binding and defines specificity of a particular antibody for a particular antigen. In naturally occurring antibodies, the antigen-binding site consists of two variable domains that define specificity: one located in the heavy chain (VH) and the other located in the light chain (VL). In some cases, specificity may exclusively reside in only one of the two domains as in single-domain antibodies from heavy-chain antibodies found in camelids. The V regions are usually about 110 amino acids long, and consist of relatively invariant stretches of amino acid sequence called framework regions (FRs) of 15-30 amino acids separated by shorter regions of extreme variability called "hypervariable regions" that are 9-12 amino acids long. The variable domains of native heavy and light chains comprise four FRs, largely adopting a beat-sheet configuration, connected by three hypervariable regions, which form loops. The hypervariable regions in each chain are held together in close proximity by FRs, and with the hypervariable regions from the other chain, contribute to the formation of the antigen binding site of antibodies (see Kabat E A et al., supra). The term "hypervariable region" as used herein refers to the amino acid residues of an antibody which are responsible for antigen binding. The hypervariable region generally comprises amino acid residues from a "complementary determining region" or "CDR", the latter being of highest sequence variability and/or involved in antigen recognition. For all variable domains numbering is according to Kabat (Kabat E A et al., supra).

A number of CDR definitions are in use and are encompassed herein. The Kabat definition is based on sequence variability and is the most commonly used (Kabat E A et al., supra). Chothia refers instead to the location of the structural loops (Chothia C & Lesk A M (1987) J. Mol. Biol. 196: 901-917). The AbM definition is a compromise between the Kabat and the Chothia definitions and is used by Oxford Molecular's AbM antibody modelling software (Martin A C R et al., (1989) Proc. Natl Acad. Sci. USA, 86: 9268-72; Martin A C R et al., (1991) Methods Enzymol. 203: 121-153; Pedersen J T et al., (1992) Immunomethods, 1: 126-136; Rees A R et al., (1996) In Sternberg M. J. E. (ed.), Protein Structure Prediction. Oxford University Press, Oxford, 141-172). The contact definition has been recently introduced (MacCallum R M et al., (1996) J. Mol. Biol. 262: 732-745) and is based on an analysis of the available complex structures available in the Protein Databank. The definition of the CDR by IMGT®, the international ImMunoGeneTics information System® (http://www.imgt.org) is based on the IMGT numbering for all immunoglobulin and T cell receptor V-REGIONs of all species (IMGT®, the international ImMunoGeneTics information System®; Lefranc M P et al., (1991) Nucleic Acids Res. 27(1): 209-12; Ruiz M et al., (2000) Nucleic Acids Res. 28(1): 219-21; Lefranc M P (2001) Nucleic Acids Res. 29(1): 207-9; Lefranc M P (2003) Nucleic Acids Res. 31(1): 307-10; Lefranc M P et al., (2005) Dev. Comp. Immunol. 29(3): 185-203; Kaas Q et al., (2007) Briefings in Functional Genomics & Proteomics, 6(4): 253-64).

All Complementarity Determining Regions (CDRs) discussed in the present invention, are defined preferably according to IMGT®. The variable domain residues for each of these CDRs are as follows (numbering according to Kabat E A, et al., supra): LCDR1: 27-32, LCDR2: 50-52, LCDR3: 89-97, HCDR1: 26-35, HCDR2: 51-57 and HCDR3: 93-102. The "non-CDR region" of the VL region as used herein comprise the amino acid sequences: 1-26 (FR1), 33-49 (FR2), 53-88 (FR3), and 98-approximately 107 (FR4). The "non-CDR region" of the VH region as used herein comprise the amino acid sequences: 1-25 (FR1), 36-50 (FR2), 58-92 (FR3), and 103-approximately 113 (FR4).

The CDRs of the present invention may comprise "extended CDRs" which are based on the aforementioned definitions and have variable domain residues as follows: LCDR1: 24-36, LCDR2: 46-56, LCDR3:89-97, HCDR1: 26-36, HCDR2:47-65, HCDR3: 93-102. These extended CDRs are numbered as well according to Kabat et al., supra. The "non-extended CDR region" of the VL region as used herein comprise the amino acid sequences: 1-23 (FR1), 37-45 (FR2), 57-88 (FR3), and 98-approximately 107 (FR4). The "non-extended CDR region" of the VH region as used herein comprise the amino acid sequences: 1-25 (FR1), 37-46 (FR2), 66-92 (FR3), and 103-approximately 113 (FR4).

The term "full length antibody" as used herein includes the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region.

Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward E S et al., (1989) Nature, 341: 544-546) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird R E et al., (1988) Science 242: 423-426; Huston J S et al., (1988) Proc. Natl. Acad. Sci. USA, 85: 5879-83), (vii) bispecific single chain Fv dimers (PCT/US92/09965), (viii) "diabodies" or "triabodies", multivalent or multispecific fragments constructed by gene fusion (Tomlinson I & Hollinger P (2000) Methods Enzymol. 326: 461-79; WO94/13804; Holliger P et al., (1993) Proc. Natl. Acad. Sci. USA, 90: 6444-48) and (ix) scFv genetically fused to the same or a different antibody (Coloma M J & Morrison S L (1997) Nature Biotechnology, 15(2): 159-163).

The term "effector function" as used herein includes a biochemical event that results from the interaction of an antibody Fc region with an Fc receptor or ligand. Effector functions include FcγR-mediated effector functions such as ADCC (antibody dependent cell-mediated cytotoxicity) and ADCP (antibody dependent cell-mediated phagocytosis), and complement-mediated effector functions such as CDC (complement dependent cytotoxicity). An effector function of an antibody may be altered by altering, i.e. enhancing or reducing, preferably enhancing, the affinity of the antibody for an effector molecule such as an Fc receptor or a complement component. Binding affinity will generally be varied by modifying the effector molecule binding site, and in this case it is appropriate to locate the site of interest and modify at least part of the site in a suitable way. It is also envisaged that an alteration in the binding site on the antibody for the effector molecule need not alter significantly the overall binding affinity but may alter the geometry of the interaction rendering the effector mechanism ineffective as in non-productive binding. It is further envisaged that an effector function may also be altered by modifying a site not directly involved in effector molecule binding, but otherwise involved in performance of the effector function. By altering an effector function of an antibody it may be possible to control various aspects of the immune response, e.g. enhancing or suppressing various reactions of the immune system, with possible beneficial effects in diagnosis and therapy.

As used herein, the term "OX40-mediated disorder" includes conditions such as allergy, asthma, COPD, rheumatoid arthritis, psoriasis and diseases associated with autoimmunity and inflammation.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Preferably the subject is human.

Anti-OX40 Antibodies

In a first aspect the present invention provides an antagonist antibody or fragment thereof that binds to human OX40 comprising a heavy chain CDR1 comprising the amino acid sequence of SEQ ID NO: 1, and/or a heavy chain CDR2 comprising the amino acid sequence of SEQ ID NO: 2, and/or a heavy chain CDR3 comprising the amino acid sequence of SEQ ID NO: 3; and/or comprising a light chain CDR1 comprising the amino acid sequence of SEQ ID NO: 4, and/or a light chain CDR2 comprising the amino acid sequence of SEQ ID NO: 5 and/or a light chain CDR3 comprising the amino acid sequence of SEQ ID NO: 6.

In some embodiments the antagonist antibody or fragment thereof that binds to human OX40 comprises an extended heavy chain CDR1 comprising the amino acid sequence of SEQ ID NO: 13, and/or an extended heavy chain CDR2 comprising the amino acid sequence of SEQ ID NO: 14, and/or an extended heavy chain CDR3 comprising the amino acid sequence of SEQ ID NO: 15; and/or comprises an extended light chain CDR1 comprising the amino acid sequence of SEQ ID NO: 16, and/or an extended light chain CDR2 comprising the amino acid sequence of SEQ ID NO: 17 and/or an extended light chain CDR3 comprising the amino acid sequence of SEQ ID NO: 18.

Preferably the antagonist antibody or fragment thereof that binds to human OX40 comprises a heavy chain CDR1 comprising the amino acid sequence of SEQ ID NO: 1, a heavy chain CDR2 comprising the amino acid sequence of SEQ ID NO: 2, and a heavy chain CDR3 comprising the amino acid sequence of SEQ ID NO: 3 and/or a light chain CDR1 comprising the amino acid sequence of SEQ ID NO: 4, a light chain CDR2 comprising the amino acid sequence of SEQ ID NO: 5 and a light chain CDR3 comprising the amino acid sequence of SEQ ID NO: 6. More preferably the antagonist antibody or fragment thereof that binds to human OX40 comprises a heavy chain CDR1 comprising the amino acid sequence of SEQ TD NO: 1, a heavy chain CDR2 comprising the amino acid sequence of SEQ ID NO: 2, and a heavy chain CDR3 comprising the amino acid sequence of SEQ ID NO: 3 and a light chain CDR1 comprising the amino acid sequence of SEQ ID NO: 4, a light chain CDR2 comprising the amino acid sequence of SEQ ID NO: 5 and a light chain CDR3 comprising the amino acid sequence of SEQ ID NO: 6.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka A et al., (2000) Br. J. Cancer, 83(2): 252-260 (describing the production of a humanized anti-CD30 antibody using only the heavy chain variable domain CDR3 of murine anti-CD30 antibody Ki-4); Beiboer S H et al., (2000) J. Mol. Biol. 296: 833-849 (describing recombinant epithelial glycoprotein-2 (EGP-2) antibodies using only the heavy chain CDR3 sequence of the parental murine MOC-31 anti-EGP-2 antibody); Rader C et al., (1998) Proc. Natl. Acad. Sci USA, 95: 8910-8915 (describing a panel of humanized anti-integrin αvβ3 antibodies using a heavy and light chain variable CDR3 domain of a murine anti-integrin αvβ3 antibody LM609 wherein each member antibody comprises a distinct sequence outside the CDR3 domain and capable of binding the same epitope as the parental murine antibody with affinities as high or higher than the parental murine antibody); Barbas C et al., (1994) J. Am. Chem. Soc. 116: 2161-62 (disclosing that the CDR3 domain provides the most significant contribution to antigen binding).

Accordingly, the present invention provides antibodies and fragments thereof that bind to human OX40 comprising one or more heavy and/or light chain CDR3 domains, in particular comprising heavy chain CDR3 comprising the amino acid sequence of SEQ ID NO: 3 and/or light chain CDR3 comprising the amino acid sequence of SEQ ID NO: 6, wherein the antibody is capable of binding to human OX40. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human e.g. murine antibody.

In a further aspect the present invention provides an antagonist antibody or fragment thereof that binds to human OX40 comprising a heavy chain variable region sequence comprising the amino acid sequence of SEQ ID NO: 7. In another aspect the present invention provides an antagonist antibody or fragment thereof that binds to human OX40 comprising a light chain variable region sequence comprising the amino acid sequence of SEQ ID NO: 8. In some embodiments the antagonist antibody or fragment thereof that binds to human OX40 comprises a heavy chain variable region sequence comprising the amino acid sequence of SEQ ID NO: 7 and a light chain variable region sequence comprising the amino acid sequence of SEQ ID NO: 8.

In another aspect the present invention provides variants of an antagonist antibody or fragment thereof that binds to human OX40. Thus the present invention provides antibodies or fragments thereof that have an amino acid sequence of the non-CDR regions of the heavy and/or light chain variable region sequence which is at least 80% identical (having at least 80% amino acid sequence identity) to the amino acid sequence of the non-CDR regions of the heavy and/or light chain variable region sequence of the parent antagonist antibody of either the heavy or the light chain e.g. of either the heavy and light variable region sequences as in SEQ ID NO: 7 or SEQ ID NO: 8, respectively. As well antibodies or fragments thereof that have an amino acid sequence of the non-extended CDR regions of the heavy and/or light chain variable region sequence which is at least 80% identical to the amino acid sequence of the non-extended CDR regions of the heavy and/or light chain variable region sequence of the parent antagonist antibody of either the heavy or the light chain are provided by the present invention. Preferably the amino acid sequence identity of the non-CDR regions or of the non-extended CDR regions of the heavy and/or light chain variable region sequence is at least 85%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to an amino acid sequence is defined herein as the percentage of amino acid residues in the candidate sequence that are identical with the antagonist antibody or fragment thereof that binds to human OX40, after aligning the sequences and introducing gaps, if necessary, to achieve the maximum percent sequence identity. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM250 (a standard scoring matrix; see Dayhoff M O et al., (1978) in Atlas of Protein Sequence and Structure, vol 5, supp. 3) can be used in conjunction with the computer program. For example, the percent identity can be calculated as: the total number of identical matches multiplied by 100 and then divided by the sum of the length of the longer sequence within the matched span and the number of gaps introduced into the longer sequences in order to align the two sequences.

In some embodiments the present disclosure thus provides an antagonistic antibody or fragment thereof that binds to human OX40, wherein the antibody or fragment thereof comprises a heavy chain variable framework region sequence which is at least 70% identical to the framework region sequence of SEQ ID NOS: 19, 20, 21, 22 or 23 and/or a light chain variable framework region sequence which is at least 60% identical to the framework region sequence of SEQ ID NOS: 24, 25, 26, 27 and 28. In some embodiments the present disclosure provides an antagonistic antibody or fragment thereof that binds to human OX40, wherein the antibody or fragment thereof comprises a heavy chain variable framework region sequence which is at least 74% identical to the framework region sequence of SEQ ID NO: 19 and/or a light chain variable framework region sequence which is at least 65% identical to the framework region sequence of SEQ ID NO: 24.

In another aspect the present invention provides an antagonistic antibody or fragment thereof that binds to human OX40 comprising the heavy and or light chain CDRs as described supra and further comprising a heavy chain variable framework region that is the product of or derived from a human gene selected from the group consisting of IGHV2-70*10 (SEQ ID NO: 19), IGHV2-70*01 (SEQ ID NO: 20), IGHV2-70*13 (SEQ ID NO: 21), IGHV2-5*09 (SEQ ID NO: 22), and IGHV2-70*11 (SEQ ID NO: 23), preferably a heavy chain variable framework region that is the product of or derived from human gene IGHV2-70*10 (SEQ ID NO: 19). The heavy chain variable framework region may comprise one or more (e.g., one, two, three and/or four) heavy chain framework region sequences (e.g., framework 1 (FW1), framework 2 (FW2), framework 3 (FW3) and/or framework 4 (FW4)) present in the product of or derived from those human genes. Preferably the heavy chain variable region framework comprises FW1, FW2 and/or FW3, more preferably FW1, FW2 and FW3 present in the product of or derived from a human gene selected from the group consisting of IGHV2-70*10 (SEQ ID NO: 19), IGHV2-70*01 (SEQ ID NO: 20), IGHV2-70*13 (SEQ ID NO: 21), IGHV2-5*09 (SEQ ID NO: 22), and IGHV2-70*11 (SEQ ID NO: 23). Heavy chain framework region sequences as used herein include FW1 (position 1 to position 25), FW2 (position 36 to position 49), FW3 (position 66 to position 94) and FW 4 (position 103 to position 113), wherein the amino acid position is indicated utilizing the numbering system set forth in Kabat.

In some embodiments the present disclosure provides an antibody or fragment thereof, wherein the antibody or fragment thereof comprises a heavy chain variable framework region that is the product of or derived from human gene IGHV2-70*10 (SEQ ID NO: 19) and wherein the heavy chain variable framework region comprises at least one amino acid modification from the corresponding heavy chain variable framework region of the corresponding murine antibody.

In some embodiments the present disclosure provides an antibody or fragment thereof comprising a heavy chain sequence comprising the amino acid sequence of SEQ ID NO: 32 and wherein the heavy chain variable framework region comprises at least one amino acid modification from the corresponding heavy chain variable framework region of the corresponding murine antibody.

Preferably the amino acid modification comprises an amino acid substitution at amino acid position selected from the group consisting of 23, 35b, 48, 50, 60, and 62, more preferably at amino acid positions selected from the group consisting of 23, 35b, 50, 60 and 62, most preferred at amino acid position 35b, wherein the amino acid position of each group member is indicated according to the Kabat numbering. Specifically the amino acid modification comprises an amino acid substitution selected from the group consisting of 23S, 35bG, 48L, 50H, 60N, and 62A, preferably an amino acid substitution selected from the group consisting of T23S, S35bG, I48L, R50H, S60N and S62A, whereas S35bG is the most preferred amino acid substitution wherein the amino acid position of each group member is indicated according to the Kabat numbering.

In another aspect the present invention provides an antagonistic antibody or fragment thereof that binds to human OX40 comprising a light chain variable framework region that is the product of or derived from a human gene selected from the group consisting of IGKV3-11*01 (SEQ ID NO: 24), IGKV1-39*01 (SEQ ID NO: 25), IGKV1D-39*01 (SEQ ID NO: 26), IGKV3-11*02 (SEQ ID NO: 27) and IGKV3-20*01 (SEQ ID NO: 28), preferably a light chain variable framework region that is the product of or derived from human gene IGKV3-11*01 (SEQ ID NO: 24). The light chain variable region framework region may comprise one or more (e.g., one, two, three and/or four) light chain framework region sequences (e.g., framework 1 (FW1), framework 2 (FW2), framework 3 (FW3) and/or framework 4 (FW4)) present in the product of or derived from those human genes. Preferably the light chain variable region framework comprises FW1, FW2 and/or FW3, more preferably FW1, FW2 and FW3 present in the product of or derived from a human gene selected from the group consisting of V3-11*01 (SEQ ID NO: 24), IGKV1-39*01 (SEQ ID NO: 25), IGKV1D-39*01 (SEQ ID NO: 26), IGKV3-11*02 (SEQ ID NO: 27) and IGKV3-20*01 (SEQ ID NO: 28). Light chain framework region sequences as used herein include FW1 (position 1 to position 23), FW2 (position 35 to position 49), FW3 (position 57 to position 88) and FW 4 (position 98 to position 1 08), wherein the amino acid position is indicated utilizing the numbering system set forth in Kabat.

In some embodiments the present disclosure provides an antibody or fragment thereof comprising a light chain variable framework region that is the product of or derived from human gene IGKV3-11*01 (SEQ ID NO: 24) and wherein the light chain variable framework region comprises at least one amino acid modification from the corresponding framework region of the light chain variable region of the corresponding murine antibody.

In some embodiments the present disclosure provides an antibody or fragment thereof comprising a light chain sequence comprising the amino acid sequence of SEQ ID NO: 39 and wherein the light chain variable framework region of the light chain sequence comprises at least one amino acid modification from the corresponding light chain variable framework region of the corresponding murine antibody.

Preferably the amino acid modification comprises an amino acid substitution at amino acid position selected from the group consisting of 1, 33, 34, 46, 47, 54, 56, and 71 and/or a deletion at amino acid position 31, more preferably an amino acid substitution at amino acid position selected from the group consisting of 33, 34, 46, 47, 54, 56, and 71 and/or a deletion at amino acid position 31, most preferably an amino acid substitution at amino acid position 46 and/or 47, wherein the amino acid position of each group member is indicated according to the Kabat numbering. Specifically the amino acid modification comprises an amino acid substitution selected from the group consisting of 1Q, 33M, 34H, 46P, 47W, 54L, 56S, and 71Y, and/or a deletion at T31, preferably an amino acid substitution selected from the group consisting of a 1Q, 33M, 34H, 46P, 47W, 54L, 56S and 71Y, more preferably an amino acid substitution selected from the group consisting of 33M, 34H, 46P, 47W and 71Y, whereas 46P, 47W are particularly preferred, wherein the amino acid position of each group member is indicated according to the Kabat numbering.

In some embodiments the antagonistic antibody or fragment thereof that binds to human OX40 comprises a heavy chain variable framework region that is the product of or derived from a human gene selected from the group consisting of V2-70*10 (SEQ ID NO: 19), V2-70*01 (SEQ ID NO: 20), V2-70*13 (SEQ ID NO: 21), V2-5*09 (SEQ ID NO: 22), and V2-70*11 (SEQ ID NO: 23) and a light chain variable framework region that is the product of or derived from a human gene selected from the group consisting of V3-11*01 (SEQ ID NO: 24), IGKV1-39*01 (SEQ ID NO: 25), IGKV1D-39*01 (SEQ ID NO: 26), IGKV3-11*02 (SEQ ID NO: 27) and IGKV3-20*01 (SEQ ID NO: 28), preferably a heavy chain variable framework region that is the product of or derived from human gene V2-70*10 (SEQ ID NO: 19), and a light chain variable framework region that is the product of or derived from human gene V3-11*01 (SEQ ID NO: 24). As well combinations of heavy chain variable framework regions which are present in the product of or derived from different human genes mentioned supra and/or of light chain variable region framework regions which are present in the product of or derived from different human genes mentioned supra are encompassed by the present invention.

Germline DNA sequences for human heavy and light chain variable region genes can be found in the "VBase" human germline sequence database (available on the Internet at www.mrccpe, cam.ac.uk/vbase), as well as in Kabat E A et al., supra; Tomlinson I M et al., (1992) J. Mol. Biol. 227: 776-798 and Cox J P L et al., (1994) Eur. J. Immunol. 24: 827-836. As another example, the germline DNA sequences for human heavy and light chain variable region genes can be found in the Genbank database.

In another aspect, the present disclosure also provides an antagonist antibody or fragment thereof that binds to human OX40, wherein at least one of the heavy chain CDRs and/or at least one of the light chain CDRs comprises at least one amino acid modification. Site-directed mutagenesis or PCR-mediated mutagenesis can be performed to introduce the modification(s) and the effect on antibody binding, or other functional property of interest, can be evaluated in in vitro or in vivo assays. Preferably conservative modifications are introduced. The modification(s) may be amino acid substitutions, additions or deletions, but are preferably substitutions. Typically, no more than five, preferably no more than four, more preferably no more than three, even more preferably no more than two, most preferably no more than one amino acid modifications are performed within a CDR region.

In certain embodiments, framework sequences can be used to engineer variable regions to produce variant antibodies. Variant antibodies of the invention include those in which modifications have been made to framework residues within VH and/or VK, e.g. to improve the properties of the antibody. Typically such framework modifications are made to decrease the immunogenicity of the antibody. For example, one approach is to "backmutate" one or more framework residues to the corresponding murine sequence or to "backmutate" one or more framework residues to a corresponding germline sequence.

Thus in a further aspect the present disclosure provides an antagonistic antibody or fragment thereof that binds to human OX40, wherein at least one of the framework region sequences of the heavy chain variable region of the humanized antibody or fragment thereof comprises at least one amino acid modification from the corresponding framework region of the heavy chain variable region of the corresponding murine antibody. Preferably the amino acid modification is an amino acid substitution. Typically, no more than six, preferably no more than five, preferably no more than four, more preferably no more than three, even more preferably no more than two, most preferably no more than one amino acid modifications are performed within a framework region. In some embodiments the present disclosure provides an antagonistic antibody or fragment thereof that binds to human OX40, wherein the amino acid modification of the framework regions of the heavy chain variable region comprise an amino acid substitution at amino acid position selected from the group consisting of 23, 35b, 48, 50, 60 and 62, and wherein the amino acid position of each group member is indicated according to the Kabat numbering. Preferred amino acid substitution of the framework regions of the heavy chain variable region are at amino acid positions selected from the group consisting of 23, 35b, 50, 60 and 62. More preferred amino acid substitutions of the framework regions of the heavy chain variable region are selected from the group consisting of 23S, 35bG, 48L, 50H, 60N and 62A, whereas 35bG is the most preferred amino acid substitution of the framework regions of the heavy chain variable region.

The present disclosure also provides an antagonistic antibody or fragment thereof that binds to human OX40, wherein at least one of the framework region sequences of the light chain variable region of the humanized antibody or fragment thereof comprises at least one amino acid modification from the corresponding framework region of the light chain variable region of the corresponding murine antibody. Preferably the amino acid modification is an amino acid substitution and/or an amino acid deletion. Typically, no more than six, preferably no more than five, preferably no more than four, more preferably no more than three, even more preferably no more than two, most preferably no more than one amino acid modifications are performed within a framework region. In some embodiments the present disclosure provides a humanized antibody or fragment thereof, wherein the amino acid modification of the framework regions of the light chain variable region sequence comprises an amino acid substitution at amino acid position selected from the group consisting of 1, 33, 34, 46, 47, 54, 56 and 71 and/or a deletion at amino acid position 31. More preferred amino acid modifications of the framework regions of the light chain variable region sequence comprise a deletion at Y31 and/or a substitution selected from the group consisting of a 1Q, 33M, 34H, 46P, 47W, 54L, 56S and 71Y, and wherein the amino acid position of each group member is indicated according to the Kabat numbering. Most preferred amino acid modifications of the framework regions of the light chain variable region sequence comprise a deletion at T31 and/or a substitution selected from the group consisting of 33M, 34H, 46P, 47W and 71Y, whereas 46P, and/or L47W are particularly preferred. In some embodiments the humanized antibody or fragment thereof of the present invention may comprise amino acid modifications of the framework regions of the heavy chain variable region sequence as set out above and amino acid modifications of the framework regions of the light chain variable region sequence as set out above.

The present disclosure also provides an antagonistic antibody or fragment thereof that binds to human OX40 that comprises a heavy chain variable region selected from the group consisting of SEQ ID NOS: 29, 58, 59, 77, 78, 79 and 80, preferably selected from the group consisting of SEQ ID NOS: 58, 59, 79 and 80 and more preferably from the group consisting of SEQ ID NOS: 58 and 59. The present disclosure also provides an antagonistic antibody or fragment thereof that binds to human OX40 that comprises a light chain variable region selected from the group consisting of SEQ ID NOS: 30, 60, 81, 82, 83, 84, 85, 86, 87, 88, and 89, preferably selected from the group consisting of SEQ ID NOS: 60, 86, 87 and 89, more preferably SEQ ID NO: 60. In some embodiments the antagonistic antibody or fragment thereof that binds to human OX40 comprises a heavy chain variable region selected from the group consisting of SEQ ID NOS: 29, 58, 59, 77, 78, 79 and 80, and a light chain variable region selected from the group consisting of SEQ ID NOS: 30, 60, 81, 82, 83, 84, 85, 86, 87, 88, and 89. Given that each of these heavy and light chain variable region sequences can bind to human OX40, the heavy and light chain variable region sequences can be "mixed and matched" to create anti-OX40 binding molecules of the invention. OX40 binding of such "mixed and matched" antibodies can be tested using the binding assays described e.g. in the Examples.

In some embodiments the antagonistic antibody or fragment thereof that binds to human OX40 comprises a heavy chain variable region selected from the group consisting of SEQ ID NOS: 58 and 59, and a light chain variable region selected from the group consisting of SEQ ID NOS: 60 and 89. In more preferred embodiments the antagonistic antibody or fragment thereof that binds to human OX40 comprises a heavy chain variable region comprising the amino acid sequence of SEQ ID NO: 58 and a light chain variable region comprising the amino acid sequence of SEQ ID NO: 60, a heavy chain variable region comprising the amino acid sequence of SEQ ID NO: 58 and a light chain variable region comprising the amino acid sequence of SEQ ID NO: 89, a heavy chain variable region comprising the amino acid sequence of SEQ ID NO: 59 and a light chain variable region comprising the amino acid sequence of SEQ ID NO: 60, or a heavy chain variable region comprising the amino acid sequence of SEQ ID NO: 59 and a light chain variable region comprising the amino acid sequence of SEQ ID NO: 89. Most preferred is an antagonistic antibody or fragment thereof that binds to human OX40 comprising a heavy chain variable region selected from the group consisting of SEQ ID NOS: 58 and 59, and a light chain variable region comprising the amino acid sequence of SEQ ID NO: 60.

The present disclosure also provides an antagonistic antibody or fragment thereof that binds to human OX40 that comprises a heavy chain sequence selected from the group consisting of SEQ ID NOS: 32, 33, 34, 35, 36, 37 and 38, preferably selected from the group consisting of SEQ ID NOS: 35, 36, 37 and 38 and more preferably from the group consisting of SEQ ID NOS: 37 and 38. The present disclosure also provides an antagonistic antibody or fragment thereof that binds to human OX40 that comprises a light chain sequence selected from the group consisting of SEQ ID NOS: 39, 40, 41, 42, 43, 44, 45, 46, 47, 48 and 49, preferably selected from the group consisting of SEQ ID NOS: 45, 46, 47 and 49, more preferably SEQ ID NO: 47. In some embodiments the antagonistic antibody or fragment thereof that binds to human OX40 comprises a heavy chain sequence selected from the group consisting of SEQ ID NOS: 32, 33, 34, 35, 36, 37 and 38, and a light chain sequence selected from the group consisting of SEQ ID NOS: 39, 40, 41, 42, 43, 44, 45, 46, 47, 48 and 49. Given that each of these heavy and light chain variable region sequences can bind to human OX40, the heavy and light chain variable region sequences can be "mixed and matched" to create anti-OX40 binding molecules of the invention. OX40 binding of such "mixed and matched" antibodies can be tested using the binding assays described e.g. in the Examples.

In some embodiments the antagonistic antibody or fragment thereof that binds to human OX40 comprises a heavy chain sequence selected from the group consisting of SEQ ID NOS: 37 and 38, and a light chain sequence selected from the group consisting of SEQ ID NOS: 47 and 49. In more preferred embodiments the antagonistic antibody or fragment thereof that binds to human OX40 comprises a heavy chain sequence comprising the amino acid sequence of SEQ ID NO: 37 and a light chain sequence comprising the amino acid sequence of SEQ ID NO: 47, a heavy chain sequence comprising the amino acid sequence of SEQ ID NO: 37 and a light chain sequence comprising the amino acid sequence of SEQ ID NO: 49, a heavy chain sequence comprising the amino acid sequence of SEQ ID NO: 38 and a light chain sequence comprising the amino acid sequence of SEQ ID NO: 47, or a heavy chain sequence comprising the amino acid sequence of SEQ ID NO: 38 and a light chain sequence comprising the amino acid sequence of SEQ ID NO: 49. Most preferred is an antagonistic antibody or fragment thereof that binds to human OX40 comprising a heavy chain sequence selected from the group consisting of SEQ ID NOS: 37 and 38, and a light chain sequence comprising the amino acid sequence of SEQ ID NO: 47.

In one embodiment of the present disclosure, the antagonist antibody or fragment thereof is a murine antibody, chimeric antibody or a humanized antibody, preferably a humanized antibody, more preferably a monoclonal murine antibody, a monoclonal chimeric antibody or a monoclonal humanized antibody.

The present disclosure also provides a monovalent antibody or fragment thereof that binds to human OX40, i.e. an antibody which consists of a single antigen binding arm. The present disclosure also provides a fragment of a antibody that binds to human OX40 selected from the group consisting of Fab, Fab', Fab'-SH, Fd, Fv, dAb, F(ab')2, scFv, bispecific single chain Fv dimers, diabodies, triabodies and scFv genetically fused to the same or a different antibody. Preferred fragments are scFv, bispecific single chain Fv dimers and diabodies. The present disclosure also provides a full length antibody that binds to human OX40.

The present disclosure also provides an antibody or fragment thereof that binds to human OX40 which further comprises a heavy and/or light constant region in particular a human heavy and/or a human light constant region. Human heavy constant regions may be selected from the group of human immunoglobulins consisting of IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), or IgE (IGHE), whereas the human heavy constant region IgG, in particular IgG1 (IGHG1) is preferred. Human light constant region may be selected from the group of human immunoglobulins consisting of kappa or lambda constant regions, whereas human kappa constant region is preferred. In a preferred embodiment the antagonistic antibody or fragment thereof that binds to human OX40 comprises a human IgG1 (IGHG1) heavy constant domain and a human light kappa constant domain.

In addition or alternative to modifications made within the framework regions or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation. Each of these embodiments is described in further detail below. Modifications within the Fc region as outlined below are according to the EU numbering of residues in the Fc region. In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al. In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In a further embodiment Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in farther detail in U.S. Pat. Nos. 5,624,821 and 5,648,260, both by Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 to 238 in the N-terminal region of the CH2 domain are altered to thereby alter the ability of the antibody to fix complement. This approach is described further in PCT Publication WO94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO00/42072 by Presta.

The present disclosure also provides an antagonistic antibody or fragment thereof that binds to human OX40 comprising human heavy and/or light constant regions, wherein the human heavy constant region comprises an isotypic variant comprising the CH1 region, the hinge region, the CH2 region and CH3 region from human IgG4 (IGHG4) and wherein the hinge region comprises a substitution of serine at position 228 to proline. Preferably the humanized antibody comprising the isotypic variant is a full length antibody. A particular preferred humanized antibody or fragment thereof that binds to human OX40 comprising an isotypic variant comprising the CH1 from human IgG4 (IGHG4), the hinge from human IgG4 (IGHG4), having S228P substitution and the CH2 and CH3 from human IgG4 (IGHG4) comprises a heavy chain sequence comprising the amino acid sequence of SEQ ID NO: 57 and a light chain sequence comprising the amino acid sequence of SEQ ID NO: 47. It has been found that the isotypic variant exhibits no Fc-mediated cytotoxicity mechanisms such as ADCC compared to an antagonistic antibody or fragment thereof that binds to human OX40 which comprises a human heavy constant region from human IgG1 (IGHG1) (which is usually a native human IgG1), i.e. as compared to an antagonistic antibody or fragment thereof that binds to human OX40 that only differs from the isotypic variant with regard to the modified heavy constant region.

The present disclosure also provides an antagonistic antibody or fragment thereof that binds to human OX40 which comprises a human IgG Fc region, wherein the mature core carbohydrate structure attached to the human IgG Fc region lacks fucose (referred herein alternatively as "non fucosylated"). Preferably the antibody comprises a human IgG1 (IGHG1) Fc region, wherein the mature core carbohydrate structure attached to the human IgG1 (IGHG1) Fc region lacks fucose. More preferred is a full-length antibody comprising a human IgG1 (IGHG1) Fc region, wherein the mature core carbohydrate structure attached to the human IgG1 (IGHG1) Fc region lacks fucose. It is known from WO03/035835 that lack of fucose in the mature core carbohydrate structure attached to the human IgG Fc region may enhance ADCC. Thus in a further embodiment the antagonistic antibody or fragment thereof of the present disclosure comprises a human IgG1 (IGHG1) Fc region, wherein the mature core carbohydrate structure attached to the human IgG1 (IGHG1) Fc region lacks fucose, whereas the antibody lacking fucose exhibits enhanced ADCC compared to the parent humanized antibody or fragment thereof not lacking fucose. Methods to generate antibodies which lack fucose are, for example (a) use of an engineered or mutant host cell that is deficient in fucose metabolism such that it has a reduced ability (or is unable to) fucosylate proteins expressed therein; (b) culturing cells under conditions which prevent or reduce fucosylation; (c) post-translational removal of fucose (e.g. with a fucosidase enzyme); (d) post-translational addition of the desired carbohydrate, e.g. after recombinant expression of a non-glycosylated glycoprotein; or (e) purification of the glycoprotein so as to select for product which is not fucosylated. Preferably used are methods described in Example 14 of WO10/095031 e.g. methods described in Longmore et al., (1982) Carbohydr. Res. 365-92 or in Imai-Nishiya et al., (2007), BMC Biotechnol. 7: 84.

Also provided by the present invention is an antagonist antibody or fragment thereof that binds to human OX40 and which binds to the same epitope as the antibody comprising the heavy chain variable sequence comprising the amino acid sequence of SEQ ID NO. 7 and/or the light chain variable sequence comprising the amino acid sequence of SEQ ID NO. 8. Also provided by the present invention is a specific region or epitope of human OX40, in particular of the human OX40 receptor extracellular domain, which is bound by an antibody provided by the present invention, in particular by an antibody comprising the heavy chain variable sequence comprising the amino acid sequence of SEQ ID NO. 7 and/or the light chain variable sequence comprising the amino acid sequence of SEQ ID NO. 8. This specific region or epitope of the human OX40 polypeptide can be identified by any suitable epitope mapping method known in the art in combination with any one of the antibodies provided by the present invention. Examples of such methods include screening peptides of varying lengths derived from OX40 for binding to the antibody of the present invention with the smallest fragment that can specifically bind to the antibody containing the sequence of the epitope recognised by the antibody. The OX40 peptides may be produced synthetically or by proteolytic digestion of the OX40 polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antagonist antibodies which bind the same epitope.

Anti-OX40 Antibody Properties

Standard assays to evaluate the binding ability of the antibodies toward e.g. human OX40 are known in the art, including for example, ELISAs, BIAcore®, Western blots, RIAs, and flow cytometry analysis. Suitable assays are described in detail in the Examples. The binding kinetics (e.g., binding affinity like KD) of the antibodies also can be assessed by standard assays known in the art, such as by Scatchard or BIAcore® system analysis. The relative binding affinity $K_i$ can be assessed by standard competition assays known in the art.

In a further aspect the present invention provides antagonistic antibodies or fragment thereof that bind to human OX40 and which block a Human Mixed Lymphocyte Reaction (MLR) in a dose dependent manner to a higher degree than recombinant humanized antibody efalizumab. Recombinant humanized antibody efalizumab binds to the CD11a subunit of lymphocyte function-associated antigen 1. MLR can be carried out and measured according to Example 3.

Figure 3:
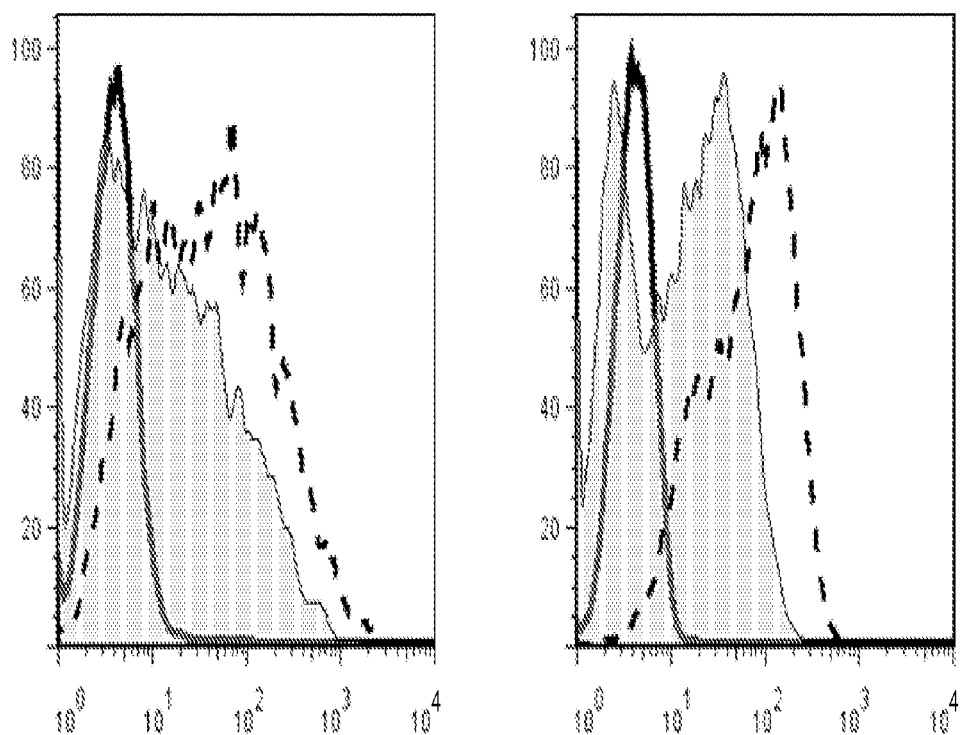
FIG. 3: Flow cytometry analysis of chimeric 1D4 antibody
  (A) Staining on human activated peripheral blood mononuclear cells (PBMCs) and HPB-ALL cells. Histogram plots show the fluorescence intensity (X-axis) and relative cell number (% of max events—Y-Axis). The type of cells stained is indicated. Human PBMC were activated with PHA and IL-2 for 48h prior measurements.
  (B) Staining on activated cynomologus monkey PBMCs. Binding of the chimeric 1D4 antibody to cynomologus OX40 was evaluated by flow cytometry. Peripheral blood mononuclear cells (PBMCs) were isolated from whole blood collected from a cynomologus monkey and 3×10$^6$ cells were cultured for 50 hours in the presence of 10 mg/ml of PHA and 100U/ml of rhuIL-2. Activated PBMCs were incubated with 25 mg/ml of either control antibody (upper profile (i)) or biotinylated sheep anti-human OX40 antibody (middle profile (ii)) or biotinylated chimeric 1D4 antibody (lower profile (iii)). Binding of each antibody to cynomologus OX40 was detected with streptavidin-APC.
Figure 4A:
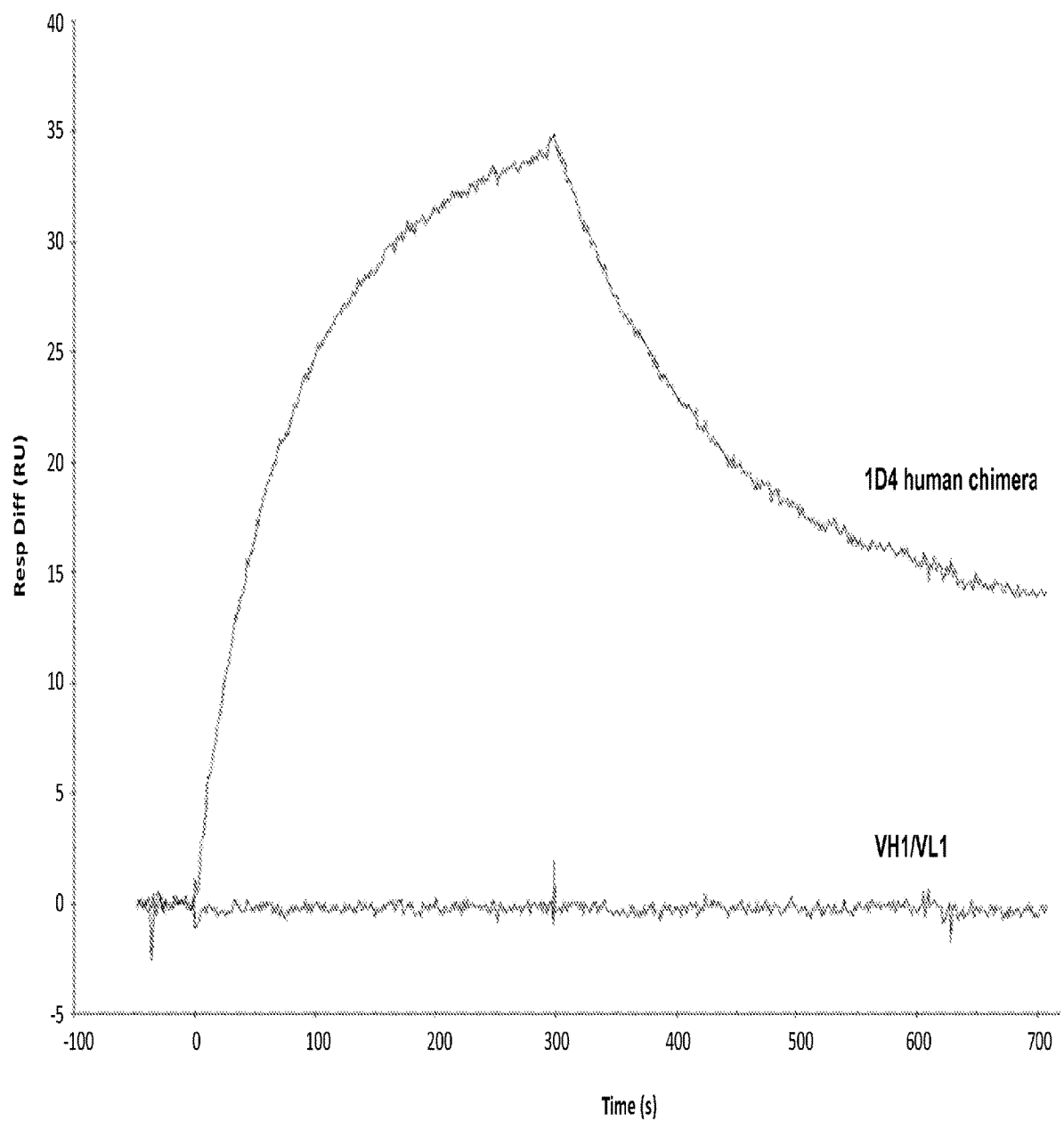
Figure 4B:
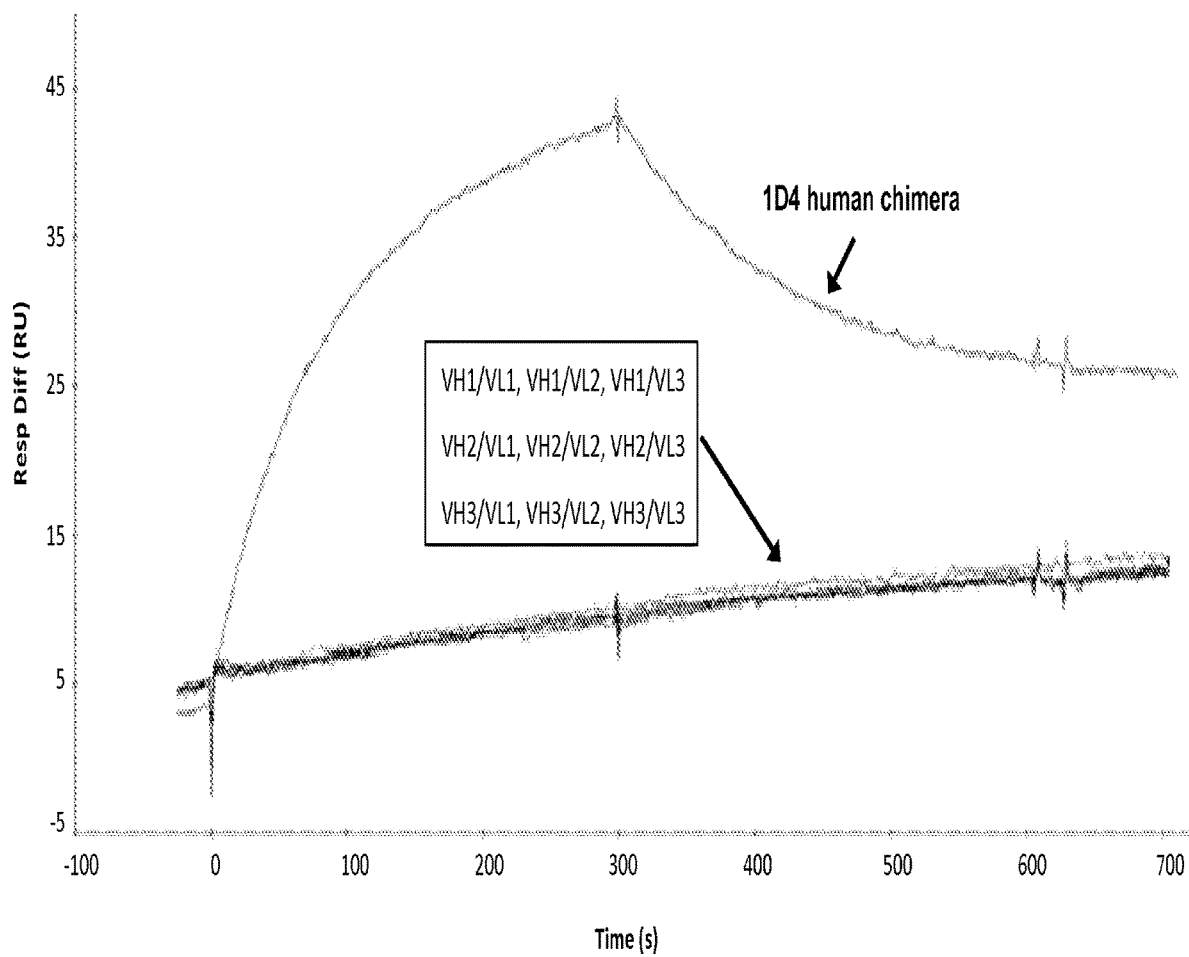
Figure 4D:
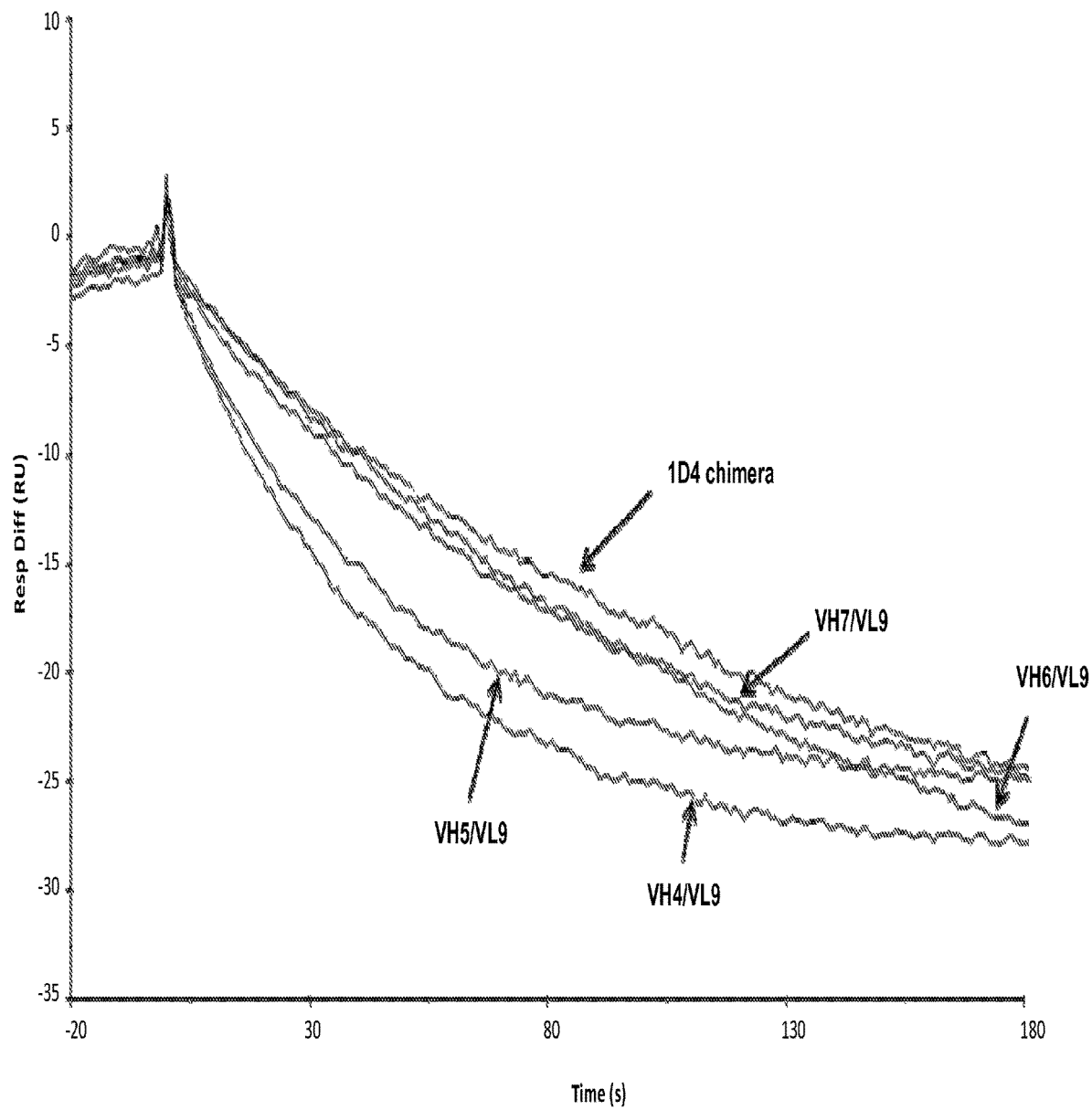
Figure 4E:
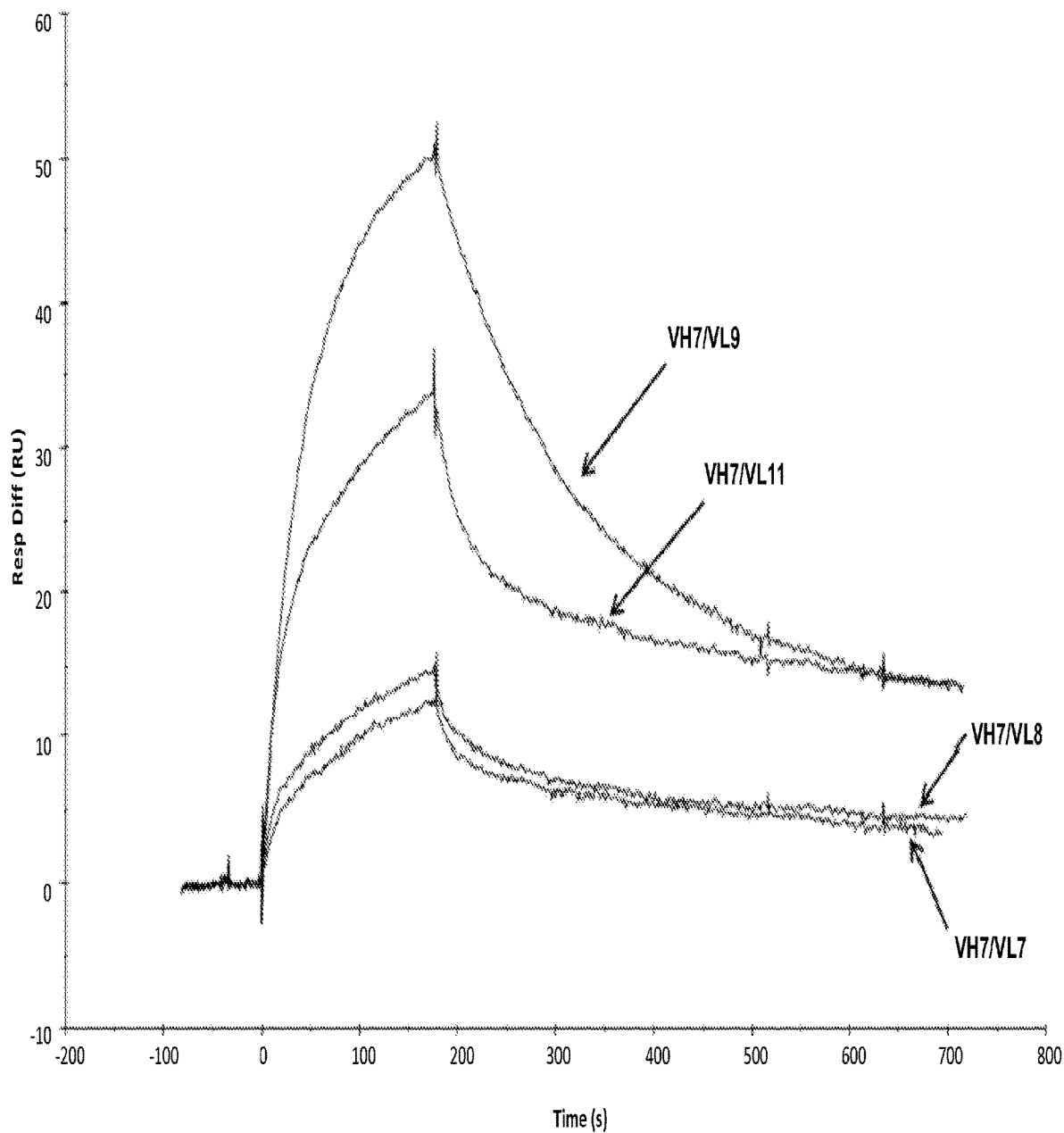
Figure 4F:
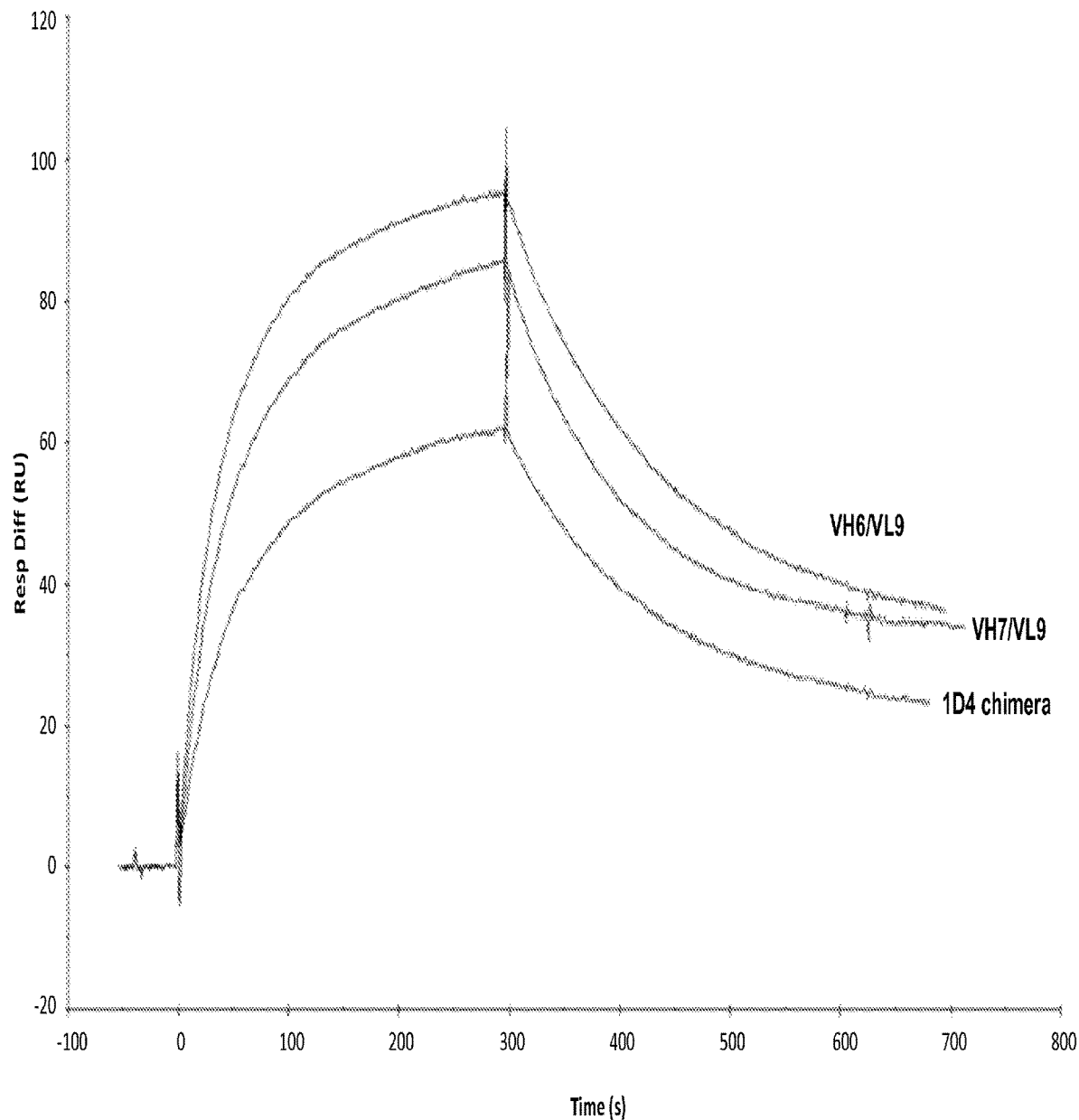

In a further aspect the present invention provides antagonist antibodies or fragment thereof that bind to human OX40 and which are also able to recognise cynomolgus monkey OX40. Binding of an antagonistic anti-OX40 antibody to both human and cynomolgus peripheral blood mononuclear cells (PBMC) can be carried out and measured according to Example 4 and shown in FIG. 3. The antibody was found to recognise OX40 expressed on the surface of human and cynomolgus monkey activated lymphocytes indicating that this antibody has cross-reactive properties.

In a further aspect the present invention provides antagonistic antibodies or fragment thereof that bind to human OX40, in particular human OX40 in isolated form, with an affinity ($K_D$) of 500 nM or less, preferably 200 nM or less, more preferably 150 nM or less, more preferably 120 nM or less, even more preferably 110 nM or less e.g. measured by Surface Plasmon Resonance (SPR) on a BIAcore® instrument (GE Healthcare Europe GmbH, Glattbrugg, Switzerland) by capturing the antibody on a protein-A coupled CM5 research grade sensor chip (GE Healthcare Europe GmbH, Glattbrugg, Switzerland; BR-1000-14) with a recombinant monovalent human OX40 receptor extracellular domain (SEQ ID NO: 11) used as analyte as detailed in Examples 5 and 6 and as illustrated in FIG. 4. "Monovalent" as used herein in relation to affinity measurements using OX40 receptor refers to a human OX40 receptor domain, like the extracellular domain, not artificially dimerized or multimerized as it would be e.g. if the domain would be amino-terminally fused to an immunoglobulin Fc portion. In a preferred aspect, the present invention provides a humanized antibody or fragment thereof that retains at least 75% of the OX40 binding affinity ($K_D$) of the corresponding chimeric antibody. Preferably, the humanized antibody or fragment thereof binds human OX40 with equivalent affinity to the corresponding chimeric antibody. By "equivalent affinity" is meant an affinity value that is within a range of ±10% of the OX40 binding affinity of the corresponding chimeric antibody. More preferably, the present invention provides a humanized antibody or fragment thereof that binds human OX40 with a higher affinity than the corresponding chimeric antibody. In a preferred aspect of the present invention, antagonistic antibodies or fragment thereof that bind to human OX40 are provided that have a binding affinity ($K_D$) of 110 nM or less, preferably 100 nM or less, more preferably 90 nM or less, more preferably 80 nM or less, even more preferably 70 nM or less e.g. measured by Surface Plasmon Resonance (SPR) on a BIAcore® instrument (GE Healthcare Europe GmbH, Glattbrugg, Switzerland) by capturing the antibody on a protein-A coupled CM5 research grade sensor chip (GE Healthcare Europe GmbH, Glattbrugg, Switzerland; BR-1000-14) with a recombinant monovalent human OX40 receptor extracellular domain (SEQ ID NO: 11) used as analyte as detailed in Examples 5 and 6 and as illustrated in FIG. 4.

Figure 6:
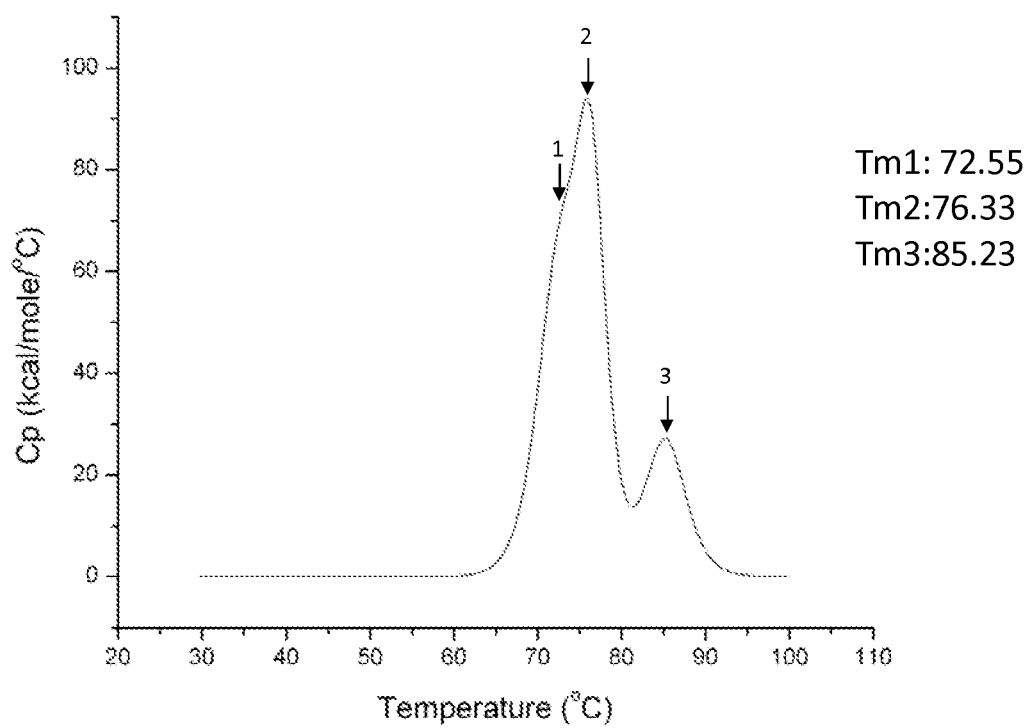
FIG. 6: Thermostability measurements of humanized anti-OX40 anti-antibody VH6/VL9 FAB fragment using differential scanning calorimetry. Data are expressed as excess molar heat capacity (abbreviated Cp [kcal/mol/° C.]; Y axis) vs. temperature (X axis).

A further aspect of the present invention provides antagonistic antibodies or fragments thereof that bind to human OX40 and which have good thermal stability. In a preferred embodiment, an antagonistic humanized antibody or fragment thereof that binds to human OX40 has a FAB fragment thermostability temperature greater than 70° C., preferably greater than 75° C., more preferably greater than 80° C. and even more preferably greater than 85° C. For analysis of FAB fragment thermostability differential scanning calorimetry measurements are used, whereas a mid-point melting temperature of the FAB fragment in context of a full-length IgG is identified. These kind of calorimetric measurements are known to the skilled person and can be carried out according to e.g. Garber & Demarest (2007), BBRC, 355: 751-7, as further described in Example 6 and shown in FIG. 6.

In a further aspect the present invention describes antagonistic antibodies or fragments thereof that bind to an epitope on the human OX40 extracellular region. As described in Example 7 and shown in FIG. 7, one or more of the four domains of the OX40 extracellular region were exchanged between human and rat sequences and Fc fusion proteins generated. A binding ELISA was then performed to test the reactivity of an antagonistic humanised antibody on the human OX40 extracellular region, rat OX40 extracellular region and four human-rat chimeric proteins. Thus the present invention provides an antagonistic antibody or fragment thereof which maps within the second domain of human OX40 extracellular region.

The present invention also provides antagonistic antibodies or fragments thereof which can be used to suppress immune reactions. The effect of an antagonistic humanized anti-OX40 antibody was tested in a MLR (see Example 8) used as an in vitro model of alloreactive T cell activation and proliferation (O'Flaherty E et al., (2000) Immunology, 100 (3): 289-99; DuPont B & Hansen J A (1976) Adv. Immunol. 23: 107-202). PBMCs from two unrelated donors were mixed, resulting in the activation of T cells and a proliferation of T lymphocytes. In addition, three different formats of the antagonistic humanized anti-OX40 antibody were tested in this assay: an IgG1 (IGHG1) format, a non fucosylated IgG1 (IGHG1) format and an IgG4 (IGHG4) format, to further determine the contribution of cytotoxic mechanisms such as ADCC on the inhibition of MLR. The antagonistic humanized anti-OX40 antibody efficiently inhibited MLR in two different individuals (responders) with EC50 values of approximately 100 ng/mL. However the results showed a difference depending on the format of the antibody used. In the first individual (responder 1), T cell reactivity was efficiently inhibited by the IgG1 (IGHG1) and IgG4 (IGHG4) antibody formats indicating that the cytotoxic mechanisms are not critical for this individual. For the second individual (responder 2) the IgG1 (IGHG1) format achieved more than 60% inhibition, whereas the IgG4 (IGHG4) format only poorly blocked the MLR. In both individuals, the non fucosylated IgG1 (IGHG1) format was very effective at inhibiting MLR. These results indicate that blocking OX40 activation may be sufficient in some individuals to inhibit MLR but this effect can be greatly enhanced by additional cytotoxic mechanisms. Therefore for the treatment of patients suffering from OX40 mediated disorders, where the disorder appears to be independent of the patients' OX40 costimulatory status e.g. patients with low OX40 expression levels, administration of an antagonistic antibody or fragment thereof that binds human OX40 and which has enhanced cytotoxic mechanisms may be particularly effective. A preferred embodiment of the present invention provides an antagonistic humanized antibody that binds to human OX40 for the treatment of a patient suffering from an OX40 mediated disorder. Furthermore, the patient may have low expression levels of OX40. Preferably the antagonistic humanized antibody that binds to human OX40 comprises an IgG1 (IGHG1) region. More preferably the antagonistic humanized antibody that binds to human OX40 comprises a non fucosylated IgG1 region.

In a further aspect of the present invention, the effect of an antagonistic antibody or fragment thereof was demonstrated in a xenogeneic graft versus host reaction, in which SCID mice were reconstituted with human PBMCs. This reaction provides a model for the allogenic graft versus host disease (GVHD) observed after bone marrow transplant in human patients. In this model, human PBMCs and T lymphocytes in particular, launch a strong response against the mouse host cells which gives rise to severe inflammatory symptoms. As described in Example 9 and shown in FIG. 9 and Table 10, an antagonistic humanized antibody that binds to human OX40 potently suppressed the GVHD reaction at a dose of 1 mg/kg. Surprisingly, this antibody demonstrated a better efficacy than Enbrel®, a recognised therapy for GVHD (Xhaard A et al., (2011) Bull. Cancer, 98(8): 889-99; Simpson D (2001) Expert Opin. Pharmacother. 2(7): 1109-17). Therefore, in a preferred embodiment, the present invention provides an antagonistic antibody or fragment thereof that binds to human OX40 and which is effective in the treatment of GVHD. Preferably, administration of the antibody to a subject results in a four-fold improvement in survival median (days) compared to the administration of vehicle. More preferably, administration of the antibody to subject results in a two-fold improvement in survival median (days) compared to the administration of Enbrel®. The present invention therefore provides an antagonistic antibody or fragment therefore that binds to human OX40 that is more effective than Enbrel® in treating a patient with GVHD and/or at suppressing GVHD. In addition, it has been reported that agonistic anti-OX40 binding antibodies worsen GVHD in allogenic mouse GVHD models (Valzasina B et al., (2005) Blood, 105(7): 2845-51; Blazar B R et al., (2003) Blood, 101(9): 3741-8), therefore it can be concluded from Example 9, that antagonistic antibodies and fragments thereof of the present invention show no agonistic effects on binding human OX40, since no worsening of the GVHD was observed in the model. Therefore, the present invention provides a humanized antibody or fragment therefore that binds to human OX40 that does not show agonistic activity on binding.

Nucleic Acids, Vectors and Host Cells

The present disclosure also provides isolated nucleic acids encoding the antibodies and fragments thereof that bind to human OX40, vectors and host cells comprising the nucleic acid or the vector. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art, see e.g. F. Ausubel, et al., ed. (1987) Current Protocols in Molecular Biology, Greene Publishing and Wiley Interscience, New York. A nucleic acid of the invention can be, for example, DNA or RNA and may or may not contain intron sequences. In a preferred embodiment, the nucleic acid is a cDNA molecule.

Nucleic acids of the invention can be obtained using standard molecular biology techniques e.g. cDNAs encoding the light and heavy chains of the antibody or encoding VH and VL segments can be obtained by standard PCR amplification or cDNA cloning techniques. For antibodies obtained from an immunoglobulin gene library (e.g., using phage display techniques), one or more nucleic acids encoding the antibody can be recovered from the library. The methods of introducing exogenous nucleic acid into host cells are well known in the art, and will vary with the host cell used. Techniques include but are not limited to dextran-mediated transfection, calcium phosphate precipitation, calcium chloride treatment, polyethylenimine mediated transfection, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

Preferred nucleic acids molecules of the invention are those encoding the heavy chain sequence selected from the group consisting of SEQ ID NOS: 32, 33, 34, 35, 36, 37 and 38 and/or the light chain sequence selected from the group consisting of SEQ ID NOS: 39, 40, 41, 42, 43, 44, 45, 46, 47, 48 and 49. Preferred nucleic acids molecules of the invention are those encoding the heavy chain variable region selected from the group consisting of SEQ ID NOS: 29, 58, 59, 77, 78, 79 and 80 and/or the light chain variable region selected from the group consisting of SEQ ID NOS: 30, 60, 81, 82, 83, 84, 85, 86, 87, 88, and 89.

Preferred nucleic acids molecules of the invention are those encoding the light chain variable region of SEQ ID NO: 8 and/or the heavy chain variable region of SEQ ID NO: 7, e.g. DNA encoding the heavy chain variable region comprising the nucleic acid sequence of SEQ ID NO: 9 and/or DNA encoding the light chain variable region comprising the nucleic acid sequence of SEQ ID NO: 10. More preferred nucleic acid molecules of the invention are those encoding the heavy chain variable region of SEQ ID NOS: 58 or 59 and/or the light chain variable region of SEQ ID NO: 60, e.g. DNA encoding the heavy chain variable region comprising the nucleic acid sequence of SEQ ID NOS: 61 or 62 and/or DNA encoding the light chain variable region comprising the nucleic acid sequence of SEQ ID NO: 63, which are most preferred.

Once DNA fragments encoding VH and VL segments are obtained, these DNA fragments can be further manipulated by standard recombinant DNA techniques, for example to convert the variable region genes to full-length antibody chain genes, or to fragments genes corresponding to the fragments described supra like Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat E A et al., supra) and DNA fragments encompassing these regions can be obtained by standard PCR amplification. The heavy chain constant region can be an IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), or IgE (IGHE) constant region, but most preferably is an IgG1 (IGHG1) constant region. For a Fab fragment heavy chain gene, the VH-encoding DNA can be operatively linked to another DNA molecule encoding only the heavy chain CH1 constant region. The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat E A et al., supra.) and DNA fragments encompassing these regions can be obtained by standard PCR amplification. In preferred embodiments, the light chain constant region can be a kappa or lambda constant region, preferably a kappa constant region. To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird R E et al., (1988) Science, 242: 423-426; Huston J S et al., (1988) Proc. Natl. Acad. Sci. USA, 85: 5879-83; McCafferty J et al., (1990) Nature, 348: 552-554). Various techniques have been developed for the production of antibody fragments of antibodies. Traditionally, these fragments were derived via proteolytic digestion of intact antibodies (see, e.g., Morimoto K et al., (1992) J. Biochem. & Biophysical Methods, 24: 107-117 and Brennan M et al., (1985) Science, 229: 81-3). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter P et al., (1992) Bio/Technology, 10: 163-167). According to another approach, F(ab')2 fragments can be isolated directly from recombinant host cell culture. Other techniques for the production of antibody fragments will be apparent to the skilled practitioner. In other embodiments, the antibody of choice is a single-chain Fv fragment (scFv), see eg WO 1993/16185; U.S. Pat. Nos. 5,571,894 and 5,587,458. The antibody fragment may also be a "linear antibody", e.g., as described in U.S. Pat. No. 5,641,870, for example.

The nucleic acids that encode the antibodies of the present invention may be incorporated into a vector, preferably an expression vector in order to express the protein. A variety of expression vectors may be utilized for protein expression. Expression vectors may comprise self-replicating extrachromosomal vectors or vectors which integrate into a host genome. Expression vectors are constructed to be compatible with the host cell type. Thus vectors, preferably expression vectors, which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology, Methods in Enzymology 185, Academic Press, San Diego, CA (1990)). Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

Suitable host cells for cloning or expressing the DNA in the vectors herein are prokaryote, yeast, or higher eukaryote cells. Suitable prokaryotes for this purpose include eubacteria, including gram-negative or gram-positive organisms, for example, Enterobacteriaceae such as *Escherichia*, e.g., *E. coli*, *Enterobacter*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*. Suitable *E. coli* cloning hosts include *E. coli* 294 (ATCC 31,446), *E. coli* B, *E. coli* X1776 (ATCC 31,537), and *E. coli* W3110 (ATCC 27,325). In addition to prokaryotes, eukaryotic microbes such as filamentous fungi or yeast are suitable cloning or expression hosts. *Saccharomyces cerevisiae*, or common baker's yeast, is the most commonly used among lower eukaryotic host microorganisms. However, a number of other genera, species, and strains are commonly available and useful, such as *Schizosaccharoriyces pombe*; *Kluyveromyces* hosts including *K. lactis*, *K. fragilis* (ATCC 12,424), *K. bulgaricus* (ATCC 16,045), *K. wickeramii* (ATCC 24,178), K. WaltH (AJCC 56,500), *K. drosopmarum* (ATCC 36,906), *K. thermotolerans*, or *K. marxianusyarrowia* (EP402226); *Pichia pastoris* (EP183070); *Candida*; *Trichoderma reesia* (EP244234); *Neurospora crassa*; *Schwanniomyces* such as *Schwanniomyces occidentalis*; and filamentous fungi including *Neurospora*, *Penicillium*, *Tolypocladium*, or *Aspergillus* hosts such as *A. nidulans* or *A. niger*.

Suitable host cells for the expression of the antibodies of the invention are derived from multicellular organisms. Examples of invertebrate cells include plaril and insect cells. Numerous baculoviral strains and variants and corresponding permissive insect host cells from hosts such as *Spodoptera frugiperda* (caterpillar), *Aedes augypti* (mosquito), *Aedes albopictus* (mosquito), *Drosophila melanogaster* (fruitfly) and *Bombyx mori* have been identified. A variety of viral strains for transfection are publicly available, for example, the L-1 variant of *Autographa californica* NPV and the Bm-5 strain of *Bombyx mori* NPV, and such viruses may be used, particularly for transfection of *Spodoptera frugiperda* cells. Plant cell cultures of cotton, corn, potato, soybean, *petunia*, tomato, and tobacco can also be utilized as hosts.

Host cells for expressing the recombinant antibodies of the invention are preferably mammalian host cells which include Chinese Hamster Ovary (CHO cells) (including dhfr⁻ CHO cells, described in Urlaub G & Chasin L A (1980) Proc. Natl. Acad. Sci, USA, 77: 4216-4220, used with a DHFR selectable marker, e.g., as described in Kaufman R J & Sharp P A (1982) J. Mol. Biol, 159: 601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP338841 (to Bebbington). When recombinant antibody genes are introduced into mammalian host cells, the antibodies are produced by culturing the host cells for a period of time sufficient to allow for expression of the antibody in the host cells or, more preferably, for secretion of the antibody into the culture medium in which the host cells are grown. Host cells useful for producing antibodies that bind to human OX40 may be cultured in a variety of media. Commercially available media such as Ham's F10 (Sigma-Aldrich Chemie GmbH, Buchs, Switzerland), Minimal Essential Medium (MEM; Sigma-Aldrich Chemie GmbH), RPMI-1640 (Sigma-Aldrich Chemie GmbH, Basel, Switzerland), and Dulbecco's Modified Eagle's Medium ((DMEM; Sigma-Aldrich Chemie GmbH) are suitable for culturing the host cells. Antibodies can be recovered from the culture medium using standard protein purification methods.

Antibodies may be operably linked to a fusion partner to enable targeting of the expressed protein, purification, screening, display, and the like. Fusion partners may be linked to the antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs antibody and any associated fusion partners to a desired cellular location or to the extracellular media. As is known in the art, certain signalling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both.

Construction and Production of Antibodies

Antibodies generated against the OX40 polypeptide may be obtained by immunisation of an animal i.e. by administering the polypeptides to an animal, preferably a non-human animal, using well-known and routine protocols, see for example Handbook of Experimental Immunology (Weir D M (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats in particular mice are generally most suitable. Antibodies can be produced as well by recombinant DNA techniques known to the skilled person. In additional antibodies can be produced by enzymatic or chemical cleavage of naturally occurring antibodies. Humanized antibodies of the present invention may be constructed by transferring one or more CDRs or portions thereof from VH and/or VL regions from a non-human animal (e.g., mouse) to one or more framework regions from human VH and/or VL regions. Optionally, human framework residues thus present in the VH and/or VL regions may be replaced by corresponding non-human (e.g., mouse) residues when needed or desired for decreasing immunogenicity of the antibody and/or maintaining binding affinity. Optionally, non-human amino acid residues present in the CDRs may be replaced with human residues. Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al).

Humanized antibodies of the present invention may be constructed wherein the human acceptor molecule for the heavy chain variable region is selected based on homology considerations between potential acceptor molecule variable regions and the heavy chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same heavy chain class as the murine donor molecule, and of the same canonical structural class of the variable region of the murine donor molecule. Secondary considerations for selection of the human acceptor molecule for the heavy chain variable region elude homology in CDR length between the murine donor molecule and the human acceptor molecule. Human acceptor antibody molecules are preferably selected by homology search to the V-BASE database, although other databases such as the Kabat and the public NCBI databases may be used as well.

Humanized antibodies of the present invention may be constructed wherein the human acceptor molecule for the light chain variable region is selected based on homology considerations between potential acceptor molecule variable regions and with the light chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same light chain class as the murine donor molecule, and of the same canonical structural class of the variable region of the murine donor molecule. Secondary considerations for selection of the human acceptor molecule for the light chain variable region include homology in CDR length between the murine donor molecule and the human acceptor molecule. Human acceptor antibody molecules are preferably selected by homology searches to the V-BASE database, and other databases such as the Kabat and the public NCBI databases may be used as well. Methods for humanizing a nonhuman antibody are described herein, including in Example 6, below.

The present invention provides a method of producing an antagonistic antibody or fragment thereof that binds to human OX40 comprising culturing a host cell comprising an isolated nucleic acid encoding the antagonistic antibody or fragment thereof that binds to human OX40 or a vector comprising an isolated nucleic acid encoding the antagonistic antibody or fragment thereof that binds to human OX40 so that the nucleic acid is expressed and the antibody produced. Preferably the antibody is isolated. For host cells, nucleic acids and vectors, the ones described above can be used. Expression of the nucleic acids can be obtained by, e.g. a combination of recombinant DNA techniques and gene transfection methods as is well known in the art (e.g., Morrison S (1985) Science 229: 1202) and as further outlined above. For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into vectors such as expression vectors. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH1 segment(s) within the vector and the VK segment is operatively linked to the CK segment within the vector.

Characterization and Purification of Anti-OX40 Antibodies

Screening for antibodies can be performed using assays to measure binding to human OX40 and/or assays to measure the ability to block the binding of OX40 to its ligand, OX40L. An example of a binding assay is an ELISA, in particular, using a fusion protein of human OX40 and human Fc, which is immobilized on plates, and employing a conjugated secondary antibody to detect anti-OX40 antibody bound to the fusion protein. An example of a blocking assay is a flow cytometry based assay measuring the blocking of OX40 ligand fusion protein binding to OX40 on human CD4 cells. A fluorescently labelled secondary antibody is used to detect the amount of OX40 ligand fusion protein binding to the cell. This assay is looking for a reduction in signal as the antibody in the supernatant blocks the binding of ligand fusion protein to OX40. A further example of a blocking assay is an assay where the blocking of costimulation of naive human T cells mediated by OX40 ligand fusion protein coated to a plate is measured by measuring thymidine incorporation. As an assay for evaluating the functional activity of anti-OX40 antibodies e.g. the reduction of T cell activation the human Mixed Lymphocyte Reaction (MLR) as described in Examples 3 and 8 can be used. Antibodies of the present invention may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. To purify OX40 antibodies, selected host cells can be grown in e.g. spinner-flasks for monoclonal antibody purification. Supernatants can be filtered and concentrated before affinity chromatography with protein A-sepharose (Pharmacia, Piscataway, NJ). Eluted antibodies can be checked by gel electrophoresis and high performance liquid chromatography to ensure purity. A preferred antibody of the present invention is thus an isolated and/or purified antibody that binds to human OX40.

Immunoconjugates

In another aspect, the present invention provides an antagonist OX40 antibody or a fragment thereof that binds to human OX40, linked to a therapeutic agent, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil dacarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be linked to an antibody of the invention include duocarmycins, calicheamicins, maytansines and auristatins, and derivatives thereof. An example of a calicheamicin antibody conjugate is commercially available (Mylotarg®; American Home Products). Cytotoxins can be linked to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito G et al., (2003) Adv. Drug Deliv. Rev. 55: 199-215; Trail P A et al., (2003) Cancer Immunol. Immunother. 52: 328-337; Payne G (2003) Cancer Cell, 3: 207-212; Allen T M (2002) Nat. Rev. Cancer, 2: 750-763; Pastan I & Kreitman R J (2002) Curr. Opin. Investig. Drugs, 3: 1089-1091; Senter P D & Springer C J, (2001) Adv. Drug Deliv. Rev. 53: 247-264. Antibodies of the present invention also can be linked to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for preparing radioimmunconjugates are established in the art. Examples of radioimmunoconjugates are commercially available, including Zevalin® (EDEC Pharmaceuticals) and Bexxar® (Corixa Pharmaceuticals) and similar methods can be used to prepare radioimmunoconjugates using the antibodies of the invention. The antibody immunoconjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for linking such therapeutic agents to antibodies are well known, see, e.g., Arnon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985); Hellstrom et al., "Antibodies For Drug Delivery", in Controlled Drug Delivery (2nd Ed.), Robinson et al., (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al., (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985), and Thorpe P E & Ross W C (1982) Immunol. Rev. 62: 119-58.

In another aspect, the present invention provides an antagonist OX40 antibody or a fragment thereof that binds to human OX40, administered together with a therapeutic agent, such as a cytotoxin, a drug (e.g., an immunosuppressant) or a radiotoxin.

Pharmaceutical Compositions

In another aspect, the present invention provides a composition, e.g., a pharmaceutical composition, comprising the antagonist antibody or fragment thereof, of the present invention, and a pharmaceutically acceptable carrier. Such compositions may include one or a combination of (e.g., two or more different) antibodies, and/or immunoconjugates of the invention and/or a therapeutic agent, such as a cytotoxin, a drug (e.g., an immunosuppressant) or a radiotoxin as described supra. For example, a pharmaceutical composition of the invention can comprise a combination of antibodies (or immunoconjugates) that bind to different epitopes on the target antigen or that have complementary activities. Pharmaceutical compositions of the invention also can be administered in combination therapy, i.e., combined with other agents. For example, the combination therapy can include an antagonist OX40 antibody of the present invention combined with at least one other anti-inflammatory or immunosuppressant agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody or immunoconjugate, may be coated in a material to protect the compound from the action of acids and other natural conditions that may inactivate the compound. Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

In another aspect, the present invention provides a composition comprising an immunoconjugate comprising the antagonist antibody or fragment thereof that binds to human OX40 linked to a therapeutic agent and a pharmaceutically acceptable carrier. Immunoconjugates and therapeutic agents which can be used are as described supra.

In another aspect, the present invention provides a composition comprising the antagonist antibody or fragment thereof of the present invention which further comprises another pharmaceutically active agent. Preferably the another pharmaceutically active agent is one or more of: a) another antagonist to human OX40, b) an analgesic agent and c) an immune suppressive agent e.g. a glucocorticoid such as prednisone.

A pharmaceutical composition of the invention may also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic-acid (EDTA), sorbitol, tartaric acid, phosphoric acid, and the like. Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic and Other Uses

The antagonist antibodies of the present invention have numerous in vitro and in vivo diagnostic and therapeutic utilities involving the diagnosis and treatment of OX40 mediated disorders. For example, these molecules can be administered to cells in culture, in vitro or ex vivo, or to human subjects, e.g., in vivo, to treat, prevent and to diagnose a variety of OX40-mediated disorders. Preferred subjects are human and include patients having disorders mediated by OX40 activity (OX40 mediated disorders). The antagonist antibodies of the present invention can be effective in treating patients independent of their OX40 costimulatory status. More preferred subjects are human and include patients expressing a low level of OX40.

A "patient" for the purposes of the present invention includes both humans and other animals, preferably mammals and most preferably humans. Thus the antibodies of the present invention have both human therapy and veterinary applications. The term "treatment" or "treating" in the present invention is meant to include therapeutic treatment, as well as prophylactic, or suppressive measures for a disease or disorder. Thus, for example, successful administration of an antibody prior to onset of the disease results in treatment of the disease. As another example, successful administration of an antibody after clinical manifestation of the disease to combat the symptoms of the disease comprises treatment of the disease. "Treatment" and "treating" also encompasses administration of an antibody after the appearance of the disease in order to eradicate the disease. Successful administration of an antibody after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In a particular embodiment, the antagonist antibodies are used in vivo to treat, prevent or diagnose a variety of OX40-mediated disorders. Thus the invention provides a method for treating an OX40 mediated disorder in a subject, the method comprising administering to the subject a therapeutically effective amount of the antagonist antibody or fragment thereof. Exemplary OX40 mediated disorders include infections (viral, bacterial, fungal and parasitic), endotoxic shock associated with infection, arthritis, rheumatoid arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma (surgery), graft-versus-host disease (GVHD), transplant rejection, cardiovascular disease including ischaemic diseases such as myocardial infarction as well as atherosclerosis, intravascular coagulation, bone resorption, osteoporosis, osteoarthritis, periodontitis, hypochlorhydia and neuromyelitis optica.

Other exemplary OX40 mediated disorder include infections (viral, bacterial, fungal and parasitic), endotoxic shock associated with infection, arthritis, rheumatoid arthritis, asthma, bronchitis, influenza, respiratory syncytial virus, pneumonia, chronic obstructive pulmonary disease (COPD), idiopathic pulmonary fibrosis (IPF), cryptogenic fibrosing alveolitis (CFA), idiopathic fibrosing interstitial pneumonia, emphysema, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma (surgery), graft-versus-host disease (GVHD), transplant rejection, cardiovascular disease including ischaemic diseases such as myocardial infarction as well as atherosclerosis, intravascular coagulation, bone resorption, osteoporosis, osteoarthritis, periodontitis, hypochlorhydia and neuromyelitis optica.

Preferred OX40 mediated disorders to be treated with the antibody of the invention are selected from the group consisting of multiple sclerosis, rheumatoid arthritis, colitis, psoriasis, asthma, COPD, IPF, graft-versus-host-disease (GVHD), atherosclerosis and diabetes. A particular preferred OX40 mediated disorders to be treated with the antibody of the invention is graft-versus-host-disease (GVHD).

The present invention also provides an antibody for use in the treatment of pain, particularly pain associated with inflammation.

In one embodiment, the antibodies of the invention can be used to detect levels of OX40, or levels of cells which contain OX40 on their membrane surface, which levels can then be linked to certain disease symptoms. Alternatively, the antibodies can be used to inhibit or block OX40 function which, in turn, can be linked to the prevention or amelioration of certain disease symptoms, thereby implicating OX40 as a mediator of the disease. This can be achieved by contacting a sample and a control sample with the OX40 antibody under conditions that allow for the formation of a complex between the antibody and OX40. Any complexes formed between the antibody and OX40 are detected and compared in the sample and the control. In light of the specific binding of the antibodies of the invention for OX40, the antibodies of the invention can be used to specifically detect OX40 expression on the surface of cells e.g. can be used to detect a patient having low expression level of OX40. The antibodies of the invention can also be used to purify OX40 via immunoaffinity purification.

Thus the present invention also provides an in vitro screening method to detect a patient having a low expression level of OX40, comprising the steps of:
(a) purifying peripheral blood mononuclear cells (PBMCs) from a patient blood sample;
(b) subjecting the PBMCs to flow cytometric analysis; and
(c) determining the number of OX40 positive cells in $CD4^+$ and/or $CD8^+$ T cells and comparing this number to control levels.

In a preferred embodiment, a low expression level of OX40 is indicated by an increase in the expression level of OX40 positive cells when compared to control levels of up to 10%, more preferably of up to 20% and even more preferably of up to 30%. The approach of determining OX40 expression is further described in detail in Kotani A et al., (2001) Blood, 98: 3162-4 and Xiaoyan Z et al., (2005) Clin. Exp. Immunol. 143: 110-6.

In another embodiment, the antibodies of the invention can be initially tested for binding activity associated with therapeutic or diagnostic use in vitro. For example, compositions of the invention can be tested using flow cytometric assays.

The present disclosure further provides the use of an antagonist antibody or fragment thereof as a medicament and the use of an antagonist antibody or fragment thereof in the preparation of a medicament for the treatment of an OX40 mediated disorder. In a further embodiment the present disclosure provides the antagonist antibody or fragment thereof for use as a medicament. Also provided by the present disclosure is the antagonist antibody or fragment thereof for use in a method for treating an OX40 mediated disorder. OX40 mediated disorders are the ones as described supra. The antagonist antibody of the present invention may be particularly useful for treating OX40 mediated disorders independent of the OX40 costimulatory status of a patient. In a preferred embodiment, the antagonist antibody or fragment thereof can be used for treating an OX40 mediated disorder wherein a patient expresses a low level of OX40.

As previously described, antagonist OX40 antibodies of the invention can be co-administered with one or other more therapeutic agents, e.g., a cytotoxic agent, a radiotoxic agent or an immunosuppressive agent. The antibody can be linked to the agent (as an immunoconjugate as described supra) or can be administered separate from the agent. In the latter case (separate administration), the antibody can be administered before, after or concurrently with the agent or can be co-administered with other known therapies, e.g., an anti-cancer therapy, e.g., radiation.

For administration of the antibody, the dosage ranges from about 0.0001 to 100 mg/kg, and more usually 0.01 to 10 mg/kg, of the host body weight. An exemplary treatment regime entails administration once per week, once every two weeks, once every three weeks, once every four weeks, once a month, once every 3 months or once every three to 6 months. The antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml. Alternatively the antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated.

Actual dosage levels of the active ingredients, i.e. the antibody in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" of an OX40 antibody of the invention preferably results in a decrease in severity of disease symptoms, an increase in frequency and duration of disease symptom-free periods, and/or a prevention of impairment or disability due to the disease affliction. The ability of a compound for the treatment of an OX40 mediated disorder can be evaluated in an animal model system predictive of efficacy in human. Alternatively, this property of a composition can be evaluated by examining the ability of the compound to inhibit cell growth, such inhibition can be measured in vitro by assays known to the skilled practitioner. One of ordinary skill in the art would be able to determine such amounts based on such factors as the subject's size, the severity of the subject's symptoms, and the particular composition or route of administration selected.

The antibody or the composition of the present invention can be administered via one or more routes of administration using one or more of a variety of methods known in the art. As will be appreciated by the skilled artisan, the route and/or mode of administration will vary depending upon the desired results. Preferred routes of administration include intravenous, intramuscular, intradermal, intraperitoneal, subcutaneous, spinal or other parenteral routes of administration, for example by injection or infusion. More preferred routes of administration are intravenous or subcutaneous. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, for example, intranasally, orally, vaginally, rectally, sublingually or topically, Article of Manufacture and Kit In another embodiment of the disclosure, an article of manufacture comprising the antagonist antibody or fragment thereof, the composition or the immunoconjugate of the invention for the treatment of a OX40 mediated disorder is provided. The article of manufacture may comprise a container and a label or package insert on or associated with the container. Suitable containers include, for example, bottles, vials or syringes. The containers may be formed from a variety of materials such as glass or plastic. The container holds a composition that may be effective for treating the condition and may have a sterile access port (e.g., the container may be an intravenous solution bag or a vial having a stopper pierceable by a hypodermic injection needle). At least one active agent in the composition may be the antagonist antibody described herein. The label or package insert may indicate that the composition may be used for treating the condition of choice, such as cancer. In one embodiment, the label or package insert may indicate that the composition comprising the antagonist antibody may be used to treat an OX40-mediated disorder.

Moreover, the article of manufacture may comprise (a) a first container with a composition contained therein, wherein the composition comprises the antagonist antibody herein, and (b) a second container with a composition contained therein, wherein the composition comprises a therapeutic agent other than the antagonist antibody. The article of manufacture in this embodiment of the disclosure may further comprise a package insert indicating that the first and second compositions can be used in combination to treat a OX40 mediated disease or disorder. Such therapeutic agent may be any of the adjunct therapies described in the preceding section (e.g., a thrombolytic agent, an anti-platelet agent, a chemotherapeutic agent, an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Also within the scope of the present invention are kits comprising the antibody, the compositions or the immunoconjugates of the invention and instructions for use. The kit can further contain one more additional reagents, such as an immunosuppressive reagent, a cytotoxic agent or a radiotoxic agent, or one or more additional antagonist antibodies of the invention (e.g., an antagonist antibody having a complementary activity which binds to an epitope in the OX40 antigen distinct from the first antagonist antibody).

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1: Generation and Screening of Mouse Anti-Human OX40 Antibodies

To produce the recombinant human OX40-Fc protein, a cDNA for the human TNFRSF4 was purchased from ima-Genes (clone number: RZPDB737H0329D; Berlin, Germany). This cDNA was used as a template to PCR-amplify the DNA coding region of the human TNFRSF4 extracellular domain (SEQ ID NO: 11). In a separate PCR reaction, the Fc region of a human IgG1 (EU positions 223-451) was amplified by PCR adding a 5' GSGGG linker and a 3' SA-6×His linker and restriction sites for cloning. The two resulting products were then fused using overlap extension PCR with flanking primers, adding restriction sites for subsequent cloning into a modified mammalian expression vector based on the pcDNA3.1(-) plasmid from Invitrogen (Invitrogen AG, Basel, Switzerland, Cat. No. V795-20), containing the human CMV promoter with the Ig donor acceptor fragment (first intron) described in U.S. Pat. No. 5,924,939, the OriP sequence (Koons M D et al., (2001) J Virol. 75(22): 10582-92), the SV40 enhancer, and the SV40 polyA fused to the gastrin terminator as described by Kim D, et al., (2003) Biotechnol. Prog. 19(5): 1620-2. This recombinant plasmid allowed for expression of the human TNFRSF4 extracellular domain—Fc fusion protein in mammalian cells with secretion into the cell culture medium driven by the native signal peptide of the human TNFRSF4 protein. For recombinant protein production, the aforementioned recombinant vector was transfected into suspension-adapted HEK 293 cells (ATCC number CRL 1573) using jetPEI™ transfection reagent (Polyplus-transfection S.A., Strasbourg, France; distributor: Brunschwig, Basel, Switzerland). The cell culture supernatant was collected after five days and further purified using a Protein A affinity purification column (HiTrap Protein A sepharose column; GE Healthcare Europe GmbH, Glattbrugg, Switzerland) operated on an ÄKTA FPLC system (GE Healthcare Europe GmbH, Glattbrugg, Switzerland).

To produce the recombinant human OX40-his protein, the extracellular region of human TNFRSF4 (SEQ ID NO: 11) was amplified by PCR adding a 3' GSG-6×His linker and restriction sites for cloning. The PCR product was subsequently cloned in the modified pcDNA3.1(-) plasmid described above. This recombinant plasmid allowed for the expression of the human OX40-his protein in mammalian cells with secretion into the cell culture media driven by the native signal peptide of the human TNFRSF4. For protein production, the recombinant vector was transfected into suspension-adapted HEK 293 cells (ATCC number CRL 1573) using jetPEI™ transfection reagent (Polyplus-transfection S.A., Strasbourg, France; distributor: Brunschwig, Basel, Switzerland). The cell culture supernatant was collected five days after transfection and purified using a $Ni^{2+}$-NTA affinity purification column (HiTrap $Ni^{2+}$-NTA sepharose column; GE Healthcare Europe GmbH, Glattbrugg, Switzerland) operated on an ÄKTA FPLC system (GE Healthcare Europe GmbH, Glattbrugg, Switzerland). Recombinant human OX40-Fc and OX40-his proteins were found to be 95% pure as judged by SDS-PAGE, and further buffered exchanged into phosphate buffer saline (PBS) prior use.

Recombinant human OX40-Fc protein dissolved in PBS was mixed with an equal volume of Stimune adjuvant (Prionics, Switzerland, ref: 7925000) and an emulsion was prepared. The emulsion was transferred to 0.5 mL insulin syringes (BD Pharmingen, Allschwil, Switzerland) and BALB/c animals (Harlan, Netherlands) were immunized sub-cutaneously in the back footpads, the base of the tail and the neck with 50 μg of the emulsified protein. The immunization was repeated two weeks later with the same amount of antigen and the same route of injection.

The presence of circulating anti-human OX40 antibodies in the immunized mouse sera was evaluated by direct ELISA using plates coated with the recombinant human OX40-his protein. A serial dilution (from $1:10^0$ to $1:10^9$) of the different mouse sera was added to the plates and the bound antibodies were detected using a goat anti-mouse H+L whole molecule-HRP (Sigma-Aldrich Chemie GmbH, Buchs, Switzerland). A final sub-cutaneous boost with 50 μg of antigen without adjuvant was performed in animals displaying the best anti-human OX40 IgG serum titer three days before sacrifice.

Animals were euthanized and the inguinal, axillary, brachial, popliteal and sciatic lymph nodes were collected to prepare a single cell suspension by disturbing the lymph node architecture with two 25G needles in a DNAse (Roche Diagnostics (Schweiz) AG, Rotkreuz, Switzerland) and collagenase (Roche Diagnostics (Schweiz) AG, Rotkreuz, Switzerland) solution. Single cell suspensions were fused to a myeloma cell line X63AG8.653 (mouse BALB/c myeloma cell line; ATCC accession number: CRL 1580; Kearney J F et al., (1979) J. Immunol. 123(4): 1548-1550) at a ratio of 7:1 (fusion partner-to-harvested lymph node cells) with polyethylene glycol 1500 (Roche Diagnostics (Schweiz) AG, Rotkreuz, Switzerland). The fused cells were plated into 96 well flat bottom plates containing mouse macrophages in DMEM-10 medium (Invitrogen AG, Basel, Switzerland) supplemented with 10% fetal bovine serum (FBS, PAA Laboratories, Pasching, Austria), 2 mM L-glutamine, 100U/ml (Biochrom AG, Germany) penicillin, 100 μg/ml streptomycin (Biochrom AG, Germany), 10 mM HEPES (Invitrogen AG, Basel, Switzerland), 50 μM β-mercaptoethanol (Sigma-Aldrich Chemie GmbH, Buchs, Switzerland), HAT (Sigma-Aldrich Chemie GmbH, Buchs, Switzerland) and 1% Growth factor (Hybridokine, Interchim/Uptima, Montluçon, France).

Approximately 800 wells from the fusions were screened by ELISA for the presence of mouse IgG that recognized human OX40 and blocked the binding of human OX40L on its receptor. Positive wells were expanded and subjected to two rounds of subcloning. Cells were collected and the heavy and light chains were cloned and sequenced.

Example 2: Cloning and Sequencing of the VH and VL Chains of the Anti-OX40 Antibodies from Hybridoma Cells For each positively selected hybridoma, total RNA was prepared, reverse-transcribed into cDNA and VH and VL genes were respectively amplified by PCR. These PCR products were ligated into a rescue-vector (pDrive vector; QIAGEN AG, Hombrechtikon, Switzerland; Cat. No. 231124), allowing for the DNA sequencing of individual PCR products and the determination of mono- or polyclonality of the selected hybridomas. This vector allowed for blue/white selection on LB-agar plates containing IPTG and X-gal (colonies with no insert were blue because of the degradation of X-gal by the LacZ α-peptide). Recombinant plasmids from positive (white) bacterial clones were prepared and sequenced using standard DNA sequencing primers specific for the vector backbone (M13rev, M13fwd, T7 or SP6). DNA sequences were finally subcloned into an expression vector for recombinant expression of the antibody of interest in mammalian cells.

RNA Isolation

Total RNA was isolated from 2-10×10$^6$ cells using the RNeasy Mini Kit from QIAGEN (QIAGEN AG, Hombrechtikon, Switzerland; Cat. No. 74106) according to the manufacturer's protocol; samples were quantified using a NanoDrop ND-1000 spectrophotometer (WITEC AG, Littau, Switzerland).

One Step RT-PCR

The total RNA preparations described above were further reverse-transcribed into cDNA, and the VH and VL fragments were amplified by PCR using two different mixtures of degenerated primers, each one allowing the recovery of all the different subfamilies of mouse immunoglobulin heavy chain variable fragments and variable heavy chain junction regions or the recovery of all mouse immunoglobulin light chain kappa variable fragments and variable light chain kappa junction regions. The primers used for reverse transcription and amplification were synthesized by Microsynth (Balgach, Switzerland), and were HPLC purified (Tables 1-4). Both reverse-transcription and PCR amplification were performed simultaneously using the QIAGEN one step RT-PCR kit (QIAGEN AG, Hombrechtikon, Switzerland; Cat. No. 210212). Since the technique used specific primers, each mRNA sample was then treated in duplicate allowing for the individual reverse-transcription and amplification of either the VH or the VL fragments. 2 μg of total RNA dissolved into RNase-free water to a final volume of 30 μl were mixed with: 10 μl of a 5× stock solution of QIAGEN OneStep RT-PCR Buffer, 2 μl of a dNTPs mix at a concentration of 10 mM, 3 μl of primer mix at a concentration of 10 μM and 2 μl of QIAGEN OneStep RT-PCR Enzyme Mix. The final mixture was then placed in a PCR tube, and cycled in a PCR-themocycler (BioRad iCycler version 4.006, Bio-Rad Laboratories AG, Reinach, Switzerland) using the following settings:

30 min at 50° C.
15 min at 95° C.
40 cycles: 30 sec at 94° C.
30 sec at 55° C.
1 min at 72° C.
10 min at 72° C.
Hold at 4° C.

pDrive Cloning

PCR products were run onto 2% agarose gels. Following DNA electrophoresis, the fragments of interest (~450 bp) were excised from the agarose gels, and further extracted using the Macherey-Nagel NucloSpin Extract II kit 250 (Macherey-Nagel, Oensingen, Switzerland; Cat. No. 740609.250). For DNA sequencing, the extracted PCR products were cloned into the rescue-vector described above (pDrive vector, QIAGEN AG, Hombrechtikon, Switzerland; Cat. No. 231124) and transformed into the *E. coli* TOP10 strain (Invitrogen AG, Basel, Switzerland; Cat. No. C404006)

Miniprep Extraction

Positive colonies were cultured overnight at 37° C. (shaking 250 RPM) in 1.5 ml of Luria Bertani (LB) medium supplemented with 100 μg/ml ampicillin seeded in Macherey-Nagel Square-well Block plates (Macherey-Nagel, Oensingen, Switzerland; Cat. No. 740488.24). The next day DNA miniprep extractions were performed using the NucleoSpin Multi-8 Plasmid kit (Macherey-Nagel, Oensingen, Switzerland; Cat. No. 740620.5).

Sequencing and Sequence Analysis

Samples were sent for DNA sequencing to the DNA sequencing service company Fasteris (Plan-les-Ouates, Switzerland). The standard primers: M13rev, M13fwd, T7, SP6 were used (Table 5). To analyse the DNA sequences, the Clone Manager 9 Professional Edition (Scientific & Educational Software, NC, USA) and the BioEdit Sequence Alignment Editor (Hall, TA (1999) Nucl. Acids. Symp. Ser. 41: 95-98) were used.

Cloning of Expression Vector for Recombinant Chimeric Antibody Expression

For recombinant expression in mammalian cells, the isolated murine VH and VL fragments were formatted as chimeric immunoglobulins using assembly-based PCR methods. These chimeric antibodies consist of a heavy chain where the murine heavy chain variable domain is fused to the human IgG1 heavy chain constant domains (γ1, hinge, γ2, and γ3 regions) and a light chain where the murine light chain variable domain is fused to a human kappa constant domain (Cκ). PCR-assembled murine variable and human constant parts were subsequently cloned into a modified mammalian expression vector based on the modified pcDNA3.1(−) vector from Invitrogen mentioned in Example 1 with the difference that a human immunoglobulin light chain kappa leader peptide was employed to drive protein secretion.

For protein production of the immunoglobulin candidates, equal quantities of heavy and light chain vector DNA were co-transfected into suspension-adapted HEK-293 (ATCC number: CRL-1573). The cell culture supernatant was collected after five days and purified using a Protein A affinity purification column (HiTrap Protein A sepharose column) operated on an ÄKTA FPLC system (both from GE Healthcare Europe GmbH, Glattbrugg, Switzerland).

TABLE 1

| primer Mix VH-back |
|---|
| GTGATC GCC ATG GCG TCG ACC GAK GTR MAG CTT CAG GAG TC |
| GTGATC GCC ATG GCG TCG ACC GAG GTB CAG CTB CAG CAG TC |
| GTGATC GCC ATG GCG TCG ACC CAG GTG CAG CTG AAG SAR TC |
| GTGATC GCC ATG GCG TCG ACC GAG GTC CAR CTG CAA CAR TC |
| GTGATC GCC ATG GCG TCG ACC CAG GTY CAG CTB CAG CAR TC |
| GTGATC GCC ATG GCG TCG ACC CAG GTY CAR CTG CAG CAR TC |
| GTGATC GCC ATG GCG TCG ACC CAG GTC CAC GTG AAG CAR TC |
| GTGATC GCC ATG GCG TCG ACC GAG GTG AAS STG GTG GAR TC |
| GTGATC GCC ATG GCG TCG ACC GAV GTG AWG STG GTG GAG TC |
| GTGATC GCC ATG GCG TCG ACC GAG GTG CAG STG GTG GAR TC |
| GTGATC GCC ATG GCG TCG ACC GAK GTG CAM CTG GTG GAR TC |
| GTGATC GCC ATG GCG TCG ACC GAG GTG AAG CTG ATG GAR TC |
| GTGATC GCC ATG GCG TCG ACC GAG GTG CAR CTT GTT GAR TC |
| GTGATC GCC ATG GCG TCG ACC GAR GTR AAG CTT CTC GAR TC |
| GTGATC GCC ATG GCG TCG ACC GAA GTG AAR STT GAG GAR TC |
| GTGATC GCC ATG GCG TCG ACC CAG GTT ACT CTR AAA SAR TC |
| GTGATC GCC ATG GCG TCG ACC CAG GTC CAA CTV CAG CAR CC |
| GTGATC GCC ATG GCG TCG ACC GAT GTG AAC TTG GAA SAR TC |
| GTGATC GCC ATG GCG TCG ACC GAG GTG AAG GTC ATC GAR TC |

TABLE 2

| primer Mix VH-forward |
|---|
| CCTCCACCACTCGAGCC CGA GGA AAC GGT GAC CGT GGT |
| CCTCCACCACTCGAGCC CGA GGA GAC TGT GAG AGT GGT |
| CCTCCACCACTCGAGCC CGC AGA GAC AGT GAC CAG AGT |
| CCTCCACCACTCGAGCC CGA GGA GAC GGT GAC TGA GGT |

TABLE 3

| primer Mix VL-back |
|---|
| GGCGGTGGC GCT AGC GAY ATC CAG CTG ACT CAG CC |
| GGCGGTGGC GCT AGC CAA ATT GTT CTC ACC CAG TC |
| GGCGGTGGCGCT AGC GAY ATT GTG MTM ACT CAG TC |
| GGCGGTGGC GCT AGC GAY ATT GTG YTR ACA CAG TC |
| GGCGGTGGC GCT AGC GAY ATT GTR ATG ACM CAG TC |
| GGCGGTGGC GCT AGC GAY ATT MAG ATR AMC CAG TC |
| GGCGGTGGC GCT AGC GAY ATT CAG ATG AYD CAG TC |
| GGCGGTGGCGCT AGC GAY ATY CAG ATG ACA CAG AC |
| GGCGGTGGC GCT AGC GAY ATT GTT CTC AWC CAG TC |
| GGCGGTGGCGCT AGC GAY ATT GWG CTS ACC CAA TC |
| GGCGGTGGC GCT AGC GAY ATT STR ATG ACC CAR TC |
| GGCGGTGGC GCT AGC GAY RTT KTG ATG ACC CAR AC |
| GGCGGTGGCGCT AGC GAY ATT GTG ATG ACB CAG KC |
| GGCGGTGGC GCT AGC GAY ATT GTG ATA ACY CAG GA |
| GGCGGTGGC GCT AGC GAY ATT GTG ATG ACC CAG WT |
| GGCGGTGGC GCT AGC GAY ATT GTG ATG ACA CAA CC |
| GGCGGTGGCGCT AGC GAY ATT TTG CTG ACT CAG TC |
| GGCGGTGGC GCT AGC GAA ACA ACT GTG ACC CAG TC |
| GGCGGTGGCGCT AGC GAA AAT GTK CTS ACC CAG TC |
| GGCGGTGGCGCT AGC CAG GCT GTT GTG ACT CAG GAA TC |

TABLE 4

| primer Mix VL-forward |
|---|
| ATGCTGAC GC GGC CGC ACG TTT KAT TTC CAG CTT GG |
| ATGCTGAC GC GGC CGC ACG TTT TAT TTC CAA CTT TG |

TABLE 4-continued

| primer Mix VL-forward |
| --- |
| ATGCTGAC GC GGC CGC ACG TTT CAG CTC CAG CTT GG |
| ATGCTGAC GC GGC CGC ACC TAG GAC AGT CAG TTT GG |

TABLE 5

| sequencing primers | |
| --- | --- |
| M13-Fwd | GTAAAACGACGGCCAGT |
| M13-Rev | AACAGCTATGACCATG |
| T7 | TAATACGACTCACTATAGG |
| SP6 | GATTTAGGTGACACTATAG |

Example 3: Biological Characterization of Anti-Human OX40 Antibodies

OX40-Specific Antibody Detection ELISA:

Antibody titers, specificity and production by hybridomas and recombinant antibody candidates were determined by a direct ELISA. Briefly, 96 well-microtiter plates (Costar USA, distributor VWR AG, Nyon, Switzerland) were coated with 100 µl of recombinant human OX40-his at 2 µg/ml in PBS (see Example 1 for the generation of the OX40-his protein). Plates were incubated overnight at 4° C. and were then blocked with PBS 2% BSA (Bovine Serum Albumine, PAA Laboratories, Pasching, Austria) at room temperature (RT) for one hour. The blocking solution was removed and the hybridoma supernatants or purified antibodies were added. The plates were incubated at RT for 30 minutes, then washed nine times with PBS 0.01% Tween-20 (Sigma-Aldrich Chemie GmbH, Buchs, Switzerland) and a Horseradish Peroxidase (HRP) labelled-Goat anti-mouse H+L-detection antibody (Sigma-Aldrich Chemie GmbH, Buchs, Switzerland) was added at a dilution of 1:1000. To detect recombinant chimeric antibodies (see Example 2) that possess a human Fc, a HRP-labeled rabbit anti human IgG antibody (Sigma-Aldrich Chemie GmbH, Buchs, Switzerland) at a dilution of 1:1000 was used as the detection antibody. Plates were incubated for 30 minutes at room temperature (RT), washed nine times with PBS 0.01% Tween-20 and the TMB substrate (Bio-rad Laboratories AG, Reinach, Switzerland) was added to the plates and the reaction stopped after six minutes by adding $H_2SO_4$. Absorbance was then read at 450 nm by a microplate reader (Biotek, USA; distributor: WITTEC AG, Littau, Switzerland). FIG. 1A shows that the chimeric 1D4 antibody and the chimeric 2F8 antibody recognize the OX40-his coated protein.

OX40L Blocking ELISA:

The recombinant human OX40 ligand protein (OX40L) was generated as followed: the cDNA for human TNFSF4 (clone name: IOH46203) was purchased from imaGenes (Berlin, Germany) and the extracellular portion (amino acids 51-183) of human TNFSF4 ligand (numbering according to the Uniprot Q6FGS4 sequence) was amplified with flanking restriction sites. The resulting PCR product encompassing an ASA linker and a 8-His tag sequence at its 5' end was subsequently cloned into a modified version of the pREP4 vector from Invitrogen (Invitrogen AG, Basel, Switzerland) carrying a CMV promoter, a Bovine Growth Hormone poly-adenylation, and the murine VJ2C leader peptide to drive the secretion of the recombinant protein. For recombinant protein production, the recombinant vector was transfected into suspension-adapted HEK 293 cells (ATCC number CRL 1573) using jetPEI™ transfection reagent (Polyplus-transfection S.A., Strasbourg, France; distributor: Brunschwig, Basel, Switzerland). Cell culture supernatant was collected after five days and purified using a Protein A affinity purification column (HiTrap Protein A sepharose column; GE Healthcare Europe GmbH, Glattbrugg, Switzerland) operated on an ÄKTA FPLC system (GE Healthcare Europe GmbH, Glattbrugg, Switzerland).

In order to determine if the generated anti-OX40 antibodies can block the binding of OX40L to the OX40 receptor, a blocking ELISA was developed. Ninety-six well-microtiter plates (Costar, USA; distributor VWR AG, Nyon, Switzerland) were coated with 100 µl of recombinant human OX40-Fc (see Example 1) at 2 µg/ml in PBS. Plates were incubated overnight at 4° C. and were then blocked with PBS 2% BSA at RT for one hour. The blocking solution was removed and the hybridoma supernatants or purified antibodies were added to the plate. Five minutes later, 50 µl of biotinylated-recombinant human OX40L at 0.04 mg/ml was added to each well. Plates were incubated at RT for 60 minutes, then washed nine times with PBS 0.01% Tween-20 and HRP-streptavidin (Sigma-Aldrich Chemie GmbH, Buchs, Switzerland) was added at a dilution of 1:2000. Plates were incubated for 30 minutes at RT, washed 9 times with PBS 0.01% Tween-20 and the TMB substrate (Bio-rad Laboratories AG, Reinach, Switzerland) was added to the plates and the reaction stopped after 6 minutes by adding $H_2SO_4$. Absorbance was then read at 450 nm by a microplate reader (Biotek, USA; distributor: WITTEC AG, Littau, Switzerland). FIG. 1B shows that the chimeric 1D4 antibody is able to block the interaction between OX40 and OX40L in a dose dependent manner, whereas the chimeric 2F8 antibody is not able to block the interaction between OX40 and OX40L.

Human Mixed Lymphocyte Reaction (MLR)

Blood from two different donors was collected in three 10 mL S-Monovette with citrate as an anti-coagulant (Sarstedt, Nümbrecht, Germany). Cells from donor No 1 were used as effector cells whereas cells from donor No 2 were used as target cells. PBMCs (peripheral blood mononuclear cells) from the 2 donors were purified using 50 mL Blood-Sep-Filter Tubes (distributor: Brunschwig, Basel, Switzerland) following the manufacturer's instructions. Cells were washed 2 times with Roswell Park Memorial Institute (RPMI, PAA Laboratories, Pasching, Austria) medium without FBS. The target cells were incubated with 50 µg/ml of mitomycin C (Sigma-Aldrich Chemie GmbH, Buchs, Switzerland) for 30 minutes at 37° C. Cells were then washed 3 times with RPMI without FBS and resuspended at $1 \times 10^6$ cell/mL in RPMI, 10% FBS (PAA Laboratories, Pasching, Austria), 2 mM L-glutamine (Lonza, Leuven, Belgium), 100U/ml penicillin, 100 µg/ml streptomycin (Biochrom AG, Berlin, Germany). In 96 well U bottom micro-plates (TPP, Trasadingen, Switzerland), 50'000 target cells and 80'000 effector cells were distributed in a final volume of 100 µl to each well. One hundred µl of antibody dilutions was added to the wells. Plates were incubated for 7 days at 37° C. in 5% $CO_2$ incubator. Seven days after the start of the MLR, cells were pulsed with 0.5 µCi of $^3H$ thymidine (Perkin Elmer). 18 hours after pulsing, cells were harvested and incorporated radioactivity was quantified on a Wallac beta counter. FIG.

2 shows that the chimeric 1D4 antibody is able to block the MLR in a dose dependent manner to a higher degree than the positive control.

Example 4: Binding of Anti-Human OX40 Antibodies on Human and Other Animal Specie Activated Peripheral Blood Mononuclear Cells (PBMC) by Flow Cytometry Human Cells Filters containing human leukocytes were collected from the Blood Collection Center from La Chaux-de-Fonds, Switzerland (Centre de Transfusion Sanguine et Laboratoire de Sérologie, rue Sophie-Mairet 29, CH-2300). Cells were removed from the filters by backflushing with 60 mL of PBS containing 10U/mL of liquemin (Drossapharm AG, Lucern, Switzerland). PBMCs were then purified with 50 mL Blood-Sep-Filter Tubes (distributor: Brunschwig, Basel, Switzerland) following manufacturer's instructions. Cells were washed 3 times with Roswell Park Memorial Institute (RPMI, PAA Laboratories, Pasching, Austria) medium with FBS (PAA Laboratories, Pasching, Austria). Cells were resuspended at $3 \times 10^6$ cells/ml in RPMI, 10% FBS (PAA Laboratories, Pasching, Austria), 2 mM Ultraglutamine (Lonza, Leuven, Belgium), 100U/ml penicillin, 100 µg/ml streptomycin (Biochrom AG, Berlin, Germany), 10 µg/ml of Phytohemagglutinin (PHA; Sigma-Aldrich Chemie GmbH, Buchs, Switzerland)+100 U/mL of rHu IL-2 (Proleukin, Novartis, Basel, Switzerland) in a 24 well plate (TPP, Trasadingen, Switzerland). Forty-eight hours later, cells were collected and analyzed by flow cytometry as described below.

HPB-ALL cells (T acute lymphoid leukemia cell line, from Deutsche Sammlung von Mikroorganismen and Zellkulturen GmbH, Braunschweig, Germany) were cultured in RPMI, 10% FBS. $2 \times 10^5$ cells were distributed in a 96 well V bottom plate (TPP, Trasadingen, Switzerland), and centrifuged for three minutes at 1300 rpm; supernatants were discarded, cells were collected and analyzed by flow cytometry as described below.

PBMCs and HPB-ALL cells prepared as described above were resuspended in 50 µl of FACS buffer (PBS, 2% FBS, 10% Versene (Invitrogen, USA) with 5 µg/mL of chimeric 1D4 antibody or 5 µg/mL or an appropriate isotype control or 20 µl of a PE-labelled commercial anti-human OX40 antibody (clone L106, BD Biosciences, Allschwil, Switzerland). Cells were incubated for 30 minutes on ice, washed two times and resuspended in 50 µl of FACS buffer. An anti-human IgG-Phycoerithrin-PE (BD Biosciences, Allschwil, Switzerland) diluted 1/200 was used to detect the chimeric 1D4 antibody and the isotype control antibody. Cells were incubated for 15 minutes on ice, washed once, resuspended in 400 µl of FACS buffer and analyzed on the FACS instrument (Cyan, Beckman Coulter International S.A., Nyon, Switzerland).

Cynomolgus Monkey Primary Cells

Whole blood from Cynomolgus monkeys (obtained from Professor Eric Rouiller, Laboratory of Neurophysiology, University of Fribourg, Fribourg, Switzerland), was collected in citrate tubes (BD Biosciences, Allschwil, Switzerland). Two mL of PBS was mixed with 3 mL of blood and the mixture was layered on the top of 10 ml of a 85:15 Ficoll: PBS mixture (GE Healthcare Europe GmbH, Glattbrugg, Switzerland). Samples were centrifuged for 20 minutes at room temperature without break. The PBMC layer was collected and washed three times with PBS. Cells were resuspended at $3 \times 10^6$ cells/mL in Dulbecco's Modified Eagle Medium (DMEM, PAA Laboratories, Pasching, Austria), 10% FBS (PAA Laboratories, Pasching, Austria), Non-essential amino acids (PAA Laboratories, Pasching, Austria) 1 mM Sodium Pyruvate (PAA Laboratories, Pasching, Austria), 2 mM Ultraglutamine (Lonza, Belgium), 100U/ml penicillin (Biochrom AG, Germany), 100 µg/ml streptomycin (Biochrom AG, Germany). One mL of the cell suspension was distributed in a 24 well plate (TPP, Trasadingen, Switzerland) and 10 ug/ml of PHA (PHA/M, Sigma-Aldrich Chemie GmbH, Buchs, Switzerland) 100 U/mL of rHu IL-2 (Proleukin, Novartis, Basel, Switzerland) were added. Cells were incubated for 50 hours at 37° C. in 5% $CO_2$ incubator. Activated PBMC were collected and resuspended in PBS/2.5% FBS (FACS buffer). Fifty thousand cells in 50 µl of FACS buffer were distributed in a 96 well V bottom plate and biotinylated anti-human OX40-chimeric 1D4 antibody or biotinylated isotype control antibody or biotinylated commercial anti-human OX40 raised in sheep (BD Biosciences, Allschwil, Switzerland) were added to the wells at 25 µg/ml. Samples were incubated for 20 minutes on ice and then cells were washed two times with cold FACS buffer and then incubated with Streptavidin-PE (BD Biosciences, Allschwil, Switzerland) at a 1:20 dilution for 15 minutes on ice. Cells were washed once with FACS buffer and then resuspended in 300 µl of FACS buffer. Propidium Iodide at a volume of 2 µl (PI; Sigma-Aldrich Chemie GmbH, Buchs, Switzerland) was added in each sample to exclude dead cells. Cells were analyzed by flow cytometry (Cyan, Beckman Coulter International S.A., Nyon, Switzerland).

FIGS. 3A and 3B shows that the chimeric 1D4 antibody is able to recognize OX40 expressed on the surface of human and cynomologus monkey activated lymphocytes, respectively, thus provides for cross-reactivity properties highly desired for drug development.

Example 5: Kinetic Binding Affinity Constants of the Chimeric 1D4 Antibody for Human OX40 Receptor Extracellular Domain by Surface Plasmon Resonance (SPR)

Kinetic binding affinity constants (KD) were measured on protein-A captured antibody using recombinant histidine tagged human OX40 receptor extracellular domain as described in Example 1 as analyte. Measurements were conducted on a BIAcore 2000 (GE Healthcare—BIAcore, Uppsala, Sweden) at room temperature, and analyzed with the BiaEvaluation software (BIAcore; v4.1).

A CM5 research grade sensor chip (GE Healthcare Europe GmbH, Glattbrugg, Switzerland; BR-1000-14) was activated by injecting 35 µl of a 1:1 N-hydroxysulfosuccinimide (NHS)/1-Ethyl-3-[3-dimethylaminopropyl]carbodiimide Hydrochloride (EDC) solution (v/v; 5 µl/min flowrate; on flow paths 1 and 2). Protein-A (ref. P7837; Sigma-Aldrich Chemie GmbH, Buchs, Switzerland) was diluted to a final concentration of 50 µg/µl in acetate buffer pH 4.5 (GE, BR-1003-50; one pH unit below pI) and subsequently immobilized on the previously activated CM5 sensor chip by injecting 35 µl on both flow path 1 and 2 (5 µl/min); this corresponded to approximately 1500 response units (RUs). The protein-A-CM5 sensor chip was then deactivated by injecting 35 µl of ethanolamine solution (50/min). Finally, two injections of 10 µl of glycine solution (GE, ref. BR-1003-54; 10 mM; pH 1.5) were performed to release non-crosslinked protein-A molecules.

Before affinity measurements, a mass transfer limitation test was performed by injecting a fixed concentration of analyte onto a fixed quantity of protein-A captured antibody at different flow-rates (5, 15, 30, 50, 75 µl/min for 2 min). Analysis of the on-rate slopes at different flow-rates indicated mass transfer.

For affinity measurements, the chimeric 1D4 antibody stored in 1×PBS buffer was diluted to a final concentration of 15 nM in HBS-EP buffer (GE, ref. BR-1001-88; 0.01 M Hepes, 0.15 M NaCl, EDTA 3 mM, 0.005% Surfactant P20, pH 7.4). 10 µl of this diluted stock were subsequently injected on the flow-path 2 of the protein-A CM5 chip (30 µl/min) to reach 200-250 RUs. Following this capture step, the recombinant histidine tagged human OX40 receptor extracellular domain was injected at different concentrations (50 nM to 0.4 µM) on the flow-path 1 and 2 (flow-path 1 being used as reference) at a 30 µl/min flow rate. After each binding event, surface was regenerated with glycine buffer pH 1.5 injected for 1 min (10

Measurements (sensorgram: fc2-fc1) were best fitted with a 2:1 bivalent analyte model with mass transfer. To account for the experimental variations in protein-A captured antibody at the beginning of each measurement, the Rmax value was set to local in all fits. Dissociation times were of at least 300-600 seconds. Measurements were performed in duplicate and included zero-concentration samples for referencing. The Chi2 value represents the sum of squared differences between the experimental data and reference data at each point; while the plots of residuals indicate the difference between the experimental and reference data for each point in the fit. Both Chi2 and residual values were used to evaluate the quality of a fit between the experimental data and individual binding models.

Measurements were performed in duplicates with the captured chimeric 1D4 anti-human OX40 antibody immobilized onto the protein-A sensor chip and the recombinant histidine tagged human OX40 receptor extracellular domain as analyte. KD value was between 91 and 116 nM with Chi2 values <1.25.

Example 6: Humanization of Mouse Monoclonal Antibody 1D4

Humanizing the anti-human OX40 mouse antibody 1D4 including selection of human acceptor frameworks, back mutations, and mutations that substantially retain and/or improve the binding properties of human CDR-grafted acceptor frameworks is described herein.

Design of the Reshaped Variable Regions

Homology matching was used to choose human acceptor frameworks to graft 1D4 CDRs. Databases e.g. a database of germline variable genes from the immunoglobulin loci of human and mouse (the IMGT database (the international ImMunoGeneTics information System®; Lefranc M P et al., (1999) *Nucleic Acids Res.* 27(1): 209-12; Ruiz M et al., (2000) *Nucleic Acids Res.* 28(1): 219-21; Lefranc M P (2001) *Nucleic Acids Res.* 29(1): 207-9; Lefranc M P (2003) *Nucleic Acids Res.* 31(1): 307-10; Lefranc M P et al., (2005) *Dev. Comp. Immunol.* 29(3): 185-203; Kaas Q et al., (2007) *Briefings in Functional Genomics & Proteomics,* 6(4): 253-64) or the VBASE2 (Retter I et al., (2005) Nucleic Acids Res. 33, Database issue D671-D674) or the Kabat database (Johnson G et al., (2000) Nucleic Acids Res. 28: 214-218)) or publications (e.g., Kabat E A et al., supra) may be used to identify the human subfamilies to which the murine heavy and light chain V regions belong and determine the best-fit human germlime framework to use as the acceptor molecule. Selection of heavy and light chain variable sequences (VH and VL) within these subfamilies to be used as acceptor may be based upon sequence homology and/or a match of structure of the CDR1 and CDR2 regions to help preserve the appropriate relative presentation of the six CDRs after grafting.

For example, use of the IMGT database indicates good homology between the 1D4 heavy chain variable domain framework and the members of the human heavy chain variable domain subfamily 2. Highest homologies and identities of both CDRs and framework sequences were observed for germline sequences: IGHV 2-70*10 (SEQ ID NO: 19), IGHV2-70*01 (SEQ ID NO: 20), IGHV2-70*13 (SEQ ID NO: 21), IGHV2-5*09 (SEQ ID NO: 22), and IGHV2-70*11 (SEQ ID NO: 23), all of which having sequence identity above 73% for the whole sequence up to CDR3. IGHV 2-70*10, IGHV2-70*01, and IGHV2-70*13 have a sequence identity of 74%; while IGHV2-5*09, and IGHV2-70*11 have a sequence identity of 73.5% and 73%, respectively.

Using the same approach, 1D4 light chain variable domain sequence showed good homology to the members of the human light chain variable domain kappa subfamily 3. Highest homologies and identities of both CDRs and framework sequences were observed for germline sequences: IGKV3-11*01 (SEQ ID NO: 24) (65.3% identity), IGKV1-39*01 (SEQ ID NO: 25) (64.9% identity), IGKV1D-39*01 (SEQ ID NO: 26) (64.9% identity), IGKV3-11*02 (SEQ ID NO: 27) (64.2% identity), and IGKV3-20*01 (SEQ ID NO: 28) (62.5% identity).

As starting point to the humanization process, human IGHV 2-70*10 (SEQ ID NO: 19), and IGKV3-11*01 (SEQ ID NO: 24) variable domains were selected as acceptors to the 1D4 CDRs. IGHV 2-70*10 was selected over other human heavy chain variable domains for its superior homology with 1D4 in its framework one region.

A first humanized antibody of human gamma one isotype was prepared (see below). The antibody encompassed a human-mouse hybrid heavy chain variable domain and a human-mouse hybrid light chain variable domain. The hybrid heavy chain variable domain was based on the human heavy chain variable domain IGHV 2-70*10 wherein germline CDR1 and 2 where respectively replaced for 1D4 heavy chain CDR1 and 2. Best matching JH segment sequence to the human acceptor framework was identified from the IMGT searches mentioned above. The resulting human-mouse hybrid heavy chain variable sequence having human IGHV 2-70*10 framework regions, 1D4 mouse CDRs, and best matching JH to human acceptor is refereed herein as heavy chain variable domain VH1 with SEQ ID NO: 29. Similarly, the human-mouse hybrid light chain variable domain used for this first humanized antibody candidate had human IGKV3-11*01 framework regions, 1D4 mouse CDRs, and best matching JK to human acceptor, and is refereed herein as light chain variable domain VL1 with SEQ ID NO: 30. The first humanized antibody encompassing VH1 and VL1 is abbreviated herein VH1/VL1 antibody.

Production of the First Humanized Antibody Prototype

Coding DNA sequences (cDNAs) for VH1 and VL1 were synthesized in a scFv format by GENEART AG (Regensburg, Germany) thereby allowing for a single DNA sequence to encompass both variable domains (SEQ ID NO: 31). Individual variable domain cDNAs were retrieved from this scFv construct by PCR, and further assembled upstream of their respective constant domain cDNA sequence(s) using PCR assembly techniques. Finally, the complete heavy and light chain cDNAs were ligated in independent vectors that are based on a modified pcDNA3.1 vector (Invitrogen, CA, USA) carrying the CMV promoter and a Bovine Growth Hormone poly-adenylation signal. The light chain specific vector allowed expression of human kappa isotype light chains by ligation of the light chain variable domain cDNA of interest in front of the kappa light chain constant domain cDNA using BamHI and BsiWI restriction enzyme sites; while the heavy chain specific vector was engineered to allow ligation of the heavy chain variable domain cDNA of interest in front of the cDNA sequence encoding the human IGHG1 CH1, IGHG1 hinge region, IGHG1 CH2, and IGHG1 CH3 constant domains using BamHI and SalI restriction enzyme sites. In both heavy and light chain expression vectors, secretion was driven by the mouse VJ2C leader peptide containing the BamHI site. The BsiWI restriction enzyme site is located in the kappa constant domain; whereas the SalI restriction enzyme site is found in the IGHG1 CH1 domain.

The VH1/VL1 antibody was transiently produced by co-transfecting equal quantities of heavy and light chains vectors into suspension-adapted HEK293-EBNA1 cells (ATCC® catalogue number: CRL-10852) using polyethylenimine (PEI, Sigma, Buchs, Switzerland). Typically, 100 ml of cells in suspension at a density of 0.8-1.2 million cells per ml is transfected with a DNA-PEI mixture containing 50 µg of expression vector encoding the heavy chain and 50 µg of expression vector encoding the light chain. When recombinant expression vectors encoding antibody genes are introduced into the host cells, antibodies are produced by further culturing the cells for a period of 4 to 5 days to allow for secretion into the culture medium (EX-CELL 293, HEK293-serum-free medium; Sigma, Buchs, Switzerland), supplemented with 0.1% pluronic acid, 4 mM glutamine, and 0.25 µg/ml geneticin).

The VH1/VL1 antibody was purified from cell-free supernatant using recombinant protein-A streamline media (GE Healthcare Europe GmbH, Glattbrugg, Switzerland), and buffered exchanged into phosphate buffer saline prior to assays. Binding to human OX40 was measured by SPR as described in Example 5.

Back Mutations of Grafted Human Frameworks

Since straight grafting of CDRs from 1D4 mouse antibody led to a candidate having no binding to human OX40 (Table 6 and FIG. 4), mutagenesis wherein human residues are substituted for mouse residues was initiated. This process is called back-mutation and is the most unpredictable procedure in the humanization of monoclonal antibodies. It necessitates the identification and the selection of critical framework residues from the mouse antibody that need to be retained in order to preserve affinity while at the same time minimizing potential immunogenicity in the humanized antibody. Table 7, Table 8, and FIG. 5 show residues (Kabat numbering) that differ between mouse and human antibody frameworks. Residues which may affect the conformations of CDRs or inter-variable domain packing are of particular interest since these may have the highest impact on antibody affinity.

To identify residues that may impact the most CDR conformation and/or inter-variable domain packing, a 3D model for the VH1-VL1 pair of variable domains was calculated using the structure homology-modelling server SWISS-MODEL (Arnold K et al., (2006) Bioinformatics, 22(2): 195-201; http://swissmodel.expasy.org) set in automated mode. Model analysis allowed the selection of a subset of positions based on their putative influence on CDR regions and/or heavy chain-light chain variable domain packing. This subset of positions consisted of variable heavy chain positions: 23, 35b, 48, 50, 60, and 62 as well as variable light chain positions: 1, 33, 34, 46, 47, 54, 56, and 71 (Kabat numbering). In addition to these back mutations, light chain position Y31 found in the VH1/VL1 antibody was deleted in some candidates.

Further humanized candidates based on various combinations of heavy and light chain substitutions were prepared in the context of the VH1/VL1 antibody sequence using standard mutagenesis and methods described above. Humanized antibody candidates were assayed for their binding affinity by SPR as described in Example 5.

Production yields and binding properties of some of the humanized antibodies based on these single or combination of substitutions are shown in Table 6. Out of the 28 antibodies shown, nine candidates did not show any binding to human OX40, and another group of nine had weak to poor binding. VL9 based humanized antibodies showed the most consistently to weakly bind human OX40 by SPR. Only two antibodies, VH6/VL9 and VH7/VL9 showed good binding to human OX40. Both humanized antibodies had back mutations at variable heavy chain positions: 23, 35b, 50, 60, and 62 and variable light chain positions: 33, 34, 46, 47 and 71 (Kabat numbering). In addition to these back mutations, both VH6/VL9 and VH7/VL9 benefited from the removal of light chain position 31. Surprisingly VH7/VL9 had improved affinity for human OX40 over 1D4 chimeric antibody and the VH6/VL9 variant. The binding affinities of these humanized antibodies are summarized in Table 9.

Thermostability of Selected Humanized Anti-OX40 Antibodies by Differential Scanning Calorimetry The thermal stabilities of the humanized antibodies were measured using differential scanning calorimetry (DSC). Monoclonal antibodies melting profiles are characteristic of their isotypes (Garber E & Demarest S J (2007) Biochem. Biophys. Res. Commun. 355: 751-7), however the mid-point melting temperature of the FAB fragment can be easily identified even in the context of a full-length IgG. Such mid-point melting of FAB portion was used to monitor monoclonal stability of the humanized candidates.

Calorimetric measurements were carried out on a VP-DSC differential scanning microcalorimeter (MicroCal, Northampton, UK). The cell volume was 0.128 ml, the heating rate was 200° C./h, and the excess pressure was kept at 65 p.s.i. All antibodies were used at a concentration of 1 mg/ml in PBS (pH 7.4). The molar heat capacity of antibody was estimated by comparison with duplicate samples containing identical buffer from which the antibody had been omitted. The partial molar heat capacities and melting curves were analyzed using standard procedures. Thermograms were baseline corrected and concentration normalized before being further analyzed using a Non-Two State model in the software Origin v7.0.

Humanized variant VH6/VL9 FAB fragment displayed a single transition at 76.3° C. with a shape and amplitude consistent with a cooperative unfolding which is generally observed for a compactly folded FAB fragments indicating that the engineering process was successful at retaining FAB stability. Overall the humanized variant showed a good thermal stability.

TABLE 6 humanized anti human OX40 antibodies

| Humanized antibody variant (IGHG1) | SEQ ID NOs | Mutations VH/VL | Transient expression (mg/l) | Binding to human OX40 |
|---|---|---|---|---|
| VH1/VL1 | 32, 39 | N.A./N.A. | 40 | No |
| VH1/VL2 | 32, 40 | N.A./L33M | 21 | No |
| VH1/VL3 | 32, 41 | N.A./F71Y | 17 | No |
| VH2/VL1 | 33, 39 | T23S/N.A. | 13 | No |
| VH2/VL2 | 33, 40 | T23S/L33M | 17 | No |
| VH2/VL3 | 33, 41 | T23S/F71Y | 14 | No |
| VH3/VL1 | 34, 39 | R50H/N.A. | 23 | No |
| VH3/VL2 | 34, 40 | R50H/L33M | 22 | No |
| VH3/VL3 | 34, 41 | R50H/F71Y | 18 | No |
| VH4/VL4 | 35, 42 | T23S-R50H/L33M-F71Y | 15 | Poor |
| VH4/VL9 | 35, 47 | T23S-R50H/ Y31deletion-L33M-A34H-L46P-L47W-F71Y | 3 | Weak |
| VH5/VL4 | 36, 42 | T23S-R50H-S60N-S62A/L33M-F71Y | 15 | Poor |
| VH5/VL5 | 36, 43 | T23S-R50H-S60N-S62A/ L33M-L46P-L47W-F71Y | 2 | Poor |
| VH5/VL6 | 36, 44 | T23S-R50H-S60N-S62A/ E1Q-L33M-L46P-L47W-F71Y | 2 | Poor |
| VH5/VL9 | 36, 47 | T23S-R50H-S60N-S62A/ Y31deletion-L33M-A34H-L46P-L47W-F71Y | 6 | Weak |
| VH6/VL5 | 37, 43 | T23S-S35bG-R50H-S60N-S62A/ L33M-L46P-L47W-F71Y | 0 | N.D. |
| VH6/VL6 | 37, 44 | T23S-S35bG-R50H-S60N-S62A/ E1Q-L33M-L46P-L47W-F71Y | 0.5 | N.D. |
| VH6/VL7 | 37, 45 | T23S-S35bG-R50H-S60N-S62 A/ Y31deletion-L33M-F71Y | 14 | N.D. |
| VH6/VL8 | 37, 46 | T23S-S35bG-R50H-S60N-S62A/ Y31deletion-L33M-A34H-F71Y | 7 | N.D. |
| VH6/VL9 | 37, 47 | T23S-S35bG-R50H-S60N-S62A/ Y31deletion-L33M-A34H-L46P-L47W-F71Y | 3.5 | Good |
| VH6/VL10 | 37, 48 | T23S-S35bG-R50H-S60N-S62A/ Y31deletion-L33M -R54L-T56S-F71Y | 0.5 | N.D. |
| VH6/VL11 | 37, 49 | T23S-S35bG-R50H-S60N-S62A/ Y31deletion-L33M-A34H-R54L-T56S-F71Y | 5.5 | N.D. |
| VH7/VL5 | 38, 43 | T23S-S35bG-I48L-R50H-S60N-S62A/ L33M-L46P-L47W-F71Y | 1 | N.D. |
| VH7/VL6 | 38, 44 | T23S-S35bG-I48L-R50H-S60N-S62A/ E1Q-L33M-L46P-L47W-F71Y | 1 | N.D. |
| VH7/VL7 | 38, 45 | T23S-S35bG-I48L-R50H-S60N-S62A/ Y31deletion-L33M-F71Y | 1.5 | Weak |
| VH7/VL8 | 38, 46 | T23S-S35bG-I48L-R50H-S60N-S62A/ Y31deletion-L33M-A34H-F71Y | 10 | Weak |
| VH7/VL9 | 38, 47 | T23S-S35bG-I48L-R50H-S60N-S62A/ Y31deletion-L33M-A34H-L46P-L47W-F71Y | 3 | Good |
| VH7/VL11 | 38, 49 | T23S-S35bG-I48L-R50H-S60N-S62A/ Y31deletion-L33M-A34H-R54L-T56S-F71Y | 11.5 | Weak/ Good |

TABLE 7 comparison of 1D4 and human acceptor heavy chain variable IGHV 2-70*10 frameworks

| Kabat position | 1D4 | CDR grafted IGHV 2-70*10 |
|---|---|---|
| 10 | G | A |
| 11 | I | L |
| 12 | L | V |
| 13 | Q | K |
| 15 | S | T |
| 19 | S | T |
| 23 | S | T |
| 35b | G | S |
| 41 | S | P |
| 44 | G | A |
| 48 | L | I |
| 50 | H | R |
| 60 | N | S |
| 62 | A | S |
| 65 | S | T |
| 66 | G | R |
| 79 | F | V |
| 81 | K | T |
| 82 | I | M |
| 82a | A | T |
| 82b | S | N |
| 82c | Y | M |
| 84 | T | P |
| 85 | T | V |

TABLE 8 comparison of 1D4 and human acceptor light
chain variable IGKV 3-11*01 frameworks

| Kabat position | 1D4 | CDR grafted IGKV 3-11*01 |
|---|---|---|
| 1 | Q | E |
| 10 | I | T |
| 13 | A | L |
| 18 | K | R |
| 19 | V | A |
| 21 | M | L |
| 22 | T | S |
| 33 | M | L |
| 34 | H | A |
| 42 | S | Q |
| 43 | S | A |
| 45 | K | R |
| 46 | P | L |
| 47 | W | L |
| 54 | L | R |
| 56 | S | T |
| 58 | V | I |
| 70 | S | D |
| 71 | Y | F |
| 72 | S | T |
| 76 | N | S |
| 77 | R | S |
| 78 | V | L |
| 80 | A | P |
| 83 | A | F |
| 85 | T | V |

TABLE 9 binding characteristics of selected humanized
and chimeric anti OX40 antibodies.

| Humanized variants | SEQ ID NOs | $k_{on}$ (1/Ms) | $k_{off}$ (1/s) | $K_D$ (nM) |
|---|---|---|---|---|
| 1D4 chimera | 50, 51 | $3.4 \times 10^4$ | $3.08 \times 10^{-3}$ | 91 |
| VH6/VL9 | 37, 47 | $3.54 \times 10^4$ | $3.56 \times 10^{-3}$ | 101 |
| VH7/VL9 | 38, 47 | $4.45 \times 10^4$ | $3.12 \times 10^{-3}$ | 70 |

Example 7: Epitope Characterization of Humanized Anti-OX40 Antibodies

To characterize the epitope of the humanized anti-OX40 antibodies, the VH6/VL9 antibody was mapped to a define domain of the human OX40 extracellular region using various human-rat OX40 chimeric proteins.

Preparation of Human-Rat OX40 Chimeric Proteins and ELISA

Rat and human-rat OX40 proteins were formatted as Fc fusions proteins according to the method described in Example 1. For the ELISA, OX40 proteins were coated at 2 μg/mL, in PBS, overnight at 4° C. on high binding 96-well plates (Coastar). The plates were blocked with PBS 2% Bovine Serum Albumin (BSA) before incubation with the VH6/VL9 antibody or isotype control antibody. The plates were then washed and incubated with goat-anti human Ig F(ab')2 fragment specific-HRP (Jackson ImmunoResearch Europe Ltd, Newmarket, UK). After washing, the plates were incubated with TMB substrate (Bio-Rad Laboratories AG, Reinach, Switzerland) to reveal antibody binding. The reaction was stopped by adding 2M $H_2SO_4$ and the optical density was read at 450 nM (OD 450 nM) on a Synergy HT2 spectrophotometer (Biotek, USA; distributor: WITTEC AG, Littau, Switzerland).

Results

Regardless of its origin, the OX40 extracellular region has been divided into four structural modules referred to as domain 1, 2, 3 and 4 (Compaan D M & Hymowitz S G (2006) Structure, 14(8): 1321-30). Chimeric OX40 proteins corresponding to the extracellular region of human OX4-0 (amino acids 29-214 of human TNFRSF4, numbering according to the Uniprot P43489 sequence) were constructed by exchanging one or more of the four domains between human and rat sequences. For example, the chimeric RHRR OX40 protein corresponds to the rat OX40 extracellular region wherein the second domain has been replaced by the corresponding human domain sequence.

Figure 7:
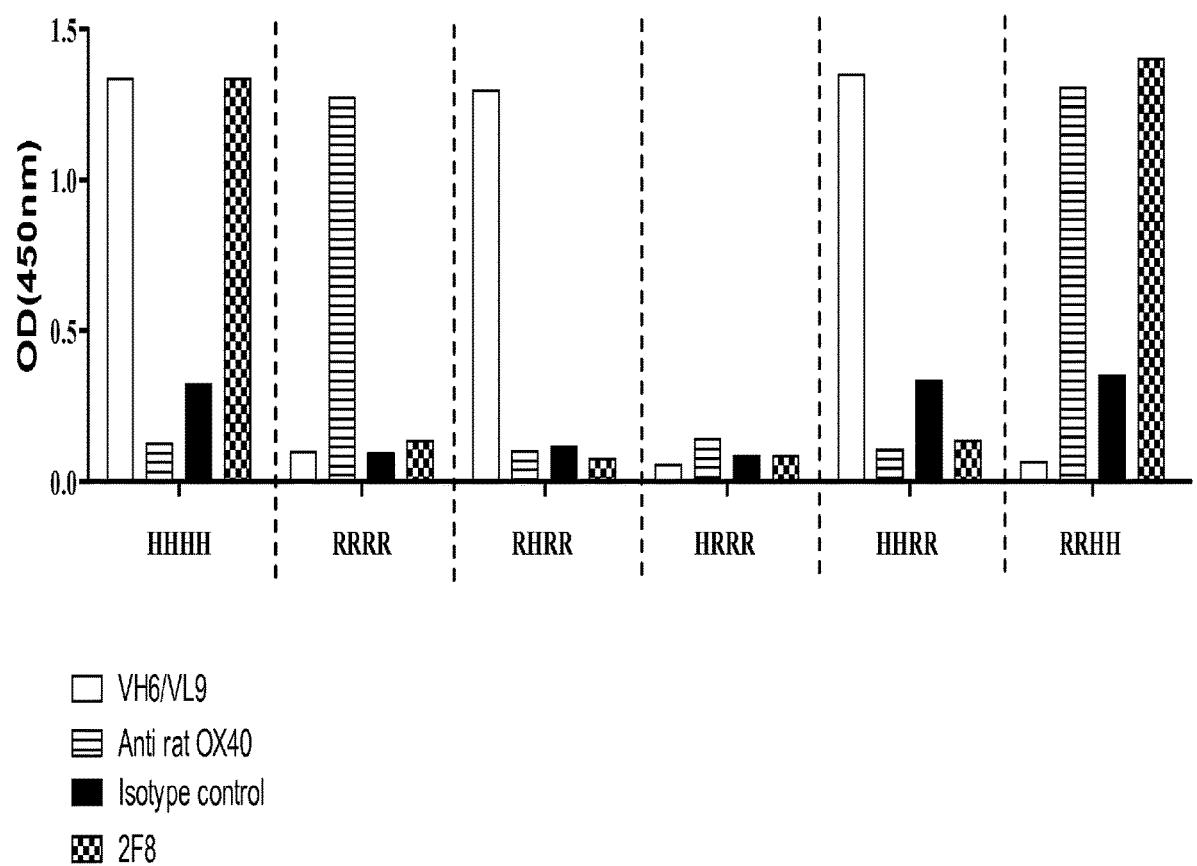
FIG. 7: Epitope Characterisation. This figure shows humanized anti-OX40 anti-antibody VH6/VL9 epitope based on ELISA assay results as described in Example 7.

A binding ELISA was performed to test the reactivity of the VH6/VL9 antibody on human OX40 extracellular region (abbreviated HHHH with SEQ ID NO: 11), rat OX40 extracellular region (abbreviated RRRR with SEQ ID NO: 52), and on four human-rat chimeric proteins: RHRR (SEQ ID NO: 53), HRRR (SEQ ID NO: 54), HHRR (SEQ ID NO: 55), and RRHH (SEQ ID NO: 56). The result of this ELISA is shown in FIG. 7. As a prerequisite to this epitope mapping experiment, the VH6/VL9 antibody was shown to bind the human OX40 protein but not the rat OX40 protein, indicating that there was no cross-reactivity to rat OX40. It was found that the VH6/VL9 antibody bound RHRR and HHRR but not HRRR or RRHH, indicating that VH6/VL9 epitope maps within the second domain of human OX40 extracellular region.

Example 8: VH6/VL9 Antibody Blocks Human Mix Lymphocyte Reaction by Killing and Blocking Mechanisms The potency of VH6/VL9 antibody to suppress in vitro immune reactions was tested in a one-way allogeneic mixed lymphocyte reaction (MLR). The MLR is an in vitro model of alloreactive T cell activation and proliferation (O'Flaherty E et al., (2000) Immunology, 100(3): 289-99; DuPont B & Hansen J A (1976) Adv. Immunol. 23: 107-202). When peripheral blood mononuclear cells (PBMCs) from two unrelated donors are mixed, T cells get activated through recognition of allogeneic major histocompatibility (MHC) molecules. This activation results in proliferation of T lymphocytes. The MLR reaction has been widely used to demonstrate the effect of T-cell targeting immunosuppressive drugs (Bromelow K V et al., (2001) J. Immunol. Methods, 247(1-2): 1-8). Immunosuppressive drugs, such as cyclosporine work mainly through inhibiting T cell activation. Besides testing the blocking effect by the VH6/VL9 antibody, the contribution of cytotoxic mechanisms such as antibody dependent cellular cytotoxicity (ADCC) on the inhibition of MLR was also investigated. Three different antibody formats of the VH6/VL9 antibody were tested in this assay: an IGHG1 format (referred herein as VH6/VL9), a non fucosylated IGHG1 (IgG1) format (referred herein as non fucosylated VH6/VL9), and an IGHG4 (IgG4) format (referred herein as VH6/VL9 IGHG4 S228P). IGHG1 (IgG1) antibodies are known to be competent for cytotoxicity mechanism such as ADCC. Non fucosylated IGHG1 antibodies are known to exhibit enhanced ADCC activity due to a higher affinity for the FcγRIIIa expressed on cytotoxic cells such as natural killer cells (NK cells) (Mizushima T et al., (2011) Genes Cells, 16(11): 1071-80). In contrast, IGHG4 (IgG4) antibodies are known to have no such Fc-mediated cytotoxicity mechanisms such as ADCC.

Formatting of the VH6/VL9 Antibody

IGHG4 immunoglobulin formatting having substitution S228P was achieved by replacing the cDNA sequence encoding the IGHG1 CH1, IGHG1 hinge region, IGHG1 CH2, and IGHG1 CH3 constant domains for a cDNA sequence encoding the IGHG4 CH1, IGHG4 hinge region having S228P substitution, IGHG4 CH2 and IGHG4 CH3 constant domains in the heavy chain specific vector described in Example 6. Substitution S228P was introduced in a human IGHG4 heavy chain cDNA template by standard PCR mutagenesis techniques. The resulting heavy chain has SEQ ID NO: 57. Production of the non-fucosylated VH6/VL9 IGHG1 antibody followed the protocol described in Example 14 of the WO2010/095031 publication.

Mixed Lymphocyte Reaction

Blood from two different human donors was collected in three 10 mL S-Monovette with citrate as an anti-coagulant (Sarstedt, Nümbrecht, Germany). Peripheral blood mononuclear cells (PBMCs) from the two human donors were purified using 50ML Blood-Sep-Filter Tubes (distributor: Brunschwig, Basel, Switzerland) following the Manufacturer's instructions. Cells were washed two times with Roswell Park Memorial Institute (RPMI, PAA Laboratories, Pasching, Austria) medium without FBS. Stimulator cells from the two donors were prepared by incubation with 50 µg/ml of mitomycin C (Sigma-Aldrich Chemie GmbH, Buchs, Switzerland) for 30 minutes at 37° C. Cells were then washed three times with RPMI without FBS and resuspended at $1\times10^6$ cell/mL in RPM, 10% FBS (PAA Laboratories, Pasching, Austria), 2 mM L-glutamine (Lonza, Leuven, Belgium), 100U/ml penicillin and 100 µg/ml streptomycin (Biochrom AG, Berlin, Germany). Responder cells were resuspended in RPMI, 10% FBS, L-glutamine, 100U/ml penicillin and 100 µg/ml streptomycin in 96 well U bottom micro-plates (TPP, Trasadingen, Switzerland). 50'000 stimulator cells and 80'000 responder cells were distributed in a final volume of 100 µl to each well. 100 µl of antibody dilutions (or medium only) was added to the wells. Plates were incubated for 7 days at 37° C. in 5% $CO_2$ incubator. The cells were pulsed with 0.5 µCi of $^3H$ thymidine (Perkin Elmer, Basel Switzerland) during the last 18 hours. Cells were harvested on a filtermat filter (Perkin Elmer) and incorporated radioactivity was quantified on a Wallac beta counter (Perkin Elmer).

Results

Figure 8A:
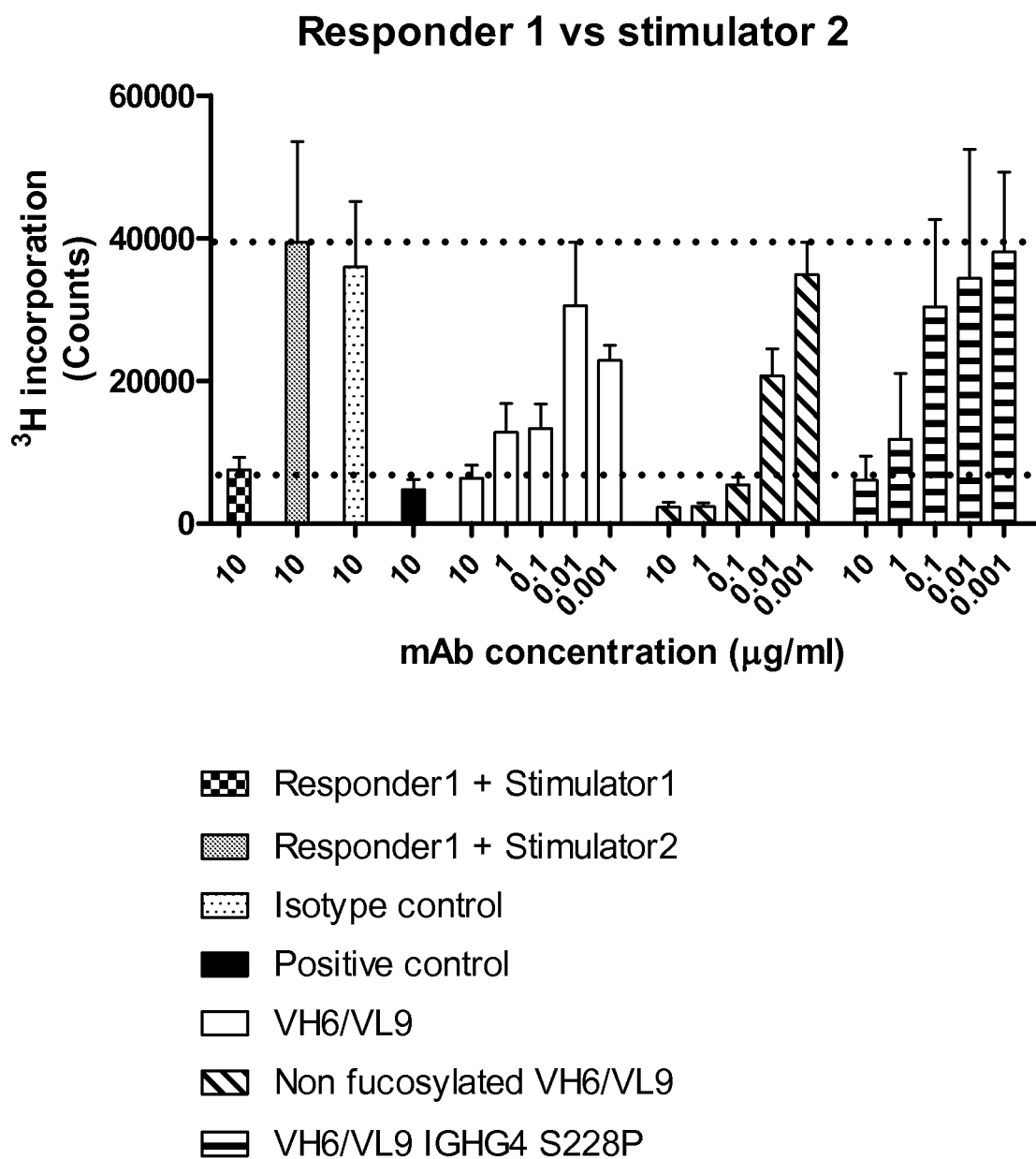
FIGS. 8A and 8B show the results of mixed lymphocyte reaction from two unrelated donors, with responder 1 cells+ stimulator 1 and 2 cells (FIG. 8A) and with responder 2 cells+stimulator 1 and 2 cells (FIG. 8B). The proliferation was measured by $^3$H-thymidine incorporation. The graphs show the absolute counts values for each condition±SEM. Responder cells were untreated PBMCs, stimulator cells were mitomycin-treated PBMCs. All conditions with test antibodies were done with responder cells mixed with heterologous stimulator PBMCs. The positive control was Efalizumab (anti LFA-1 antibody).
Figure 8B:
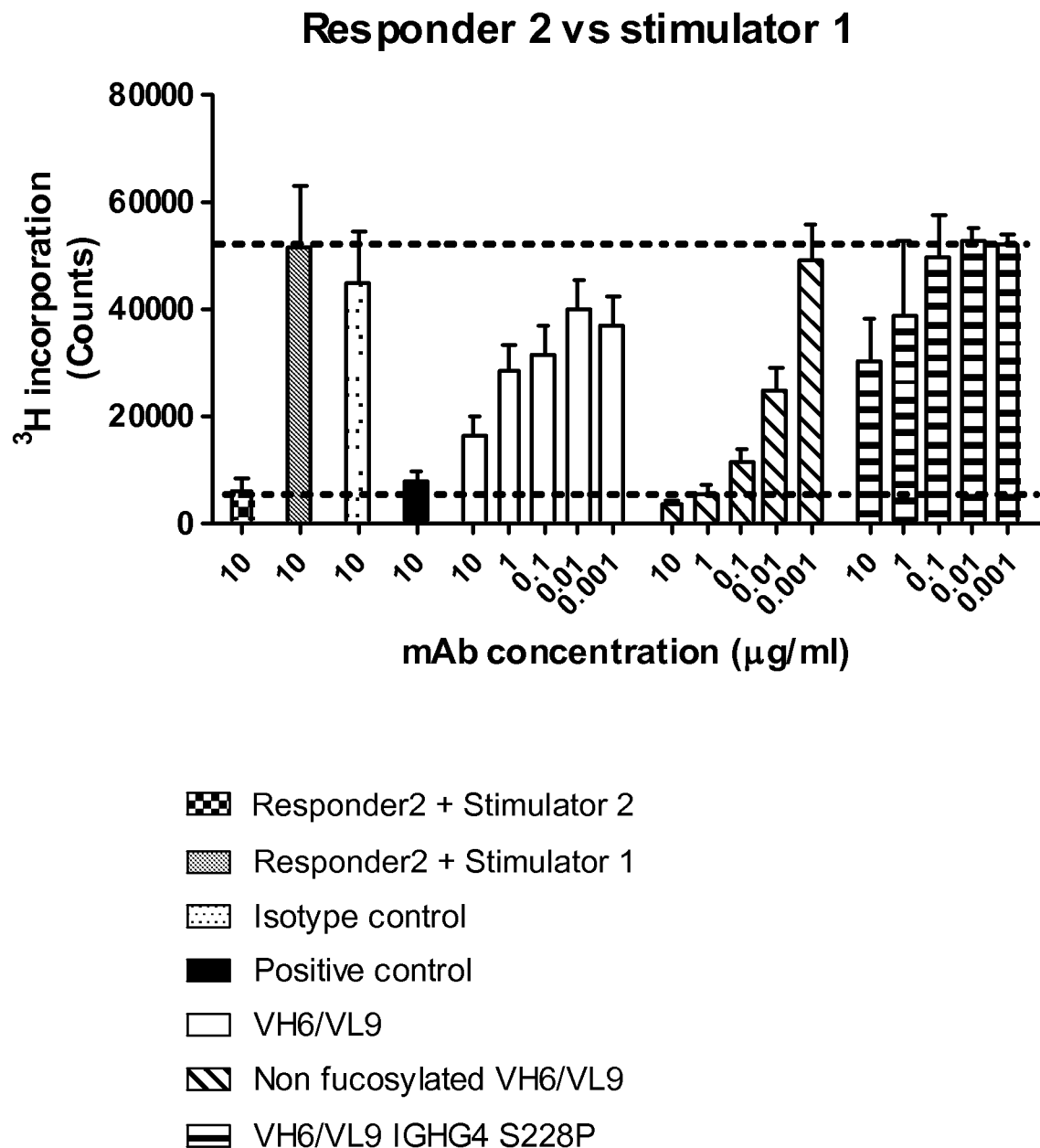

The results shown on FIG. 8 demonstrate that the VH6/VL9 antibody is able to efficiently inhibit MLR for two different individuals (responders) with $EC_{50}$ values around 100 ng/mL. The results also show a different response depending on the antibody format used and a difference in the contribution of blocking and cytotoxic mechanisms is observed in the MLR from different individuals.

The reactivity of T cells from responder 1 (FIG. 8A) was efficiently inhibited by the IGHG1 and IGHG4 formats indicating that cytotoxic mechanisms are not critical for responder 1. In contrast, the IGHG4 format was only poorly able to block the MLR from responder 2 (FIG. 8B) at high concentration and lost very rapidly its effect at lower concentrations, whereas the IGHG1 format could achieve more than 60% of inhibition, implying that, for responder 2, killing mechanisms are accounting for most of the inhibitory effect.

This difference in mode of action likely arises from the fact that activation, proliferation and survival of T cells in a MLR reaction is variably reliant on OX40 costimulatory signals between individuals, depending on the extent of allergenic reactivity and possibly other costimulatory signals. For individuals poorly dependent on OX40-derived costimulatory signals, elimination of activated T cells by ADCC mechanism is the main mechanism of action of the VH6/VL9.

Surprisingly, the non fucosylated IGHG1 format displayed a very potent ability to inhibit MLR for both responders. This observation highlights the fact that even if a blocking mechanism may be sufficient to achieve inhibition of MLR, addition or enhancement of killing mechanisms improves the inhibitory effect of anti-OX40 antibodies. Such enhancement is particularly useful when in treating OX40 mediated disorders regardless of the OX40 costimulatory status of patients, e.g when patients have low OX40 expression levels.

Example 9: VH6/VL9 Antibody Blocks Xenogeneic Graft-Versus-Host-Disease

Xenogeneic graft versus host (GVH) reaction is a model for the allogeneic graft versus host disease (GVHD) observed after bone marrow transplant in human patients. The GVH reaction is an acute immune response mediated by grafted immune cells which attack the host environment as a consequence of an allogeneic or xenogeneic MHC recognition (Murphy W J et al., (1996) Semin. Immunol. 8(4): 233-41). T lymphocytes are the main effector cells of GVH reactions. The immunosuppressive potency of the VH6/VL9 antibody was tested in a xenogeneic GVHD model based on the reconstitution of SCID mice with human PBMCs. In this model, human PBMCs and primarily the T lymphocytes launch a strong response against the mouse host cells. The reaction leads notably to severe skin and intestinal inflammation accompanied by weight loss. The most relevant readout of this model is the survival of the animals.

Method

Animals (SCID mice) were sub-lethally irradiated before being reconstituted with 30 million human PBMCs intraperitoneally. The mice were also depleted for mouse NK cells by twice weekly injections with the TMbeta1 antibody. The treatment with VH6/VL9 antibody, Enbrel® or vehicle was given i.v. weekly for five consecutive doses and started two days before the PBMC injection. Animals were treated either with vehicle (PBS) or the VH6/VL9 antibody at 10 mg/kg or 1 mg/kg, or Enbrel® (a fusion protein of the human soluble TNF receptor 2 fused to the Fc component of human IgG1, Amgen-Pfizer) at 8 mg/kg. The animals were checked and scored three times weekly for GVHD symptoms including weight loss, diarrhoea, fur aspect and general behaviour. Animals were ethically sacrificed if symptoms were considered too severe.

Results

Figure 9:
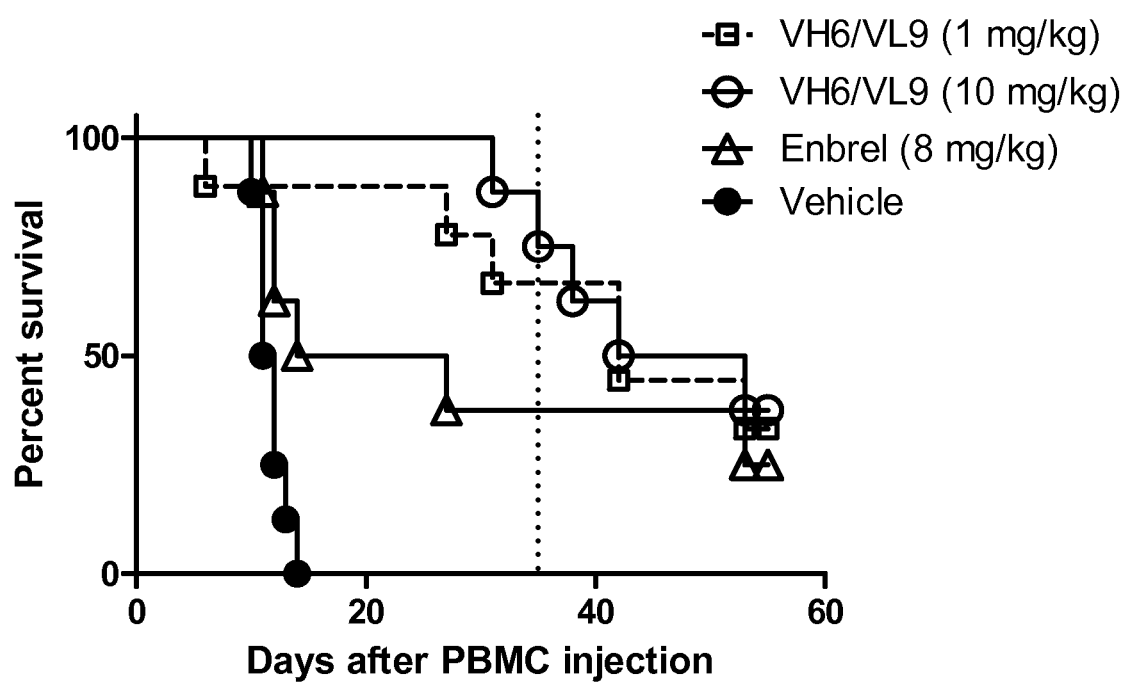
FIG. 9: Xenogeneic graft versus host reaction model. This figure shows the percent survival within groups of eight animals for each mentioned condition. Vehicle: only PBS. The vertical dotted line indicates the last day of treatment. No mortality and no symptoms were observed in a group of two irradiated control animals that did not received PBMCs (not shown).

FIG. 9 shows that the VH6/VL9 antibody very potently suppressed the GVHD reaction even at the lower, 1 mg/kg dose. Surprisingly, the VH6/VL9 antibody demonstrated improved efficacy over Enbrel®, which is a recognized therapy for GVHD in human (Xhaard A et al., (2011) Bull. Cancer, 98(8): 889-99; Simpson D (2001) Expert Opin. Pharmacother. 2(7): 1109-17). The median survival time of animals treated with the VH6/VL9 antibody at 1 or 10 mg/kg was four-fold longer compared to the vehicle treated group (Table 10) and two-fold longer compared to Enbrel®. In addition this result highlights that the VH6/VL9 antibody possesses no agonistic activity, since an agonistic anti-OX40 antibody has been reported to worsen GVHD in allogeneic mouse GVHD models (Valzasina B et al., (2005) Blood, 105(7): 2845-51; Blazar B R et al., (2003) Blood, 101(9): 3741-8), an event that was not observed in the present study.

TABLE 10

Median survival time (in days) of the indicated treatment groups

| Treatment | Vehicle | Enbrel ® | 1D4 (1 mg/kg) | 1D4 (10 mg/kg) |
|---|---|---|---|---|
| Survival median (days) | 11.5 | 20.5 | 42 | 47.5 |

Vehicle: only PBS.
1D4: GBR 830-1D4 antibody; Enbrel ® was the clinical product.

The invention claimed is:

1. An antagonistic antibody or fragment thereof that binds to human OX40, wherein said antibody or fragment thereof comprises:
  a heavy chain CDR1 comprising the amino acid sequence of SEQ ID NO: 1, a heavy chain CDR2 comprising the amino acid sequence of SEQ ID NO: 2, and a heavy chain CDR3 comprising the amino acid sequence of SEQ ID NO: 3; and
  a light chain CDR1 comprising the amino acid sequence of SEQ ID NO: 4, a light chain CDR2 comprising the amino acid sequence of SEQ ID NO: 5 and a light chain CDR3 comprising the amino acid sequence of SEQ ID NO: 6.

2. The manufacture antibody or fragment thereof of claim 1, wherein the antibody or fragment thereof is a murine antibody, chimeric antibody or a humanized antibody.

3. The antibody or fragment thereof of claim 1, wherein the antibody or fragment thereof is a humanized antibody.

4. The antibody or fragment thereof of claim 1, wherein the antibody or fragment thereof comprises a heavy chain variable region sequence comprising the amino acid sequence of SEQ ID NO: 7.

5. The antibody or fragment thereof of claim 1, wherein the antibody or fragment thereof comprises a non-CDR region of a heavy chain variable region sequence which is at least 80% identical to the non-CDR region of the heavy chain variable region sequence of SEQ ID NO: 7.

6. The antibody or fragment thereof of claim 1, wherein the heavy chain sequence comprises a non-CDR region which is at least 80% identical to the non-CDR region of the heavy chain variable region sequence of the heavy chain sequence selected from the group consisting of SEQ ID NOS: 35, 36, 37 and 38.

7. The antibody or fragment thereof of claim 6, wherein the antibody or fragment thereof comprises a heavy chain sequence comprising the amino acid sequence selected from the group consisting of SEQ ID NOS: 35, 36, 37 and 38.

8. The antibody or fragment thereof of claim 1, wherein the antibody or fragment thereof comprises a heavy chain variable region sequence comprising the amino acid sequence selected from the group consisting of SEQ ID NOS: 58, 59, 79 and 80.

9. The antibody or fragment thereof of claim 1, wherein the antibody or fragment thereof comprises a non-CDR region of a heavy chain variable region sequence which is at least 80% identical to the non-CDR region of the heavy chain variable region sequence selected from the group consisting of SEQ ID NOS: 58, 59, 79 and 80.

10. The antibody or fragment thereof of claim 1, wherein the antibody or fragment thereof comprises a heavy chain variable framework region that is the product of a human gene selected from the group consisting of IGHV2-70*10 (SEQ ID NO: 19), IGHV2-70*01 (SEQ ID NO: 20), IGHV2-70*13 (SEQ ID NO: 21), IGHV2-5*09 (SEQ ID NO: 22), and IGHV2-70*11 (SEQ ID NO: 23).

11. The antibody or fragment thereof of claim 1, wherein the antibody or fragment thereof comprises a heavy chain variable framework region that is the product of human gene IGHV2-70*10 (SEQ ID NO: 19), and wherein in the heavy chain variable framework region at least one amino acid is replaced with a corresponding amino acid from a heavy chain variable framework region of a corresponding murine antibody of SEQ ID NO: 7 or wherein the antibody or fragment thereof comprises a heavy chain sequence comprising the amino acid sequence of SEQ ID NO: 32 and wherein in the heavy chain variable framework region at least one amino acid is replaced with a corresponding amino acid from the heavy chain variable framework region of the corresponding murine antibody of SEQ ID NO: 7.

12. The antibody or fragment thereof of claim 11, wherein the amino acid replacement is at an amino acid position selected from the group consisting of 23, 35, 48, 50, 60 and 62, wherein the amino acid position of each group member is indicated according to the Kabat numbering.

13. The antibody or fragment thereof of claim 11, wherein the amino acid replacement is selected from the group consisting of 23S, 35G, 48L, 50H, 60N, and 62A, wherein the amino acid position of each group member is indicated according to the Kabat numbering.

14. The antibody or fragment thereof of claim 1, wherein the antibody or fragment thereof comprises a light chain variable region sequence comprising the amino acid sequence of SEQ ID NO: 8, wherein the antibody or fragment thereof comprises a non-CDR region of a light chain variable region sequence which is at least 80% identical to the non-CDR region of the light chain variable region sequence of SEQ ID NO: 8, and/or wherein the light chain sequence comprises a non-CDR region which is at least 80% identical to the non-CDR region of the light chain variable region sequence of the light chain sequence selected from the group consisting of SEQ ID NOS: 45, 46, 47 and 49.

15. The antibody or fragment thereof of claim 14, wherein the antibody or fragment thereof comprises a light chain sequence comprising the amino acid sequence selected from the group consisting of SEQ ID NOS: 45, 46, 47 and 49.

16. The antibody or fragment thereof of claim 1, wherein the antibody or fragment thereof comprises a light chain variable region sequence comprising the amino acid sequence selected from the group consisting of SEQ ID NOS: 60, 86, 87 and 89, wherein the antibody or fragment thereof comprises a non-CDR region of a light chain variable region sequence which is at least 80% identical to the non-CDR region of the light chain variable region sequence selected from the group consisting of SEQ ID NOS: 60, 86, 87 and 89 and/or wherein the antibody or fragment thereof comprises a light chain variable framework region that is the product of a human gene selected from the group consisting of IGKV3-11*01 (SEQ ID NO: 24), IGKV1-39*01 (SEQ ID NO: 25), IGKV1D-39*01 (SEQ ID NO: 26), IGKV3-11*02 (SEQ ID NO: 27) and IGKV3-20*01 (SEQ ID NO: 28).

17. The antibody or fragment thereof of claim 1, wherein the antibody or fragment thereof comprises a light chain variable framework region that is the product of human gene IGKV3-11*01 (SEQ ID NO: 24) and wherein in the light chain variable framework region at least one amino acid is deleted or is replaced with a corresponding amino acid from a light chain variable framework region of a corresponding murine antibody of SEQ ID NO: 8 and/or wherein the antibody or fragment thereof comprises a light chain sequence comprising the amino acid sequence of SEQ ID NO: 39 and wherein in the light chain variable framework region at least one amino acid is deleted or replaced with a corresponding amino acid from the light chain variable framework region of the corresponding murine antibody of SEQ ID NO: 8.

18. The antibody or fragment thereof of claim 17, wherein the amino acid replacement is at an amino acid position selected from the group consisting of 1, 33, 34, 46, 47, 54, 56, and 71, wherein the amino acid position of each group member is indicated according to the Kabat numbering.

19. The antibody or fragment thereof of claim 17, wherein the amino acid replacement is selected from the group consisting of 1Q, 33M, 34H, 46P, 47W, 54L, 56S, and 71Y, wherein the amino acid position of each group member is indicated according to the Kabat numbering.

20. The antibody or fragment thereof of claim 17, wherein the amino acid deletion is at amino acid position 31, wherein the amino acid position is indicated according to the Kabat numbering.

21. The antibody of claim 1, wherein the antibody comprises:
(a) a heavy chain sequence comprising the amino acid sequence of SEQ ID NO:37 and
(b) a light chain sequence comprising the amino acid sequence of SEQ ID NO:47.

22. The antibody or fragment thereof of claim 1, wherein the antibody or fragment thereof comprises:
(a) a heavy chain variable region comprising the amino acid sequence of SEQ ID NO:58 and
(b) a light chain variable region comprising the amino acid sequence of SEQ ID NO:60.

23. The antibody or fragment thereof of claim 1, wherein the antibody further comprises a heavy and/or a light constant region.

24. The antibody or fragment thereof of claim 23, wherein the heavy chain constant region is selected from the group of human immunoglobulins consisting of IGHG1, non fucosylated IGHG1, and IGHG4.

25. The antibody or fragment thereof of claim 1, wherein the antibody is a monovalent antibody, a full length antibody, or an antibody fragment selected from the group consisting of Fab, Fab', Fab'-SH, Fv, F (ab')2, scFv, bispecific single chain Fv dimers, diabodies, triabodies and scFv genetically fused to the same or a different antibody.

26. The antibody or fragment thereof of claim 1, wherein the antibody comprises a variant Fc region which comprises at least one amino acid modification relative to the Fc region of a parent antibody, whereas the antibody comprising the variant Fc region exhibits altered effector function compared to the parent antibody.

27. The antibody or fragment thereof of claim 1, wherein the antibody or fragment thereof binds to human OX40 with an affinity (Kd) of 110 nM or less and/or the antibody has a Fab fragment thermostability temperature greater than 75° C.

28. A kit comprising an antagonistic antibody or fragment thereof that binds to human OX40, wherein said antibody or fragment thereof comprises:
a heavy chain CDR1 comprising the amino acid sequence of SEQ ID NO: 1, a heavy chain CDR2 comprising the amino acid sequence of SEQ ID NO: 2, and a heavy chain CDR3 comprising the amino acid sequence of SEQ ID NO: 3; and
a light chain CDR1 comprising the amino acid sequence of SEQ ID NO: 4, a light chain CDR2 comprising the amino acid sequence of SEQ ID NO: 5 and a light chain CDR3 comprising the amino acid sequence of SEQ ID NO: 6.

* * * * *

UNITED STATES PATENT AND TRADEMARK OFFICE
CERTIFICATE OF CORRECTION

| | | |
|---|---|---|
| PATENT NO. | : 12,281,169 B2 | Page 1 of 1 |
| APPLICATION NO. | : 17/854904 | |
| DATED | : April 22, 2025 | |
| INVENTOR(S) | : Attinger et al. | |

It is certified that error appears in the above-identified patent and that said Letters Patent is hereby corrected as shown below:

In the Claims

At Column 141, Line 44, replace "The manufacture antibody or fragment thereof" with -- The antibody or fragment thereof --.

At Column 144, Lines 20-22, replace "wherein the antibody further comprises a heavy and/or a light constant region" with -- wherein the antibody further comprises a heavy and/or a light chain constant region --.

Signed and Sealed this
Tenth Day of June, 2025

Coke Morgan Stewart
*Acting Director of the United States Patent and Trademark Office*

SEQUENCE LISTING

<160> NUMBER OF SEQ ID NOS: 89

<210> SEQ ID NO 1
<211> LENGTH: 10
<212> TYPE: PRT
<213> ORGANISM: Mus musculus
<220> FEATURE:
<223> OTHER INFORMATION: heavy chain CDR 1 of 1D4

<400> SEQUENCE: 1

Gly Phe Ser Leu Ser Thr Ser Gly Met Gly
1               5                   10

<210> SEQ ID NO 2
<211> LENGTH: 7
<212> TYPE: PRT
<213> ORGANISM: Mus musculus
<220> FEATURE:
<223> OTHER INFORMATION: heavy chain CDR 2 of 1D4

<400> SEQUENCE: 2

Ile Trp Trp Asp Asp Asp Lys
1               5

<210> SEQ ID NO 3
<211> LENGTH: 10
<212> TYPE: PRT
<213> ORGANISM: Mus musculus
<220> FEATURE:
<223> OTHER INFORMATION: heavy chain CDR 3 of 1D4

<400> SEQUENCE: 3

Ala Arg Ile Asp Trp Asp Gly Phe Ala Tyr
1               5                   10

<210> SEQ ID NO 4
<211> LENGTH: 5
<212> TYPE: PRT
<213> ORGANISM: Mus musculus
<220> FEATURE:
<223> OTHER INFORMATION: light chain CDR 1 of 1D4

<400> SEQUENCE: 4

Ser Ser Val Ser Tyr
1               5

<210> SEQ ID NO 5
<211> LENGTH: 3
<212> TYPE: PRT
<213> ORGANISM: Mus musculus
<220> FEATURE:
<223> OTHER INFORMATION: light chain CDR 2 of 1D4

<400> SEQUENCE: 5

Ala Thr Ser
1

<210> SEQ ID NO 6
<211> LENGTH: 9
<212> TYPE: PRT
<213> ORGANISM: Mus musculus
<220> FEATURE:
<223> OTHER INFORMATION: light chain CDR 3 of 1D4

<400> SEQUENCE: 6

Gln Gln Trp Ser Ser Asn Pro Trp Thr
1               5

<210> SEQ ID NO 7
<211> LENGTH: 118
<212> TYPE: PRT
<213> ORGANISM: Mus musculus
<220> FEATURE:
<223> OTHER INFORMATION: heavy chain variable region sequence of 1D4

<400> SEQUENCE: 7

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Thr Ala
    50                  55                  60

Leu Lys Ser Gly Leu Thr Ile Ser Lys Asp Thr Ser Lys Asn Gln Val
65                  70                  75                  80

Phe Leu Lys Ile Ala Ser Val Asp Thr Thr Asp Thr Ala Thr Tyr Tyr
            85                  90                  95

Cys Ala Arg Ile Asp Trp Asp Gly Phe Ala Tyr Trp Gly Gln Gly Thr
            100                 105                 110

Leu Val Thr Val Ser Ser
        115

<210> SEQ ID NO 8
<211> LENGTH: 106
<212> TYPE: PRT
<213> ORGANISM: Mus musculus
<220> FEATURE:
<223> OTHER INFORMATION: light chain variable region sequence of 1D4

<400> SEQUENCE: 8

Gln Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Asn Arg Val Glu Ala Glu
65                  70                  75                  80

Asp Ala Ala Thr Tyr Tyr Cys Gln Gln Trp Ser Ser Asn Pro Trp Thr
            85                  90                  95

Phe Gly Gly Gly Thr Lys Leu Glu Ile Lys
            100                 105

<210> SEQ ID NO 9
<211> LENGTH: 354
<212> TYPE: DNA
<213> ORGANISM: Mus musculus
<220> FEATURE:
<223> OTHER INFORMATION: DNA sequence of heavy chain variable region
      sequence of 1D4

<400> SEQUENCE: 9
caggtgacgc tgaaggagtc tggccctggg atattgcagc cctcccagac cctcagtctg      60

```
acttgttctt tctctgggtt ttcactgagc acttctggta tgggtgtagg ctggattcgt    120
cagccttcag ggaagggtct ggagtggctg gcacacattt ggtgggatga tgataagtac    180
tataacacag ccctgaagag cgggctcaca atctccaagg atacctccaa aaaccaggtc    240
ttcctcaaga tcgccagtgt ggacactaca gatactgcca catactactg tgctcgaata    300
gactgggacg ggtttgctta ctggggccaa gggactctgg tcactgtctc ctca          354

<210> SEQ ID NO 10
<211> LENGTH: 318
<212> TYPE: DNA
<213> ORGANISM: Mus musculus
<220> FEATURE:
<223> OTHER INFORMATION: DNA sequence of light chain variable region
      sequence of 1D4

<400> SEQUENCE: 10
cagattgtac tgactcagtc tccagcaatc ctgtctgcat ctccagggga aaggtcaca     60 atgacttgca gggccagctc aagtgtaagt tacatgcact ggtaccagca aaagccagga    120
tcctccccca aaccctggat ttatgccaca tccaacctgg cttctggagt ccctgctcgc    180
ttcagtggca gtgggtctgg gacctcttac tctctcacaa tcaacagagt ggaggctgaa    240
gatgctgcca cttattactg ccagcagtgg agtagtaacc cgtggacgtt cggtggaggc    300
accaagctgg agataaaa                                                  318

<210> SEQ ID NO 11
<211> LENGTH: 186
<212> TYPE: PRT
<213> ORGANISM: Homo sapiens
<220> FEATURE:
<223> OTHER INFORMATION: human OX40 extracellular domain (amino acids
      29-214 of P43489)

<400> SEQUENCE: 11

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185
```

<210> SEQ ID NO 12
<211> LENGTH: 277
<212> TYPE: PRT
<213> ORGANISM: Homo sapiens
<220> FEATURE:
<223> OTHER INFORMATION: human OX40 receptor (P43489)

<400> SEQUENCE: 12

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 13
<211> LENGTH: 13
<212> TYPE: PRT
<213> ORGANISM: Mus musculus
<220> FEATURE:
<223> OTHER INFORMATION: extended heavy chain CDR 1 of 1D4

<400> SEQUENCE: 13

Gly Phe Ser Leu Ser Thr Ser Gly Met Gly Val Gly Trp
1               5                   10

-continued

```
<210> SEQ ID NO 14
<211> LENGTH: 19
<212> TYPE: PRT
<213> ORGANISM: Mus musculus
<220> FEATURE:
<223> OTHER INFORMATION: extended heavy chain CDR 2 of 1D4

<400> SEQUENCE: 14

Trp Leu Ala His Ile Trp Trp Asp Asp Asp Lys Tyr Tyr Asn Thr Ala
1               5                   10                  15

Leu Lys Ser

<210> SEQ ID NO 15
<211> LENGTH: 10
<212> TYPE: PRT
<213> ORGANISM: Mus musculus
<220> FEATURE:
<223> OTHER INFORMATION: extended heavy chain CDR 3 of 1D4

<400> SEQUENCE: 15

Ala Arg Ile Asp Trp Asp Gly Phe Ala Tyr
1               5                   10

<210> SEQ ID NO 16
<211> LENGTH: 12
<212> TYPE: PRT
<213> ORGANISM: Mus musculus
<220> FEATURE:
<223> OTHER INFORMATION: extended light chain CDR 1 of 1D4

<400> SEQUENCE: 16

Arg Ala Ser Ser Ser Val Ser Tyr Met His Trp Tyr
1               5                   10

<210> SEQ ID NO 17
<211> LENGTH: 11
<212> TYPE: PRT
<213> ORGANISM: Mus musculus
<220> FEATURE:
<223> OTHER INFORMATION: extended light chain CDR 2 of 1D4

<400> SEQUENCE: 17

Pro Trp Ile Tyr Ala Thr Ser Asn Leu Ala Ser
1               5                   10

<210> SEQ ID NO 18
<211> LENGTH: 9
<212> TYPE: PRT
<213> ORGANISM: Mus musculus
<220> FEATURE:
<223> OTHER INFORMATION: extended light chain CDR 3 of 1D4

<400> SEQUENCE: 18

Gln Gln Trp Ser Ser Asn Pro Trp Thr
1               5

<210> SEQ ID NO 19
<211> LENGTH: 115
<212> TYPE: PRT
<213> ORGANISM: Homo sapiens
<220> FEATURE:
<223> OTHER INFORMATION: human IGHV2-70*10

<400> SEQUENCE: 19

Gln Val Thr Leu Lys Glu Ser Gly Pro Ala Leu Val Lys Pro Thr Gln
1               5                   10                  15
```

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
            35                  40                  45

Trp Ile Ala Arg Ile Asp Trp Asp Asp Asp Lys Tyr Tyr Ser Thr Ser
        50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Tyr Phe Asp Tyr Trp Gly Gln Gly Thr Leu Val Thr
            100                 105                 110

Val Ser Ser
        115

<210> SEQ ID NO 20
<211> LENGTH: 115
<212> TYPE: PRT
<213> ORGANISM: Homo sapiens
<220> FEATURE:
<223> OTHER INFORMATION: human IGHV2-70*01

<400> SEQUENCE: 20

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
            35                  40                  45

Trp Leu Ala Leu Ile Asp Trp Asp Asp Asp Lys Tyr Tyr Ser Thr Ser
        50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Tyr Phe Asp Tyr Trp Gly Gln Gly Thr Leu Val Thr
            100                 105                 110

Val Ser Ser
        115

<210> SEQ ID NO 21
<211> LENGTH: 115
<212> TYPE: PRT
<213> ORGANISM: Homo sapiens
<220> FEATURE:
<223> OTHER INFORMATION: human IGHV2-70*13

<400> SEQUENCE: 21

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
            35                  40                  45

Trp Leu Ala Leu Ile Asp Trp Asp Asp Asp Lys Tyr Tyr Ser Thr Ser
        50                  55                  60

Leu Lys Thr Arg Leu Thr Ile Ser Lys Asp Thr Ser Lys Asn Gln Val
65                  70                  75                  80

```
Val Leu Thr Met Thr Asn Met Asp Pro Val Asp Thr Ala Thr Tyr Tyr
                85                  90                  95

Cys Ala Arg Ile Tyr Phe Asp Tyr Trp Gly Gln Gly Thr Leu Val Thr
            100                 105                 110

Val Ser Ser
        115

<210> SEQ ID NO 22
<211> LENGTH: 115
<212> TYPE: PRT
<213> ORGANISM: Homo sapiens
<220> FEATURE:
<223> OTHER INFORMATION: human IGHV2-5*09

<400> SEQUENCE: 22

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Gly Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Tyr Phe Asp Tyr Trp Gly Gln Gly Thr Leu Val Thr
            100                 105                 110

Val Ser Ser
        115

<210> SEQ ID NO 23
<211> LENGTH: 115
<212> TYPE: PRT
<213> ORGANISM: Homo sapiens
<220> FEATURE:
<223> OTHER INFORMATION: human IGHV2-70*11

<400> SEQUENCE: 23

Arg Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
            35                  40                  45

Trp Leu Ala Arg Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Tyr Phe Asp Tyr Trp Gly Gln Gly Thr Leu Val Thr
            100                 105                 110

Val Ser Ser
        115
```

```
<210> SEQ ID NO 24
<211> LENGTH: 107
<212> TYPE: PRT
<213> ORGANISM: Homo sapiens
<220> FEATURE:
<223> OTHER INFORMATION: human IGKV3-11*01

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 25
<211> LENGTH: 107
<212> TYPE: PRT
<213> ORGANISM: Homo sapiens
<220> FEATURE:
<223> OTHER INFORMATION: human IGKV1-39*01

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 26
<211> LENGTH: 107
<212> TYPE: PRT
<213> ORGANISM: Homo sapiens
<220> FEATURE:
<223> OTHER INFORMATION: human IGKV1D-39*01

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Trp
                85                  90                  95
Thr Phe Gly Gln Gly Thr Lys Val Glu Ile Lys
            100                 105
```

<210> SEQ ID NO 27
<211> LENGTH: 107
<212> TYPE: PRT
<213> ORGANISM: Homo sapiens
<220> FEATURE:
<223> OTHER INFORMATION: IGKV3-11*02

<400> SEQUENCE: 27

```
Glu Ile Val Leu Thr Gln Ser Pro Ala Thr Leu Ser Leu Ser Pro Gly
  1               5                  10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
        50                  55                  60
Ser Gly Ser Gly Arg Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Trp
                85                  90                  95
Thr Phe Gly Gln Gly Thr Lys Val Glu Ile Lys
            100                 105
```

<210> SEQ ID NO 28
<211> LENGTH: 108
<212> TYPE: PRT
<213> ORGANISM: Homo sapiens
<220> FEATURE:
<223> OTHER INFORMATION: human IGKV3-20*01

<400> SEQUENCE: 28

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys
            100                 105
```

<210> SEQ ID NO 29
<211> LENGTH: 118
<212> TYPE: PRT

<213> ORGANISM: Artificial
<220> FEATURE:
<223> OTHER INFORMATION: VH1 heavy chain variable domain

<400> SEQUENCE: 29

```
Gln Val Thr Leu Lys Glu Ser Gly Pro Ala Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Met Gly Val Ser Trp Ile Arg Gln Pro Pro Gly Lys Ala Leu Glu
        35                  40                  45
Trp Ile Ala Arg Ile Trp Trp Asp Asp Lys Tyr Tyr Ser Thr Ser
    50                  55                  60
Leu Lys Thr Arg Leu Thr Ile Ser Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala Arg Ile Asp Trp Asp Gly Phe Ala Tyr Trp Gly Gln Gly Thr
            100                 105                 110
Leu Val Thr Val Ser Ser
        115
```

<210> SEQ ID NO 30
<211> LENGTH: 107
<212> TYPE: PRT
<213> ORGANISM: Artificial
<220> FEATURE:
<223> OTHER INFORMATION: VL1 light chain variable domain

<400> SEQUENCE: 30

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Ser Ser Val Ser Tyr Tyr
            20                  25                  30
Leu Ala Trp Tyr Gln Gln Lys Pro Gly Gln Ala Pro Arg Leu Leu Ile
        35                  40                  45
Tyr Ala Thr Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Trp Ser Ser Asn Pro Trp
                85                  90                  95
Thr Phe Gly Gln Gly Thr Lys Val Glu Ile Lys
            100                 105
```

<210> SEQ ID NO 31
<211> LENGTH: 720
<212> TYPE: DNA
<213> ORGANISM: Artificial
<220> FEATURE:
<223> OTHER INFORMATION: VH1-VL1 scFv cDNA

<400> SEQUENCE: 31

```
caggtcacac tgaaagagtc tggacccgcc ctggtcaagc ccacccagac actgaccctg     60
acctgcacct tcagcggctt cagcctgagc acaagcggca tgggcgtgtc ctggatcaga    120
cagcctcctg gcaaggccct ggaatggatc gcccggattt ggtgggacga cgacaagtac    180
tacagcacca gcctgaaaac ccggctgacc atcagcaagg acaccagcaa gaaccaggtg    240
```

```
gtgctgacca tgaccaacat ggaccccgtg acaccgcca cctactactg cgccagaatc    300
gactgggacg gcttcgccta ttggggccag ggaaccctgg tcaccgtgtc tagcggaggc    360
ggaggatctg gcggcggagg aagtggcgga gggggatctg agatcgtgct gacacagagc    420
cccgccaccc tgtctctgag ccctggcgaa agagccaccc tgagctgtag agccagcagc    480
agcgtgtcct actacctggc ctggtatcag cagaagcccg gccaggctcc ccggctgctg    540
atctacgcca ccagcaatcg ggccacaggc atccctgcca gattttctgg cagcggctcc    600
ggcaccgact tcaccctgac catctccagc ctggaacccg aggacttcgc cgtgtactac    660
tgccagcagt ggtccagcaa ccccctggac atttggccagg caccaaggt ggaaatcaag    720
```

<210> SEQ ID NO 32
<211> LENGTH: 448
<212> TYPE: PRT
<213> ORGANISM: Artificial
<220> FEATURE:
<223> OTHER INFORMATION: VH1 heavy chain IGHG1

<400> SEQUENCE: 32

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Ile Ala Arg Ile Trp Trp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 33
<211> LENGTH: 448
<212> TYPE: PRT
<213> ORGANISM: Artificial
<220> FEATURE:
<223> OTHER INFORMATION: VH2 heavy chain IGHG1

<400> SEQUENCE: 33

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Ile Ala Arg Ile Trp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 34
<211> LENGTH: 448
<212> TYPE: PRT
<213> ORGANISM: Artificial
<220> FEATURE:
<223> OTHER INFORMATION: VH3 heavy chain IGHG1

<400> SEQUENCE: 34

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Ile Ala His Ile Trp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 35
<211> LENGTH: 448
<212> TYPE: PRT
<213> ORGANISM: Artificial
<220> FEATURE:
<223> OTHER INFORMATION: VH4 heavy chain IGHG1

<400> SEQUENCE: 35

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
                20                  25                  30

Gly Met Gly Val Ser Trp Ile Arg Gln Pro Pro Gly Lys Ala Leu Glu
            35                  40                  45

Trp Ile Ala His Ile Trp Trp Asp Asp Lys Tyr Tyr Ser Thr Ser
            50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Asp Trp Asp Gly Phe Ala Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 36
<211> LENGTH: 448

<212> TYPE: PRT
<213> ORGANISM: Artificial
<220> FEATURE:
<223> OTHER INFORMATION: VH5 heavy chain IGHG1

<400> SEQUENCE: 36

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Ile Ala His Ile Trp Trp Asp Asp Lys Tyr Tyr Asn Thr Ala
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 37
<211> LENGTH: 448
<212> TYPE: PRT
<213> ORGANISM: Artificial
<220> FEATURE:
<223> OTHER INFORMATION: VH6 heavy chain IGHG1

<400> SEQUENCE: 37

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Ile Ala His Ile Trp Trp Asp Asp Lys Tyr Tyr Asn Thr Ala
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

-continued

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 38
<211> LENGTH: 448
<212> TYPE: PRT
<213> ORGANISM: Artificial
<220> FEATURE:
<223> OTHER INFORMATION: VH7 heavy chain IGHG1

<400> SEQUENCE: 38

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Asn Thr Ala
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 39
<211> LENGTH: 214
<212> TYPE: PRT
<213> ORGANISM: Artificial
<220> FEATURE:
<223> OTHER INFORMATION: VL1 light chain

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Tyr
            20                  25                  30

Leu Ala Trp Tyr Gln Gln Lys Pro Gly Gln Ala Pro Arg Leu Leu Ile
        35                  40                  45

Tyr Ala Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Ser Ser Asn Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 214
<212> TYPE: PRT
<213> ORGANISM: Artificial
<220> FEATURE:
<223> OTHER INFORMATION: VL2 light chain

<400> SEQUENCE: 40

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Tyr
            20                  25                  30

Met Ala Trp Tyr Gln Gln Lys Pro Gly Gln Ala Pro Arg Leu Leu Ile
        35                  40                  45

Tyr Ala Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Ser Ser Asn Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 41
<211> LENGTH: 214
<212> TYPE: PRT
<213> ORGANISM: Artificial
<220> FEATURE:
<223> OTHER INFORMATION: VL3 light chain

<400> SEQUENCE: 41

```
Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Ser Val Ser Tyr Tyr
            20                  25                  30

Leu Ala Trp Tyr Gln Gln Lys Pro Gly Gln Ala Pro Arg Leu Leu Ile
        35                  40                  45

Tyr Ala Thr Ser Asn Arg Ala Thr Gly Ile Pro Ala Arg Phe Ser Gly
 50                  55                  60

Ser Gly Ser Gly Thr Asp Tyr Thr Leu Thr Ile Ser Ser Leu Glu Pro
 65                  70                  75                  80

Glu Asp Phe Ala Val Tyr Tyr Cys Gln Gln Trp Ser Ser Asn Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 214
<212> TYPE: PRT
<213> ORGANISM: Artificial
<220> FEATURE:
<223> OTHER INFORMATION: VL4 light chain

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Tyr
            20                  25                  30

Met Ala Trp Tyr Gln Gln Lys Pro Gly Gln Ala Pro Arg Leu Leu Ile
        35                  40                  45

Tyr Ala Thr Ser Asn Arg Ala Thr Gly Ile Pro Ala Arg Phe Ser Gly
 50                  55                  60

Ser Gly Ser Gly Thr Asp Tyr Thr Leu Thr Ile Ser Ser Leu Glu Pro
 65                  70                  75                  80

Glu Asp Phe Ala Val Tyr Tyr Cys Gln Gln Trp Ser Ser Asn Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 43
<211> LENGTH: 214
<212> TYPE: PRT
<213> ORGANISM: Artificial
<220> FEATURE:
<223> OTHER INFORMATION: VL5 light chain

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Tyr
            20                  25                  30

Met Ala Trp Tyr Gln Gln Lys Pro Gly Gln Ala Pro Arg Pro Trp Ile
        35                  40                  45

Tyr Ala Thr Ser Asn Arg Ala Thr Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Trp Ser Ser Asn Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 44
<211> LENGTH: 214
<212> TYPE: PRT
<213> ORGANISM: Artificial
<220> FEATURE:
<223> OTHER INFORMATION: VL6 light chain

<400> SEQUENCE: 44

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Tyr
```

```
                  20                  25                  30

Met Ala Trp Tyr Gln Gln Lys Pro Gly Gln Ala Pro Arg Pro Trp Ile
            35                  40                  45

Tyr Ala Thr Ser Asn Arg Ala Thr Gly Ile Pro Ala Arg Phe Ser Gly
        50                  55                  60

Ser Gly Ser Gly Thr Asp Tyr Thr Leu Thr Ile Ser Ser Leu Glu Pro
 65                  70                  75                  80

Glu Asp Phe Ala Val Tyr Tyr Cys Gln Gln Trp Ser Ser Asn Pro Trp
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 213
<212> TYPE: PRT
<213> ORGANISM: Artificial
<220> FEATURE:
<223> OTHER INFORMATION: VL7 light chain

<400> SEQUENCE: 45

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Ser Tyr Met
            20                  25                  30

Ala Trp Tyr Gln Gln Lys Pro Gly Gln Ala Pro Arg Leu Leu Ile Tyr
        35                  40                  45

Ala Thr Ser Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 46
<211> LENGTH: 213
<212> TYPE: PRT
<213> ORGANISM: Artificial
<220> FEATURE:
<223> OTHER INFORMATION: VL8 light chain

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Ala Thr Ser Asn Arg Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 47
<211> LENGTH: 213
<212> TYPE: PRT
<213> ORGANISM: Artificial
<220> FEATURE:
<223> OTHER INFORMATION: VL9 light chain

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

```
His Trp Tyr Gln Gln Lys Pro Gly Gln Ala Pro Arg Pro Trp Ile Tyr
            35                  40                  45

Ala Thr Ser Asn Arg Ala Thr Gly Ile Pro Ala Arg Phe Ser Gly Ser
 50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Trp Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 48
<211> LENGTH: 213
<212> TYPE: PRT
<213> ORGANISM: Artificial
<220> FEATURE:
<223> OTHER INFORMATION: VL10 light chain

<400> SEQUENCE: 48

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Ser Tyr Met
            20                  25                  30

Ala Trp Tyr Gln Gln Lys Pro Gly Gln Ala Pro Arg Leu Leu Ile Tyr
            35                  40                  45

Ala Thr Ser Asn Leu Ala Ser Gly Ile Pro Ala Arg Phe Ser Gly Ser
 50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Trp Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

-continued

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 49
<211> LENGTH: 213
<212> TYPE: PRT
<213> ORGANISM: Artificial
<220> FEATURE:
<223> OTHER INFORMATION: VL11 light chain

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 50
<211> LENGTH: 448
<212> TYPE: PRT
<213> ORGANISM: Artificial
<220> FEATURE:
<223> OTHER INFORMATION: heavy chain of 1D4 chimera

<400> SEQUENCE: 50

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

-continued

Trp Leu Ala His Ile Trp Trp Asp Asp Lys Tyr Tyr Asn Thr Ala
                50              55              60

Leu Lys Ser Gly Leu Thr Ile Ser Lys Asp Thr Ser Lys Asn Gln Val
65              70              75              80

Phe Leu Lys Ile Ala Ser Val Asp Thr Thr Asp Thr Ala Thr Tyr Tyr
                85              90              95

Cys Ala Arg Ile Asp Trp Asp Gly Phe Ala Tyr Trp Gly Gln Gly Thr
                100             105             110

Leu Val Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
        130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
                165             170             175

Ser Ser Gly Leu Tyr Ser Leu Ser Ser Val Val Thr Val Pro Ser Ser
                180             185             190

Ser Leu Gly Thr Gln Thr Tyr Ile Cys Asn Val Asn His Lys Pro Ser
            195             200             205

Asn Thr Lys Val Asp Lys Lys Val Glu Pro Lys Ser Cys Asp Lys Thr
        210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
                245             250             255

Thr Pro Glu Val Thr Cys Val Val Val Asp Val Ser His Glu Asp Pro
                260             265             270

Glu Val Lys Phe Asn Trp Tyr Val Asp Gly Val Glu Val His Asn Ala
            275             280             285

Lys Thr Lys Pro Arg Glu Glu Gln Tyr Asn Ser Thr Tyr Arg Val Val
        290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
                325             330             335

Ile Ser Lys Ala Lys Gly Gln Pro Arg Glu Pro Gln Val Tyr Thr Leu
                340             345             350

Pro Pro Ser Arg Asp Glu Leu Thr Lys Asn Gln Val Ser Leu Thr Cys
            355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
                405             410             415

Arg Trp Gln Gln Gly Asn Val Phe Ser Cys Ser Val Met His Glu Ala
                420             425             430

Leu His Asn His Tyr Thr Gln Lys Ser Leu Ser Leu Ser Pro Gly Lys
            435             440             445

<210> SEQ ID NO 51
<211> LENGTH: 213

```
<212> TYPE: PRT
<213> ORGANISM: Artificial
<220> FEATURE:
<223> OTHER INFORMATION: light chain of 1D4 chimera

<400> SEQUENCE: 51
```

Gln Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Asn Arg Val Glu Ala Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

```
<210> SEQ ID NO 52
<211> LENGTH: 191
<212> TYPE: PRT
<213> ORGANISM: Rattus norvegicus
<220> FEATURE:
<223> OTHER INFORMATION: rat OX40 extracellular domain

<400> SEQUENCE: 52
```

Val Thr Val Lys Leu Asn Cys Val Lys Asp Thr Tyr Pro Ser Gly His
1               5                   10                  15

Lys Cys Cys Arg Glu Cys Gln Pro Gly His Gly Met Val Ser Arg Cys
            20                  25                  30

Asp His Thr Arg Asp Thr Val Cys His Pro Cys Glu Pro Gly Phe Tyr
        35                  40                  45

Asn Glu Ala Val Asn Tyr Asp Thr Cys Lys Gln Cys Thr Gln Cys Asn
    50                  55                  60

His Arg Ser Gly Ser Glu Leu Lys Gln Asn Cys Thr Pro Thr Glu Asp
65                  70                  75                  80

Thr Val Cys Gln Cys Arg Pro Gly Thr Gln Pro Arg Gln Asp Ser Ser
                85                  90                  95

His Lys Leu Gly Val Asp Cys Val Pro Cys Pro Pro Gly His Phe Ser
            100                 105                 110

Pro Gly Ser Asn Gln Ala Cys Lys Pro Trp Thr Asn Cys Thr Leu Ser
            115                 120                 125

Gly Lys Gln Ile Arg His Pro Ala Ser Asn Ser Leu Asp Thr Val Cys
    130                 135                 140

Glu Asp Arg Ser Leu Leu Ala Thr Leu Leu Trp Glu Thr Gln Arg Thr
145                 150                 155                 160

Thr Phe Arg Pro Thr Thr Val Pro Ser Thr Thr Val Trp Pro Arg Thr
                165                 170                 175

Ser Gln Leu Pro Ser Thr Pro Thr Leu Val Ala Pro Glu Gly Pro
            180                 185                 190

<210> SEQ ID NO 53
<211> LENGTH: 191
<212> TYPE: PRT
<213> ORGANISM: Artificial
<220> FEATURE:
<223> OTHER INFORMATION: human-rat OX40 extracellular domain chimera
      RHRR

<400> SEQUENCE: 53

Val Thr Val Lys Leu Asn Cys Val Lys Asp Thr Tyr Pro Ser Gly His
1               5                   10                  15

Lys Cys Cys Arg Glu Cys Gln Pro Gly His Gly Met Val Ser Arg Cys
                20                  25                  30

Asp His Thr Arg Asp Thr Val Cys Arg Pro Cys Gly Pro Gly Phe Tyr
            35                  40                  45

Asn Asp Val Val Ser Ser Lys Pro Cys Lys Pro Cys Thr Trp Cys Asn
50                  55                  60

Leu Arg Ser Gly Ser Glu Arg Lys Gln Leu Cys Thr Ala Thr Gln Asp
65                  70                  75                  80

Thr Val Cys Gln Cys Arg Pro Gly Thr Gln Pro Arg Gln Asp Ser Ser
                85                  90                  95

His Lys Leu Gly Val Asp Cys Val Pro Cys Pro Pro Gly His Phe Ser
            100                 105                 110

Pro Gly Ser Asn Gln Ala Cys Lys Pro Trp Thr Asn Cys Thr Leu Ser
            115                 120                 125

Gly Lys Gln Ile Arg His Pro Ala Ser Asn Ser Leu Asp Thr Val Cys
    130                 135                 140

Glu Asp Arg Ser Leu Leu Ala Thr Leu Leu Trp Glu Thr Gln Arg Thr
145                 150                 155                 160

Thr Phe Arg Pro Thr Thr Val Pro Ser Thr Thr Val Trp Pro Arg Thr
                165                 170                 175

Ser Gln Leu Pro Ser Thr Pro Thr Leu Val Ala Pro Glu Gly Pro
            180                 185                 190

<210> SEQ ID NO 54
<211> LENGTH: 190
<212> TYPE: PRT
<213> ORGANISM: Artificial
<220> FEATURE:
<223> OTHER INFORMATION: human-rat OX40 extracellular domain chimera
      RHHH

<400> SEQUENCE: 54

Val Thr Val Lys Leu Asn Cys Val Lys Asp Thr Tyr Pro Ser Gly His
1               5                   10                  15

Lys Cys Cys Arg Glu Cys Gln Pro Gly His Gly Met Val Ser Arg Cys
                20                  25                  30

```
Asp His Thr Arg Asp Thr Val Cys His Pro Cys Gly Pro Gly Phe Tyr
        35                  40                  45

Asn Asp Val Val Ser Ser Lys Pro Cys Lys Pro Cys Thr Trp Cys Asn
 50                  55                  60

Leu Arg Ser Gly Ser Glu Arg Lys Gln Leu Cys Thr Ala Thr Gln Asp
 65                  70                  75                  80

Thr Val Cys Arg Cys Arg Ala Gly Thr Gln Pro Leu Asp Ser Tyr Lys
                 85                  90                  95

Pro Gly Val Asp Cys Ala Pro Cys Pro Pro Gly His Phe Ser Pro Gly
                100                 105                 110

Asp Asn Gln Ala Cys Lys Pro Trp Thr Asn Cys Thr Leu Ala Gly Lys
                115                 120                 125

His Thr Leu Gln Pro Ala Ser Asn Ser Ser Asp Ala Ile Cys Glu Asp
    130                 135                 140

Arg Asp Pro Pro Ala Thr Gln Pro Gln Glu Thr Gln Gly Pro Pro Ala
145                 150                 155                 160

Arg Pro Ile Thr Val Gln Pro Thr Glu Ala Trp Pro Arg Thr Ser Gln
                165                 170                 175

Gly Pro Ser Thr Arg Pro Val Glu Val Pro Gly Gly Arg Ala
                180                 185                 190

<210> SEQ ID NO 55
<211> LENGTH: 187
<212> TYPE: PRT
<213> ORGANISM: Artificial
<220> FEATURE:
<223> OTHER INFORMATION: human-rat OX40 extracellular domain chimera
      HHRR

<400> SEQUENCE: 55

Leu His Cys Val Gly Asp Thr Tyr Pro Ser Asn Asp Arg Cys Cys His
  1               5                  10                  15

Glu Cys Arg Pro Gly Asn Gly Met Val Ser Arg Cys Ser Arg Ser Gln
                 20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
 50                  55                  60

Ser Glu Arg Lys Gln Leu Cys Thr Ala Thr Gln Asp Thr Val Cys Gln
 65                  70                  75                  80

Cys Arg Pro Gly Thr Gln Pro Arg Gln Asp Ser Ser His Lys Leu Gly
                 85                  90                  95

Val Asp Cys Val Pro Cys Pro Pro Gly His Phe Ser Pro Gly Ser Asn
                100                 105                 110

Gln Ala Cys Lys Pro Trp Thr Asn Cys Thr Leu Ser Gly Lys Gln Ile
    115                 120                 125

Arg His Pro Ala Ser Asn Ser Leu Asp Thr Val Cys Glu Asp Arg Ser
    130                 135                 140

Leu Leu Ala Thr Leu Leu Trp Glu Thr Gln Arg Thr Thr Phe Arg Pro
145                 150                 155                 160

Thr Thr Val Pro Ser Thr Thr Val Trp Pro Arg Thr Ser Gln Leu Pro
                165                 170                 175

Ser Thr Pro Thr Leu Val Ala Pro Glu Gly Pro
                180                 185
```

<210> SEQ ID NO 56
<211> LENGTH: 189
<212> TYPE: PRT
<213> ORGANISM: Artificial
<220> FEATURE:
<223> OTHER INFORMATION: human-rat OX40 extracellular domain chimera RRHH

<400> SEQUENCE: 56

```
Val Thr Val Lys Leu Asn Cys Val Lys Asp Thr Tyr Pro Ser Gly His
1               5                   10                  15

Lys Cys Cys Arg Glu Cys Gln Pro Gly His Gly Met Val Ser Arg Cys
            20                  25                  30

Asp His Thr Arg Asp Thr Val Cys His Pro Cys Glu Pro Gly Phe Tyr
        35                  40                  45

Asn Glu Ala Val Asn Tyr Asp Thr Cys Lys Gln Cys Thr Gln Cys Asn
    50                  55                  60

His Arg Ser Gly Ser Glu Leu Lys Gln Asn Cys Thr Pro Thr Glu Asp
65                  70                  75                  80

Thr Val Cys Arg Cys Arg Ala Gly Thr Gln Pro Leu Asp Ser Tyr Lys
                85                  90                  95

Pro Gly Val Asp Cys Ala Pro Cys Pro Pro Gly His Phe Ser Pro Gly
            100                 105                 110

Asp Asn Gln Ala Cys Lys Pro Trp Thr Asn Cys Thr Leu Ala Gly Lys
        115                 120                 125

His Thr Leu Gln Pro Ala Ser Asn Ser Ser Asp Ala Ile Cys Glu Asp
    130                 135                 140

Arg Asp Pro Pro Ala Thr Gln Pro Gln Glu Thr Gln Gly Pro Pro Ala
145                 150                 155                 160

Arg Pro Ile Thr Val Gln Pro Thr Glu Ala Trp Pro Arg Thr Ser Gln
                165                 170                 175

Gly Pro Ser Thr Arg Pro Val Glu Val Pro Gly Gly Arg
            180                 185
```

<210> SEQ ID NO 57
<211> LENGTH: 445
<212> TYPE: PRT
<213> ORGANISM: Artificial
<220> FEATURE:
<223> OTHER INFORMATION: VH6 heavy chain IGHG4 S228P

<400> SEQUENCE: 57

```
Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Ile Ala His Ile Trp Trp Asp Asp Lys Tyr Tyr Asn Thr Ala
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125
```

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
            210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 58
<211> LENGTH: 118
<212> TYPE: PRT
<213> ORGANISM: Artificial
<220> FEATURE:
<223> OTHER INFORMATION: VH6 heavy chain variable domain

<400> SEQUENCE: 58

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Gly Trp Ile Arg Gln Pro Pro Gly Lys Ala Leu Glu
            35                  40                  45

-continued

```
Trp Ile Ala His Ile Trp Trp Asp Asp Lys Tyr Tyr Asn Thr Ala
        50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Asp Trp Asp Gly Phe Ala Tyr Trp Gly Gln Gly Thr
                100                 105                 110

Leu Val Thr Val Ser Ser
            115
```

<210> SEQ ID NO 59
<211> LENGTH: 118
<212> TYPE: PRT
<213> ORGANISM: Artificial
<220> FEATURE:
<223> OTHER INFORMATION: VH7 heavy chain variable domain

<400> SEQUENCE: 59

```
Gln Val Thr Leu Lys Glu Ser Gly Pro Ala Leu Val Lys Pro Thr Gln
 1                   5                  10                  15

Thr Leu Thr Leu Thr Cys Ser Phe Ser Gly Phe Ser Leu Ser Thr Ser
                 20                  25                  30

Gly Met Gly Val Gly Trp Ile Arg Gln Pro Pro Gly Lys Ala Leu Glu
             35                  40                  45

Trp Leu Ala His Ile Trp Trp Asp Asp Lys Tyr Tyr Asn Thr Ala
        50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Asp Trp Asp Gly Phe Ala Tyr Trp Gly Gln Gly Thr
                100                 105                 110

Leu Val Thr Val Ser Ser
            115
```

<210> SEQ ID NO 60
<211> LENGTH: 106
<212> TYPE: PRT
<213> ORGANISM: Artificial
<220> FEATURE:
<223> OTHER INFORMATION: VL9 light chain variable domain

<400> SEQUENCE: 60

```
Glu Ile Val Leu Thr Gln Ser Pro Ala Thr Leu Ser Leu Ser Pro Gly
 1                   5                  10                  15

Glu Arg Ala Thr Leu Ser Cys Arg Ala Ser Ser Ser Val Ser Tyr Met
                 20                  25                  30

His Trp Tyr Gln Gln Lys Pro Gly Gln Ala Pro Arg Pro Trp Ile Tyr
             35                  40                  45

Ala Thr Ser Asn Arg Ala Thr Gly Ile Pro Ala Arg Phe Ser Gly Ser
        50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Trp Thr
                 85                  90                  95

Phe Gly Gln Gly Thr Lys Val Glu Ile Lys
            100                 105
```

<210> SEQ ID NO 61
<211> LENGTH: 354
<212> TYPE: DNA
<213> ORGANISM: Artificial
<220> FEATURE:
<223> OTHER INFORMATION: VH6 heavy chain variable domain DNA coding
      sequence

<400> SEQUENCE: 61
caggtcacac tgaaagagtc tggacccgcc ctggtcaagc ccacccagac actgaccctg    60
acctgcagct tcagcggctt cagcctgagc acaagcggca tgggcgtggg ctggatcaga   120
cagcctcctg gcaaggccct ggaatggatc gcccatattt ggtgggatga tgataaatat   180
tataacaccg ccctgaaaac ccgcctgacc atcagcaagg acaccagcaa gaaccaggtg   240
gtgctgacca tgaccaacat ggaccccgtg gacaccgcca cctactactg cgccagaatc   300
gactgggacg gcttcgccta ttggggccag ggaaccctgg tgaccgtgag cagc          354

<210> SEQ ID NO 62
<211> LENGTH: 354
<212> TYPE: DNA
<213> ORGANISM: Artificial
<220> FEATURE:
<223> OTHER INFORMATION: VH7 heavy chain variable domain DNA coding
      sequence

<400> SEQUENCE: 62
caggtcacac tgaaagagtc tggacccgcc ctggtcaagc ccacccagac actgaccctg    60
acctgcagct tcagcggctt cagcctgagc acaagcggca tgggcgtggg ctggatcaga   120
cagcctcctg gcaaggccct ggaatggctc gcccacattt ggtgggatga tgataaatat   180
tataacaccg ccctgaaaac ccgcctgacc atcagcaagg acaccagcaa gaaccaggtg   240
gtgctgacca tgaccaacat ggaccccgtg gacaccgcca cctactactg cgccagaatc   300
gactgggacg gcttcgccta ttggggccag ggcaccctgg tgaccgtgag cagc          354

<210> SEQ ID NO 63
<211> LENGTH: 318
<212> TYPE: DNA
<213> ORGANISM: Artificial
<220> FEATURE:
<223> OTHER INFORMATION: VL9 light chain variable domain DNA coding
      sequence

<400> SEQUENCE: 63
gagatcgtgc tgacacagag ccccgccacc ctgtctctga gccctggcga aagagccacc    60
ctgagctgta gagccagcag cagcgtgtcc tacatgcact ggtatcagca gaagcccggc   120
caggcgccgc gcccgtggat ttatgcgacc agcaatcggg ccacaggcat ccctgccaga   180
ttttctggca gcggctccgg caccgactac accctgacca tctccagcct ggaacccgag   240
gacttcgccg tgtactactg ccagcagtgg tccagcaacc cctggacatt tggccagggc   300
accaaagtgg aaattaaa                                                 318

<210> SEQ ID NO 64
<211> LENGTH: 10
<212> TYPE: PRT
<213> ORGANISM: Mus musculus
<220> FEATURE:
<223> OTHER INFORMATION: heavy chain CDR 1 of VH6

```
<400> SEQUENCE: 64

Gly Phe Ser Leu Ser Thr Ser Gly Met Gly
1               5                   10

<210> SEQ ID NO 65
<211> LENGTH: 7
<212> TYPE: PRT
<213> ORGANISM: Mus musculus
<220> FEATURE:
<223> OTHER INFORMATION: heavy chain CDR 2 of VH6

<400> SEQUENCE: 65

Ile Trp Trp Asp Asp Asp Lys
1               5

<210> SEQ ID NO 66
<211> LENGTH: 10
<212> TYPE: PRT
<213> ORGANISM: Mus musculus
<220> FEATURE:
<223> OTHER INFORMATION: heavy chain CDR 3 of VH6

<400> SEQUENCE: 66

Ala Arg Ile Asp Trp Asp Gly Phe Ala Tyr
1               5                   10

<210> SEQ ID NO 67
<211> LENGTH: 5
<212> TYPE: PRT
<213> ORGANISM: Mus musculus
<220> FEATURE:
<223> OTHER INFORMATION: light chain CDR 1 of VL9

<400> SEQUENCE: 67

Ser Ser Val Ser Tyr
1               5

<210> SEQ ID NO 68
<211> LENGTH: 3
<212> TYPE: PRT
<213> ORGANISM: Mus musculus
<220> FEATURE:
<223> OTHER INFORMATION: light chain CDR 2 of VL9

<400> SEQUENCE: 68

Ala Thr Ser
1

<210> SEQ ID NO 69
<211> LENGTH: 9
<212> TYPE: PRT
<213> ORGANISM: Mus musculus
<220> FEATURE:
<223> OTHER INFORMATION: light chain CDR 3 of VL9

<400> SEQUENCE: 69

Gln Gln Trp Ser Ser Asn Pro Trp Thr
1               5

<210> SEQ ID NO 70
<211> LENGTH: 13
<212> TYPE: PRT
<213> ORGANISM: Mus musculus
<220> FEATURE:
<223> OTHER INFORMATION: extended heavy chain CDR 1 of VH6

<400> SEQUENCE: 70
```

```
Gly Phe Ser Leu Ser Thr Ser Gly Met Gly Val Gly Trp
1               5                   10
```

```
<210> SEQ ID NO 71
<211> LENGTH: 19
<212> TYPE: PRT
<213> ORGANISM: Artificial
<220> FEATURE:
<223> OTHER INFORMATION: extended heavy chain CDR 2 of VH6

<400> SEQUENCE: 71

Trp Ile Ala His Ile Trp Trp Asp Asp Lys Tyr Tyr Asn Thr Ala
1               5                   10                  15

Leu Lys Thr
```

```
<210> SEQ ID NO 72
<211> LENGTH: 10
<212> TYPE: PRT
<213> ORGANISM: Mus musculus
<220> FEATURE:
<223> OTHER INFORMATION: extended heavy chain CDR 3 of VH6

<400> SEQUENCE: 72

Ala Arg Ile Asp Trp Asp Gly Phe Ala Tyr
1               5                   10
```

```
<210> SEQ ID NO 73
<211> LENGTH: 12
<212> TYPE: PRT
<213> ORGANISM: Mus musculus
<220> FEATURE:
<223> OTHER INFORMATION: extended light chain CDR 1 of VL9

<400> SEQUENCE: 73

Arg Ala Ser Ser Ser Val Ser Tyr Met His Trp Tyr
1               5                   10
```

```
<210> SEQ ID NO 74
<211> LENGTH: 11
<212> TYPE: PRT
<213> ORGANISM: Artificial
<220> FEATURE:
<223> OTHER INFORMATION: extended light chain CDR 2 of VL9

<400> SEQUENCE: 74

Pro Trp Ile Tyr Ala Thr Ser Asn Arg Ala Thr
1               5                   10
```

```
<210> SEQ ID NO 75
<211> LENGTH: 9
<212> TYPE: PRT
<213> ORGANISM: Mus musculus
<220> FEATURE:
<223> OTHER INFORMATION: extended light chain CDR 3 of VL9

<400> SEQUENCE: 75

Gln Gln Trp Ser Ser Asn Pro Trp Thr
1               5
```

```
<210> SEQ ID NO 76
<211> LENGTH: 44
<212> TYPE: PRT
<213> ORGANISM: Homo sapiens
<220> FEATURE:
<223> OTHER INFORMATION: module 2 of human OX40 extracellular domain
```

```
<400> SEQUENCE: 76

Arg Pro Cys Gly Pro Gly Phe Tyr Asn Asp Val Val Ser Ser Lys Pro
1               5                   10                  15

Cys Lys Pro Cys Thr Trp Cys Asn Leu Arg Ser Gly Ser Glu Arg Lys
                20                  25                  30

Gln Leu Cys Thr Ala Thr Gln Asp Thr Val Cys Arg
            35                  40

<210> SEQ ID NO 77
<211> LENGTH: 118
<212> TYPE: PRT
<213> ORGANISM: Artificial
<220> FEATURE:
<223> OTHER INFORMATION: VH2 heavy chain variable domain

<400> SEQUENCE: 77

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
                20                  25                  30

Gly Met Gly Val Ser Trp Ile Arg Gln Pro Pro Gly Lys Ala Leu Glu
            35                  40                  45

Trp Ile Ala Arg Ile Trp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
            100                 105                 110

Leu Val Thr Val Ser Ser
            115

<210> SEQ ID NO 78
<211> LENGTH: 118
<212> TYPE: PRT
<213> ORGANISM: Artificial
<220> FEATURE:
<223> OTHER INFORMATION: VH3 heavy chain variable domain

<400> SEQUENCE: 78

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Ala Leu Glu
            35                  40                  45

Trp Ile Ala His Ile Trp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
            100                 105                 110

Leu Val Thr Val Ser Ser
            115
```

```
<210> SEQ ID NO 79
<211> LENGTH: 118
<212> TYPE: PRT
<213> ORGANISM: Artificial
<220> FEATURE:
<223> OTHER INFORMATION: VH4 heavy chain variable domain

<400> SEQUENCE: 79

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Ile Ala His Ile Trp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
            100                 105                 110

Leu Val Thr Val Ser Ser
        115

<210> SEQ ID NO 80
<211> LENGTH: 118
<212> TYPE: PRT
<213> ORGANISM: Artificial
<220> FEATURE:
<223> OTHER INFORMATION: VH5 heavy chain variable domain

<400> SEQUENCE: 80

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Ile Ala His Ile Trp Trp Asp Asp Asp Lys Tyr Tyr Asn Thr Ala
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asp Trp Asp Gly Phe Ala Tyr Trp Gly Gln Gly Thr
            100                 105                 110

Leu Val Thr Val Ser Ser
        115

<210> SEQ ID NO 81
<211> LENGTH: 107
<212> TYPE: PRT
<213> ORGANISM: Artificial
<220> FEATURE:
<223> OTHER INFORMATION: VL2 light chain variable domain

<400> SEQUENCE: 81

Glu Ile Val Leu Thr Gln Ser Pro Ala Thr Leu Ser Leu Ser Pro Gly
```

```
                1               5                   10                  15
Glu Arg Ala Thr Leu Ser Cys Arg Ala Ser Ser Ser Val Ser Tyr Tyr
                20                  25                  30

Met Ala Trp Tyr Gln Gln Lys Pro Gly Gln Ala Pro Arg Leu Leu Ile
        35                  40                  45

Tyr Ala Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Ser Ser Asn Pro Trp
                85                  90                  95

Thr Phe Gly Gln Gly Thr Lys Val Glu Ile Lys
            100                 105
```

<210> SEQ ID NO 82
<211> LENGTH: 107
<212> TYPE: PRT
<213> ORGANISM: Artificial
<220> FEATURE:
<223> OTHER INFORMATION: VL3 light chain variable domain

<400> SEQUENCE: 82

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Tyr
                20                  25                  30

Leu Ala Trp Tyr Gln Gln Lys Pro Gly Gln Ala Pro Arg Leu Leu Ile
        35                  40                  45

Tyr Ala Thr Ser Asn Arg Ala Thr Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Trp Ser Ser Asn Pro Trp
                85                  90                  95

Thr Phe Gly Gln Gly Thr Lys Val Glu Ile Lys
            100                 105
```

<210> SEQ ID NO 83
<211> LENGTH: 107
<212> TYPE: PRT
<213> ORGANISM: Artificial
<220> FEATURE:
<223> OTHER INFORMATION: VL4 light chain variable domain

<400> SEQUENCE: 83

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Tyr
                20                  25                  30

Met Ala Trp Tyr Gln Gln Lys Pro Gly Gln Ala Pro Arg Leu Leu Ile
        35                  40                  45

Tyr Ala Thr Ser Asn Arg Ala Thr Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Trp Ser Ser Asn Pro Trp
                85                  90                  95
```

```
Thr Phe Gly Gln Gly Thr Lys Val Glu Ile Lys
            100                 105

<210> SEQ ID NO 84
<211> LENGTH: 107
<212> TYPE: PRT
<213> ORGANISM: Artificial
<220> FEATURE:
<223> OTHER INFORMATION: VL5 light chain variable domain

<400> SEQUENCE: 84

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Tyr
            20                  25                  30

Met Ala Trp Tyr Gln Gln Lys Pro Gly Gln Ala Pro Arg Pro Trp Ile
            35                  40                  45

Tyr Ala Thr Ser Asn Arg Ala Thr Gly Ile Pro Ala Arg Phe Ser Gly
        50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Trp Ser Ser Asn Pro Trp
                85                  90                  95

Thr Phe Gly Gln Gly Thr Lys Val Glu Ile Lys
            100                 105

<210> SEQ ID NO 85
<211> LENGTH: 107
<212> TYPE: PRT
<213> ORGANISM: Artificial
<220> FEATURE:
<223> OTHER INFORMATION: VL6 light chain variable domain

<400> SEQUENCE: 85

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Tyr Tyr
            20                  25                  30

Met Ala Trp Tyr Gln Gln Lys Pro Gly Gln Ala Pro Arg Pro Trp Ile
            35                  40                  45

Tyr Ala Thr Ser Asn Arg Ala Thr Gly Ile Pro Ala Arg Phe Ser Gly
        50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Trp Ser Ser Asn Pro Trp
                85                  90                  95

Thr Phe Gly Gln Gly Thr Lys Val Glu Ile Lys
            100                 105

<210> SEQ ID NO 86
<211> LENGTH: 106
<212> TYPE: PRT
<213> ORGANISM: Artificial
<220> FEATURE:
<223> OTHER INFORMATION: VL7 light chain variable domain

<400> SEQUENCE: 86

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
```

```
                20                  25                  30

Ala Trp Tyr Gln Gln Lys Pro Gly Gln Ala Pro Arg Leu Leu Ile Tyr
            35                  40                  45

Ala Thr Ser Asn Arg Ala Thr Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Trp Thr
                85                  90                  95

Phe Gly Gln Gly Thr Lys Val Glu Ile Lys
            100                 105

<210> SEQ ID NO 87
<211> LENGTH: 106
<212> TYPE: PRT
<213> ORGANISM: Artificial
<220> FEATURE:
<223> OTHER INFORMATION: VL8 light chain variable domain

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Leu Leu Ile Tyr
            35                  40                  45

Ala Thr Ser Asn Arg Ala Thr Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Trp Thr
                85                  90                  95

Phe Gly Gln Gly Thr Lys Val Glu Ile Lys
            100                 105

<210> SEQ ID NO 88
<211> LENGTH: 106
<212> TYPE: PRT
<213> ORGANISM: Artificial
<220> FEATURE:
<223> OTHER INFORMATION: VL10 light chain variable domain

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Ala Trp Tyr Gln Gln Lys Pro Gly Gln Ala Pro Arg Leu Leu Ile Tyr
            35                  40                  45

Ala Thr Ser Asn Leu Ala Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Trp Thr
                85                  90                  95

Phe Gly Gln Gly Thr Lys Val Glu Ile Lys
            100                 105
```

```
<210> SEQ ID NO 89
<211> LENGTH: 106
<212> TYPE: PRT
<213> ORGANISM: Artificial
<220> FEATURE:
<223> OTHER INFORMATION: VL11 light chain variable domain

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Trp Thr
                85                  90                  95

Phe Gly Gln Gly Thr Lys Val Glu Ile Lys
                100                 105
```